(12) United States Patent
Kruegel et al.

(10) Patent No.: US 11,760,758 B2
(45) Date of Patent: Sep. 19, 2023

(54) MITRAGYNINE ANALOGS FOR THE TREATMENT OF PAIN, MOOD DISORDERS AND SUBSTANCE USE DISORDERS

(71) Applicants: The Trustees of Columbia University in the City of New York, New York, NY (US); The Research Foundation for Mental Hygiene, Inc., Menands, NY (US); Sloan-Kettering Institute for Cancer Research, New York, NY (US)

(72) Inventors: Andrew C. Kruegel, Secaucus, NJ (US); Dalibor Sames, New York, NY (US); Srijita Bhowmik, New York, NY (US); Vaclav Havel, New York, NY (US); Juraj Galeta, New York, NY (US); Jonathan A. Javitch, Dobbs Ferry, NY (US); Susruta Majumdar, New York, NY (US)

(73) Assignees: THE TRUSTEES OF COLUMBIA UNIVERSITY IN THE CITY OF NEW YORK, New York, NY (US); THE RESEARCH FOUNDATION FOR MENTAL HYGIENE, INC., Menands, NY (US); SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

(21) Appl. No.: 17/177,051

(22) Filed: Feb. 16, 2021

(65) Prior Publication Data
US 2021/0179619 A1     Jun. 17, 2021

Related U.S. Application Data

(63) Continuation of application No. PCT/US2019/046677, filed on Aug. 15, 2019.

(60) Provisional application No. 62/725,708, filed on Aug. 31, 2018, provisional application No. 62/765,134, filed on Aug. 16, 2018.

(51) Int. Cl.
*C07D 471/14*   (2006.01)
*A61K 31/4375*   (2006.01)
*C07D 471/20*   (2006.01)
*C07D 491/22*   (2006.01)

(52) U.S. Cl.
CPC ......... *C07D 471/20* (2013.01); *C07D 471/14* (2013.01); *C07D 491/22* (2013.01)

(58) Field of Classification Search
CPC ... C07D 471/14; A61K 31/4375; A61P 25/04; A61P 25/36

USPC ............................................. 546/62; 514/285
See application file for complete search history.

(56) References Cited

U.S. PATENT DOCUMENTS

| 8,247,428 B2 * | 8/2012 | Takayama ............ C07D 471/04 |
| | | 514/285 |
| 2009/0221623 A1 | 9/2009 | Takayama et al. |
| 2018/0134708 A1 | 5/2018 | Pasternak et al. |

OTHER PUBLICATIONS

International Preliminary Report on Patentability dated Feb. 16, 2021, including Written Opinion of the International Searching Authority dated Jan. 6, 2020, in connection with PCT International Application No. PCT/US2019/046677.
International Search Report dated Jan. 6, 2020 in connection with PCT International Application No. PCT/US2019/046677.
Kruegel, A.C. et al. "Synthetic and Receptor Signaling Explorations of the Mitragyna Alkaloids: Mitragynine as an Atypical Molecular Framework for Opiod Receptor Modulators." Journal of American Chemical Society, vol. 138, No. 21, Jun. 1, 2016, pp. 6754-6764.
PCT Recordation of Search History dated Oct. 2, 2019 in connection with PCT International Application No. PCT/US2019/046677.
Written Opinion of the International Searching Authority dated Jan. 6, 2020 in connection with PCT International Application No. PCT/US2019/046677.
Jared Wilson Klein, "Pharmacotherapy for Substance Use Disorders" CrossMark, Med Clin N Am 100 (Apr. 20, 2016) 891-910.
Michael Soyka, "Treatment-refractory substance use disorder: Focus on alcohol, opioids, and cocaine", Elsevier, Nov. 12, 2015, vol. 70, 148-161.

* cited by examiner

*Primary Examiner* — Charanjit Aulakh
(74) *Attorney, Agent, or Firm* — Gary J. Gershik

(57) ABSTRACT

The present invention provides a compound having the structure:

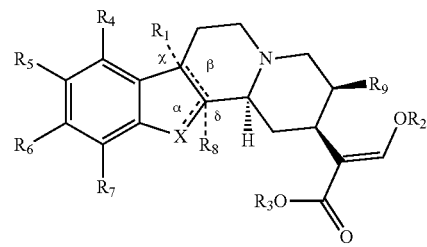

or a pharmaceutically acceptable salt or ester thereof, and a method of treating a subject afflicted with pain, a depressive disorder, a mood disorder or an anxiety disorder by administering the compound to the subject.

14 Claims, 4 Drawing Sheets

MITRAGYNINE ANALOGS FOR THE TREATMENT OF PAIN, MOOD DISORDERS AND SUBSTANCE USE DISORDERS

CROSS-REFERENCE TO RELATED APPLICATIONS

This application is a continuation of PCT International Application No. PCT/US2019/046677, filed Aug. 15, 2019, claiming the benefit of U.S. Provisional Applications Nos. 62/725,708, filed. Aug. 31, 2018, and 62/765,134, filed Aug. 16, 2018, the contents of each of which are hereby incorporated by reference herein.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Effective pain management is one of the greatest challenges of modern medicine. Morphine and other clinically used opioids that target the mu-opioid receptor (MOR) remain the preferred treatment of moderate to severe pain (Pasternak, G. W. et al. 2013). However, despite their proven efficacy, MOR drugs have problematic side effects, including respiratory depression, constipation, tolerance, physical dependence, and addiction liability (Corbett, A. D. et al. 2006; Compton, W. M. et al. 2016). Agonists of the related kappa-opioid receptor (KOR) have also been explored as potential analgesics. However, existing KOR agonists also suffer from significant disadvantages, including profound dysphoric and dissociative effects (Chavkin, C. et al. 2011). Therefore, development of safer opioid analgesics represents a long-standing scientific challenge of major health and societal importance. Novel structural motifs with unique opioid pharmacological profiles offer important opportunities to address this challenge and serve as valuable research probes and potential new medications.

There is also both historical and growing interest in the use of opioid receptor modulators as medicaments for depression and anxiety disorders (and other psychiatric diseases). Prior to the adoption of tricyclic antidepressants and electroshock therapy as favored treatments for depression, opioids were among the only pharmacological options available in the early 20th century (Berrocoso, E. et al. 2009). More recently, studies in both rodents (Besson, A. et al. 1996) and humans (Bodkin, J. A. et al. 1995) have suggested that MOR activation may lead to antidepressant and/or anxiolytic effects. Further, we have shown that the antidepressant tianeptine acts as a full agonist of the MOR (Gassaway, M. M. et al. 2014). On the molecular level, MORs are extensively expressed in the hippocampus and have been shown to exert a variety of indirect modulatory effects on glutamatergic neurotransmission in this brain region (Xie, C. W. et al. 1997; Svoboda, K. R. et al. 1999). Normalization and modulation of glutamate signaling has been strongly associated with the actions of antidepressants (Paul, I. A. and Skolnick, P. 2003) and indeed, the NMDA antagonist ketamine, shows rapid and efficacious antidepressant activity in human clinical trials (Zarate, C. A. Jr et al. 2006). Further, agonists of the delta-opioid receptor (DOR) and antagonists of the KOR have been demonstrated to show antidepressant and anxiolytic efficacy in animals (Jutkiewicz, E. M. et al. 2006; Carlezon, W. A. et al. 2016).

SUMMARY OF THE INVENTION

The present invention provides a compound having the structure:

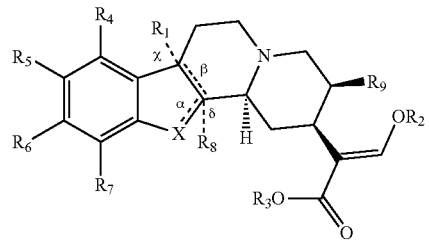

wherein
X is N or NH;
$R_1$ is —OH, —O-alkyl, —O(CO)-alkyl, or combines with $R_8$ to form a

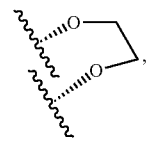

or is absent;
$R_2$ and $R_3$ are each, independently, —H or -alkyl;
$R_4$ is —H, —OH, -alkyl or —O-alkyl;
$R_5$, $R_6$ and $R_7$ are each, independently, —H, —F, —Cl, —Br, —I, CN, $CF_3$, $NO_2$, —OH, —$NH_2$, —C(O)$NH_2$, —NH(CO)-alkyl, —NH(CO)NR-alkyl, —NH(CO)-aryl, —NH(CO)NH-aryl, —O-alkyl, —O-aryl, —O-heteroaryl, alkyl, aryl or heteroaryl;
$R_8$ combines with $R_1$ to form a

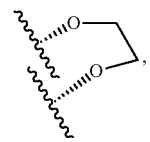

or is absent;
$R_9$ is alkyl, alkenyl, alkyl-OH, alkyl-O-alkyl, cycloalkyl, alkyl-cycloalkyl, alkyl-aryl or alkyl-heteroaryl;
α, β, χ and δ are each, independently, a bond that is absent or present,
wherein α, χ, and δ are absent, β is present, $R_1$ and $R_8$ are absent and X is NH, or
β and δ are absent, α and χ are present, $R_1$ is present, $R_8$ is absent and X is N, or
α and β are absent, x and d are present, $R_1$ and $R_8$ are present, and X is NH,
wherein when $R_9$ is ethyl, then $R_6$ is other than H or at least two of $R_5$, $R_6$ and $R_7$ are other than H, and
wherein when α, χ, and δ are absent, β is present, $R_2$ and $R_3$ are each —$CH_3$, $R_4$ is —$OCH_3$ and each of $R_5$, $R_6$ and $R_7$ is —H, then $R_9$ is other than vinyl,
or a pharmaceutically acceptable salt or ester thereof.

The present invention also provides a compound having the structure:

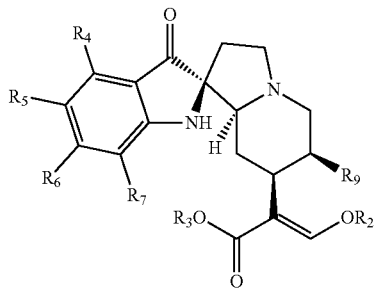

wherein

R$_2$ and R$_3$ are each, independently, —H or -alkyl;
R$_4$ is —H, —OH, -alkyl or —O-alkyl;
R$_5$, R$_6$ and R$_7$ are each, independently, —H, —F, —Cl, —Br, —I, CN, CF$_3$, NO$_2$, —OH, —NH$_2$, —C(O)NH$_2$, —NH(CO)-alkyl, —NH(CO)NH-alkyl, —NH(CO)-aryl, —NH(CO)NR-aryl, —O-alkyl, —O-aryl, —O-heteroaryl, alkyl, aryl or heteroaryl; and
R$_9$ is alkyl, alkenyl, alkyl-OH, alkyl-O-alkyl, cycloalkyl, alkyl-cycloalkyl, alkyl-aryl or alkyl-heteroaryl,
wherein when R$_9$ is ethyl, then R$_6$ is other than H or at least two of R$_5$, R$_6$ and R$_7$ are other than H, and
wherein when R$_2$ and R$_3$ are each —CH$_3$, R$_4$ is —OCH$_3$, R$_5$ and R$_7$ are each —H, and R$_9$ is ethyl, then R$_6$ is other than —OCH$_3$,
or a pharmaceutically acceptable salt or ester thereof.

DETAILED DESCRIPTION OF THE INVENTION

Figure 1:
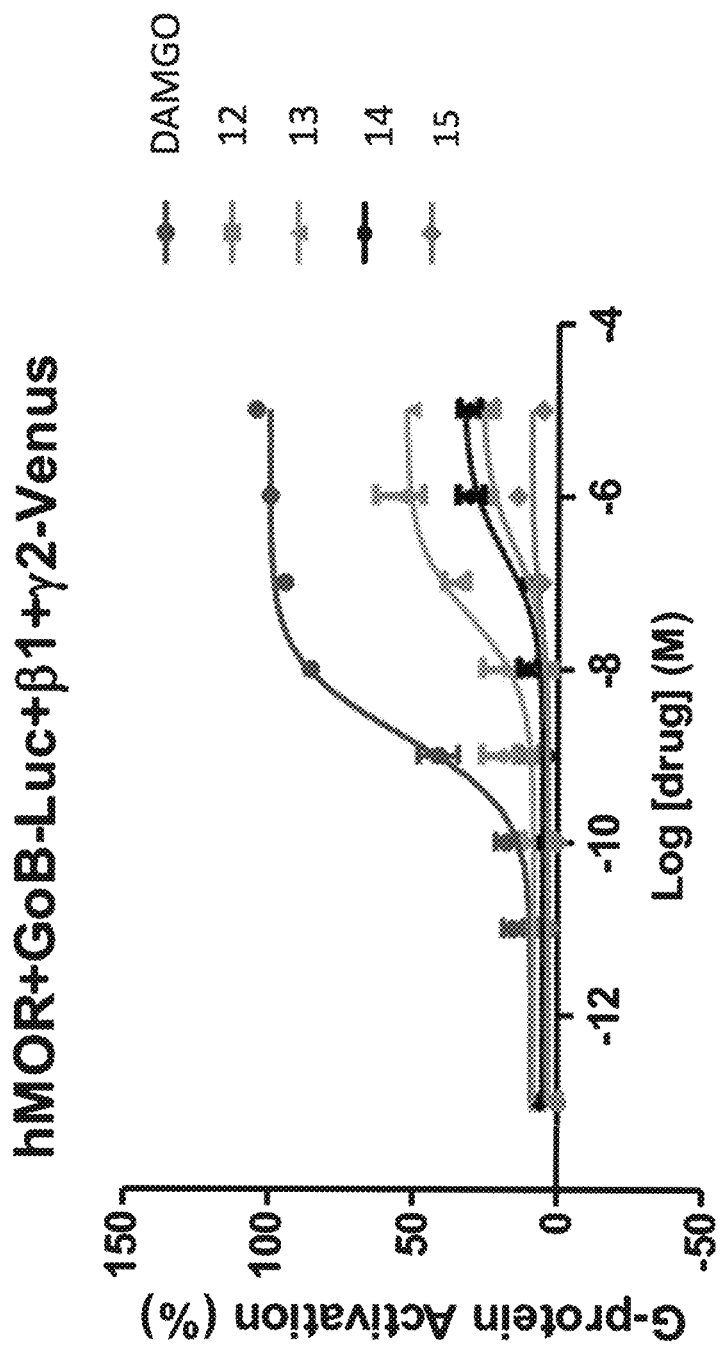
FIG. 1: Agonist activity of compounds 12, 13, 14 and 15 at human MOR; positive control=DAMGO. Bars represent SEM.

The present invention provides a compound having the structure:

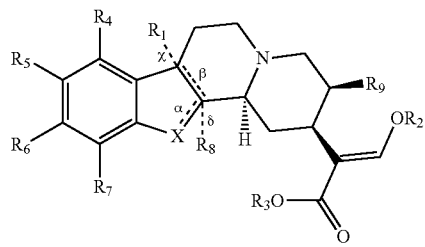

wherein
X is N or NH;
R$_1$ is —OH, —O-alkyl, —O(CO)-alkyl, or combines with R$_6$ to form a

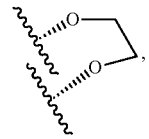

or is absent;
R$_2$ and R$_9$ are each, independently, —H or -alkyl;
R$_4$ is —H, —OH, -alkyl or —O-alkyl;
R$_5$, R$_6$ and R$_7$ are each, independently, —H, —F, —Cl, —Br, —I, —CN, —CF$_3$, —NO$_2$, —OH, —NH$_2$, —C(O)NH$_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl;
R$_8$ combines with R$_1$ to form a

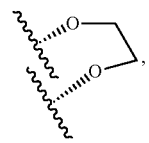

or is absent;
R$_9$ is alkyl, alkenyl, alkyl-OH, alkyl-O-alkyl, cycloalkyl, alkyl-cycloalkyl, alkyl-aryl or alkyl-heteroaryl;
α, β, χ and δ are each, independently, a bond that is absent or present,
wherein α, χ, and δ are absent, β is present, R$_1$ and R$_8$ are absent and X is NH, or β and δ are absent, α and χ are present, R$_1$ is present, R$_8$ is absent and X is N, or α and β are absent, χ and δ are present, R$_1$ and R$_8$ are present, and X is NH,
wherein when R$_9$ is ethyl, then R$_6$ is other than H or at least two of R$_5$, R$_6$ and R$_7$ are other than H, and
wherein when α, χ, and δ are absent, β is present, R$_2$ and R$_3$ are each —CH$_3$, R$_4$ is —OCH$_3$ and each of R$_5$, R$_6$ and R$_7$ is —H, then R$_9$ is other than vinyl,
or a pharmaceutically acceptable salt or ester thereof.
In some embodiments, the compound having the structure:

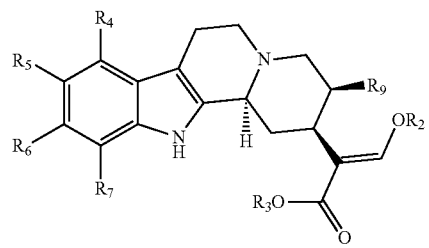

wherein
R$_2$ and R$_3$ are each, independently, —H or -alkyl;
R$_4$ is —H, —OH, -alkyl or —O-alkyl;
R$_5$, R$_6$ and R, are each, independently, —H, —F, —Cl, —Br, —I, —CN, —CF$_3$, —NO$_2$, —OH, —NH$_2$, —C(O)NH$_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl; and R$_9$ is alkyl, alkenyl, alkyl-OH, cycloalkyl, alkyl-cycloalkyl, alkyl-aryl or alkyl-heteroaryl;

wherein when R$_9$ is ethyl, then R$_6$ is other than H or at least two of R$_5$, R$_6$ and R$_7$ are other than H, and wherein when α, χ, and δ are absent, β is present, R$_2$ and R$_3$ are each —CH$_3$, R$_4$ is —OCH$_3$ and each of R$_5$, R$_6$ and R$_7$ is —H, then R$_9$ is other than vinyl, or a pharmaceutically acceptable salt or ester thereof.

In some embodiments, the compound wherein R$_6$ is other than H or at least two of R$_5$, R$_6$ and R$_7$ are other than H; and R$_9$ is alkyl, alkenyl, alkyl-OH, alkyl-O-alkyl, cycloalkyl, alkyl-cycloalkyl, alkyl-aryl or alkyl-heteroaryl.

In some embodiments, the compound wherein R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl.

In some embodiments, the compound wherein R$_5$, R$_6$ and R$_7$ are each H; and R$_9$ is C$_1$-alkyl, C$_3$-C$_{12}$ alkyl, C$_3$-C$_{12}$ alkenyl, alkyl-OH, alkyl-O-alkyl, cycloalkyl, alkyl-cycloalkyl, alkyl-aryl or alkyl-heteroaryl.

In some embodiments, the compound wherein R$_9$ is —CH$_3$, —CH$_2$CH$_2$CH$_3$, —CH$_3$CH=CH$_2$, —CH$_2$OH, —CH$_2$-cyclopropyl, —CH$_2$-cyclobutyl or —CH$_2$CH$_2$-phenyl.

In some embodiments, the compound wherein R$_5$ and R$_7$ are each H and R$_6$ is other than N.

In some embodiments, the compound having the structure:

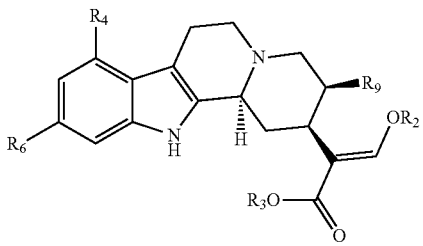

wherein
R$_2$ and R$_3$ are each, independently, —H or —CH$_3$;
R$_4$ is —OCH$_3$;
R$_6$ is —F, —Cl, —Br, —I, —CN, —CF$_3$, —NO$_2$, —OH, —CH$_3$, —OCH$_3$, —C(O)NH$_2$ or phenyl; and
R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein R$_5$ and R$_6$ are each other than H and R$_7$ is H.

In some embodiments, the compound having the structure:

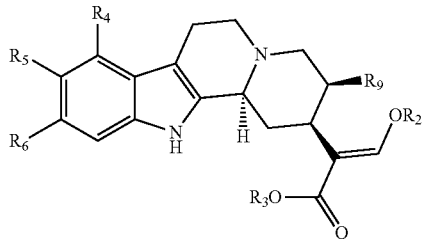

wherein
R$_2$ and R$_3$ are each, independently, —H or —CH$_3$;
R$_4$ is —OCH$_3$;
R$_5$ and R$_6$ are each, independently, —F, —Cl, —Br, —I, —CN, —CF$_3$, —NO$_2$, —OH, —CH$_3$, —OCH$_3$, —C(O)NH$_2$ or phenyl; and
R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein R$_6$ and R$_7$ are each other than H and R$_5$ is H.

In some embodiments, the compound having the structure:

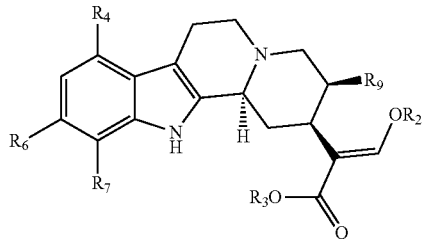

wherein
R$_2$ and R$_3$ are each, independently, —H or —CH$_3$;
R$_4$ is —OCH$_3$;
R$_6$ and R$_7$ are each, independently, —F, —Cl, —Br, —I, —CN, —CF$_3$, —NO$_2$, —OH, —CH$_3$, —OCH$_3$, —C(O)NH$_2$ or phenyl; and
R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein R$_5$ and R$_7$ are each other than H and R$_6$ is H.

In some embodiments, the compound having the structure:

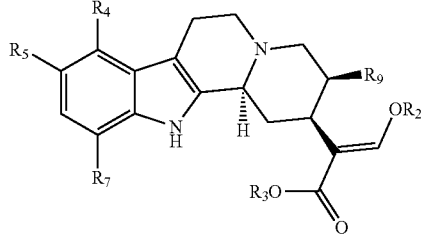

wherein

R₂ and R₃ are each, independently, —H or —CH₃;

R₄ is —OCH₃;

R₅ and R₇ are each, independently, —F, —Cl, —Br, —I, —CN, —CF₃, —NO₂, —OH, —CH₃, —OCH₃, —C(O)NH₂ or phenyl; and R₉ is —CH₃, —CH₂CH₃, —CH₂CH₂CH₃, —CH=CH₂, —CH₃CH=CH₂, —CH₂OH, —CH₂-cyclopropyl, —CH₂-cyclobutyl or —CH₂CH₂-phenyl, or a pharmaceutically acceptable salt or ester thereof.

In some embodiments, the compound wherein R₂ and R₃ are each —CH₃.

In some embodiments, the compound wherein R₄ is —OCH₃.

In some embodiments, the compound having the structure:

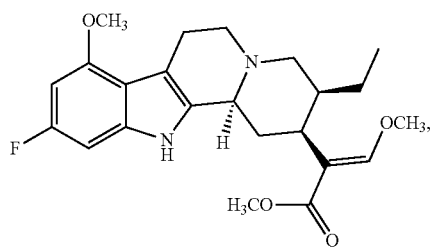

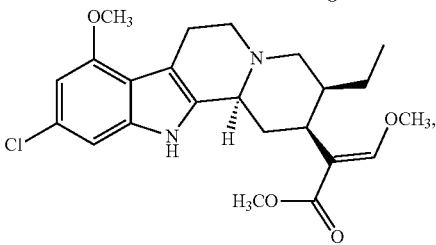

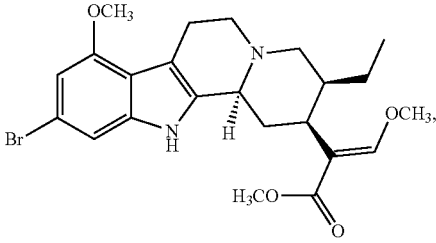

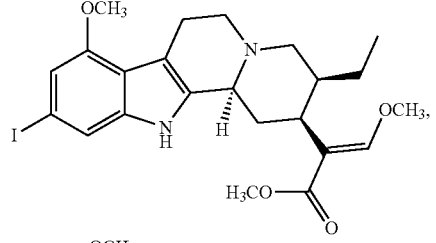

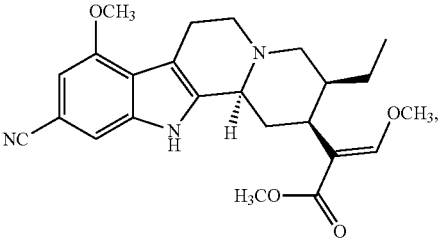

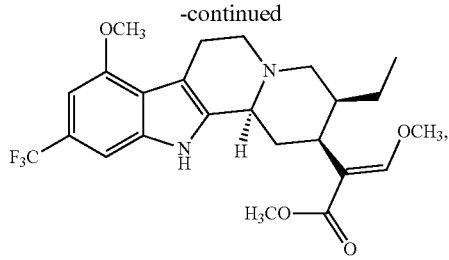

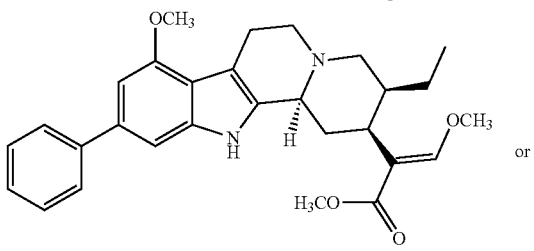

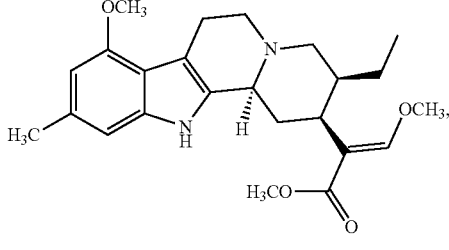

or a pharmaceutically acceptable salt or ester thereof.

In some embodiments, the compound having the structure:

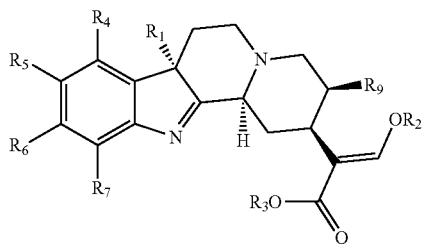

wherein

R₁ is —OH, —O-alkyl or —O(CO)-alkyl;

R₂ and R₃ are each, independently, —H or -alkyl;

R₄ is —H, —OH, -alkyl or —O-alkyl;

R₅, R₆ and R₇ are each, independently, —H, —F, —Cl, —Br, —I, —CN, —CF₃, —NO₂, —OH, —NH₂, —C(O)NH₂, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl;

R₉ is alkyl, alkenyl, alkyl-OH, alkyl-O-alkyl, cycloalkyl, alkyl-cycloalkyl, alkyl-aryl or alkyl-heteroaryl,
  wherein when R₉ is ethyl, then R₆ is other than H or at least two of R₅, R₆ and R₇ are other than H, and or a pharmaceutically acceptable salt or ester thereof.

In some embodiments, the compound wherein R₆ is other than H or at least two of R₅, R₆ and R₇ is other than H; and R₉ is alkyl, alkenyl, alkyl-OH, alkyl-O-alkyl, cycloalkyl, alkyl-cycloalkyl, alkyl-aryl or alkyl-heteroaryl.

In some embodiments, the compound wherein R₉ is —CH₃, —CH₂CH₃, —CH₂CH₂CH₃, —CH=CH₂, —CH₃CH=CH₂, —CH₂OH, —CH₂-cyclopropyl, —CH₂-cyclobutyl or —CH₂CH₂-phenyl.

In some embodiments, the compound wherein $R_5$, $R_6$ and $R_7$ are each H; and $R_9$ is $C_1$-alkyl, $C_3$-$C_{12}$ alkyl, alkenyl, alkyl-OH, alkyl-O-alkyl, cycloalkyl, alkyl-cycloalkyl, alkyl-aryl or alkyl-heteroaryl.

In some embodiments, the compound wherein $R_9$ is —$CH_3$, —$CH_2CH_2CH_3$, —CH=$CH_2$, —$CH_3CH$=$CH_2$, —$CH_2OH$, —$CH_2$-cyclopropyl, —$CH_2$-cyclobutyl or —$CH_2CH_2$-phenyl.

In some embodiments, the compound wherein $R_5$ and $R_7$ are each H and $R_6$ is other than H.

In some embodiments, the compound having the structure:

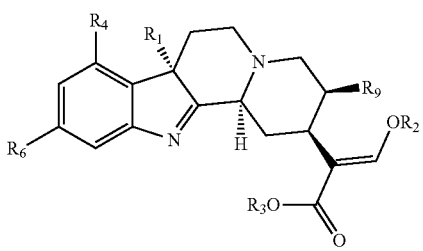

wherein
$R_1$ is —OH;
$R_2$ and $R_3$ are each, independently, —H or —$CH_3$;
$R_4$ is —$OCH_3$;
$R_6$ is —F, —Cl, —Br, —I, —CN, —$CF_3$, —$NO_2$, —OH, —$CH_3$, —$OCH_3$, —C(O)$NH_2$ or phenyl; and
$R_9$ is —$CH_3$, —$CH_2CH_3$, —$CH_2CH_2CH_3$, —CH=$CH_2$, —$CH_3CH$=$CH_2$, —$CH_2OH$, —$CH_2$-cyclopropyl, —$CH_2$-cyclobutyl or —$CH_2CH_2$-phenyl, or a pharmaceutically acceptable salt or ester thereof.

In some embodiments, the compound wherein $R_5$ and $R_6$ are each other than H and $R_7$ is H.

In some embodiments, the compound having the structure:

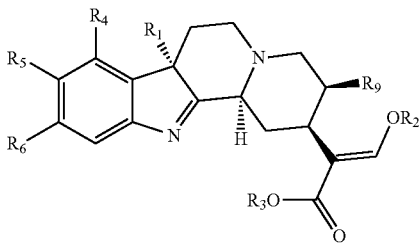

wherein
$R_1$ is —OH;
$R_2$ and $R_3$ are each, independently, —H or —$CH_3$;
$R_4$ is —$OCH_3$;
$R_9$ and $R_6$ are each, independently, —F, —Cl, —Br, —CN, —$CF_3$, —$NO_2$, —OH, —$CH_3$, —$OCH_3$, —C(O)$NH_2$ or phenyl; and
$R_9$ is —$CH_3$, —$CH_2CH_3$, —$CH_2CH_2CH_3$, —CH=$CH_2$, —$CH_3CH$=$CH_2$, —$CH_2OH$, —$CH_2$-cyclopropyl, —$CH_2$-cyclobutyl or —$CH_2CH_2$-phenyl, or a pharmaceutically acceptable salt or ester thereof.

In some embodiments, the compound wherein $R_6$ and $R_7$ are each other than H and $R_5$ is H.

In some embodiments, the compound having the structure:

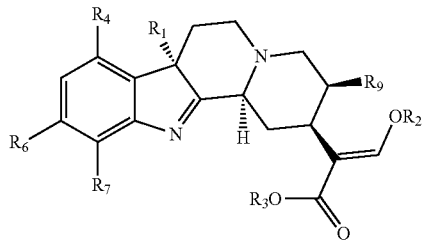

wherein
$R_1$ is —OH;
$R_2$ and $R_3$ are each, independently, —H or —$CH_3$;
$R_4$ is —$OCH_3$;
$R_6$ and $R_7$ are each, independently, —F, —Cl, —Br, —I, —CN, —$CF_3$, —$NO_2$, —OH, —$CH_3$, —$OCH_3$, —C(O)$NH_2$ or phenyl; and
$R_9$ is —$CH_3$, —$CH_2CH_3$, —$CH_2CH_2CH_3$, —CH=$CH_2$, —$CH_3CH$=$CH_2$, —$CH_2OH$, —$CH_2$-cyclopropyl, —$CH_2$-cyclobutyl or —$CH_2CH_2$-phenyl, or a pharmaceutically acceptable salt or ester thereof.

In some embodiments, the compound wherein $R_5$ and $R_7$ are each other than H and $R_6$ is H.

In some embodiments, the compound having the structure:

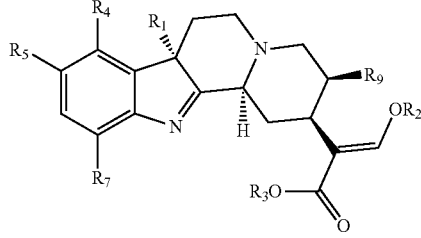

wherein
$R_1$ is —OH;
$R_2$ and $R_3$ are each, independently, —H or —$CH_3$;
$R_4$ is —$OCH_3$;
$R_5$ and $R_7$ are each, independently, —F, —Cl, —Br, —I, —CN, —$CF_3$, —$NO_2$, —OH, —$CH_3$, —$OCH_3$, —C(O) $NH_2$ or phenyl; and
$R_9$ is —$CH_3$, —$CH_2CH_3$, —$CH_2CH_2CH_3$, —CH=$CH_2$, —$CH_3CH$=$CH_2$, —$CH_2OH$, —$CH_2$-cyclopropyl, —$CH_2$-cyclobutyl or —$CH_2CH_2$-phenyl, or a pharmaceutically acceptable salt or ester thereof.

In some embodiments, the compound wherein $R_2$ and $R_3$ are each —$CH_3$.

In some embodiments, the compound wherein $R_4$ is —$OCH_3$.

In some embodiments, the compound having the structure:

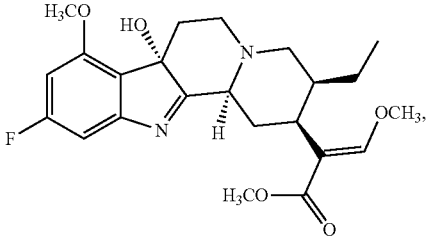

-continued

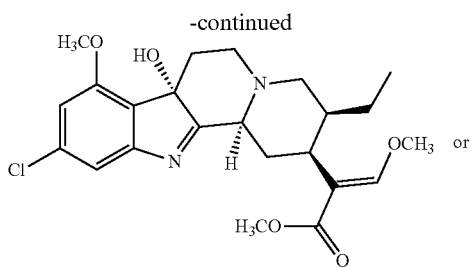

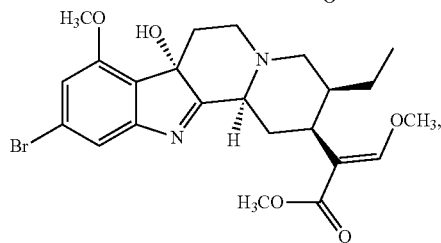

or a pharmaceutically acceptable salt or ester thereof.

In some embodiments, the compound having the structure:

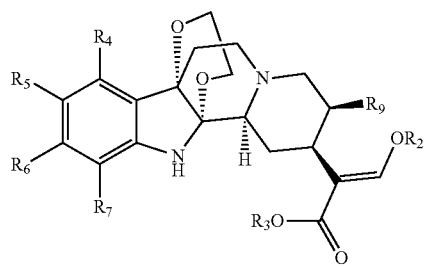

wherein $R_2$ and $R_3$ are each, independently, —H or -alkyl;

$R_4$ is —H, —OH, -alkyl or —O-alkyl;

$R_5$, $R_6$ and $R_7$ are each, independently, —H, —F, —Cl, —Br, —I, —CN, —CF$_3$, —NO$_2$, —OH, —NH$_2$, —C(O)NH$_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl;

$R_9$ is alkyl, alkenyl, alkyl-OH, alkyl-O-alkyl, cycloalkyl, alkyl-cycloalkyl, alkyl-aryl or alkyl-heteroaryl, wherein when $R_9$ is ethyl, then $R_6$ is other than H or at least two of $R_5$, $R_6$ and $R_7$ are other than H, and or a pharmaceutically acceptable salt or ester thereof.

In some embodiments, the compound wherein $R_6$ is other than H or at least two of $R_5$, $R_6$ and $R_7$ is other than H; and $R_9$ is alkyl, alkenyl, alkyl-OH, alkyl-O-alkyl, cycloalkyl, alkyl-cycloalkyl, alkyl-aryl or alkyl-heteroaryl.

In some embodiments, the compound wherein $R_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl.

In some embodiments, the compound wherein $R_5$, $R_6$ and $R_7$ are each H; and $R_9$ is $C_1$-alkyl, $C_3$-$C_{12}$ alkyl, alkenyl, alkyl-OH, alkyl-O-alkyl, cycloalkyl, alkyl-cycloalkyl, alkyl-aryl or alkyl-heteroaryl.

In some embodiments, the compound wherein $R_9$ is —CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl.

In some embodiments, the compound wherein $R_5$ and $R_7$ are each H and $R_6$ is other than H.

In some embodiments, the compound having the structure:

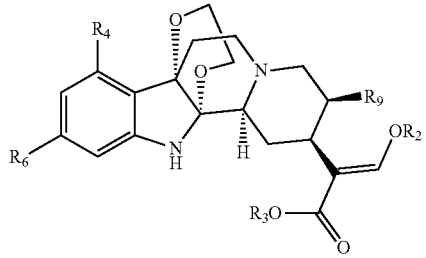

wherein $R_2$ and $R_3$ are each, independently, —H or —CH$_3$;

$R_4$ is —OCH$_3$;

$R_6$ is —F, —Cl, —Br, —I, —CN, —CF$_3$, —NO$_2$, —OH, —CH$_3$, —OCH$_3$, —C(O)NH$_2$ or phenyl; and $R_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein $R_5$ and $R_6$ are each other than H and $R_7$ is H.

In some embodiments, the compound having the structure:

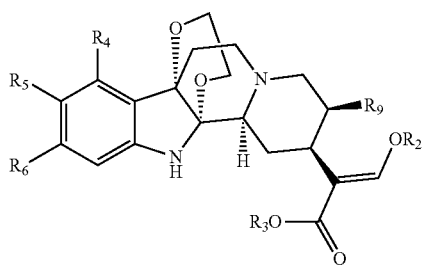

wherein $R_2$ and $R_3$ are each, independently, —H or —CH$_3$;

$R_4$ is —OCH$_3$;

$R_5$ and $R_6$ are each, independently, —F, —Cl, —Br, —I, —CN, —CF$_3$, —NO$_2$, —OH, —CH$_3$, —OCH$_3$, —C(O)NH$_2$ or phenyl; and $R_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein $R_6$ and $R_7$ are each other than H and $R_5$ is H.

In some embodiments, the compound having the structure:

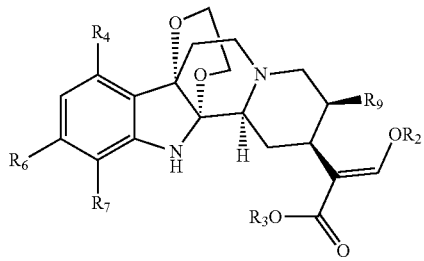

wherein

R$_2$, R$_3$ and R$_4$ are each, independently, —H or —CH$_3$;

R$_2$ and R$_3$ are each, independently, —H or —CH$_3$;

R$_4$ is —OCH$_3$;

R$_6$ and R$_7$ are each, independently, —F, —Cl, —Br, —I, —CN, —CF$_3$, —NO$_2$, —OH, —CH$_3$, —OCH$_3$, —C(O)NH$_2$ or phenyl; and R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein R$_3$ and R$_7$ are each other than H and R$_6$ is H.

In some embodiments, the compound having the structure:

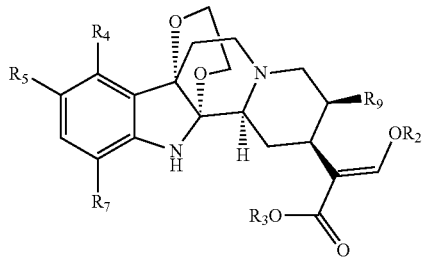

wherein

R$_2$ and R$_3$ are each, independently, —H or —CH$_3$;

R$_4$ is —OCH$_3$;

R$_5$ and R$_7$ are each, independently, —F, —Cl, —Br, —I, —CN, —CF$_3$, —NO$_2$, —OH, —CH$_3$, —OCH$_3$, —C(O)NH$_2$ or phenyl; and R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt or ester thereof.

In some embodiments, the compound wherein R$_2$ and R$_3$ are each —CH$_3$.

In some embodiments, the compound wherein R$_4$ is —OCH$_3$.

In some embodiments, the compound having the structure:

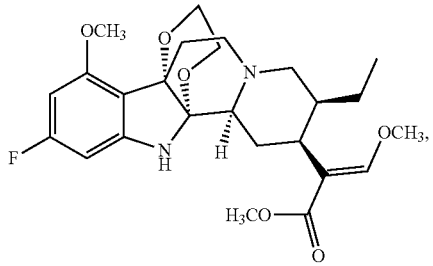

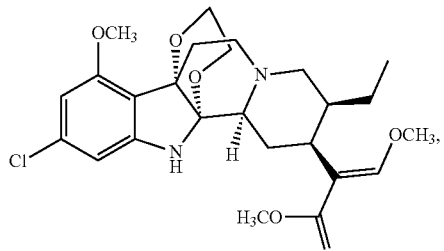

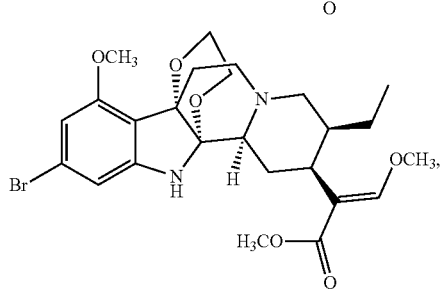

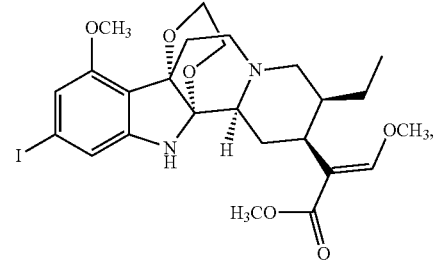

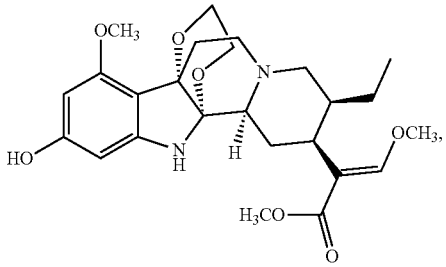

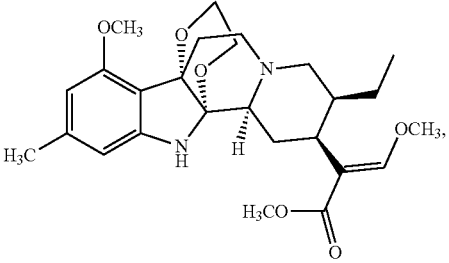

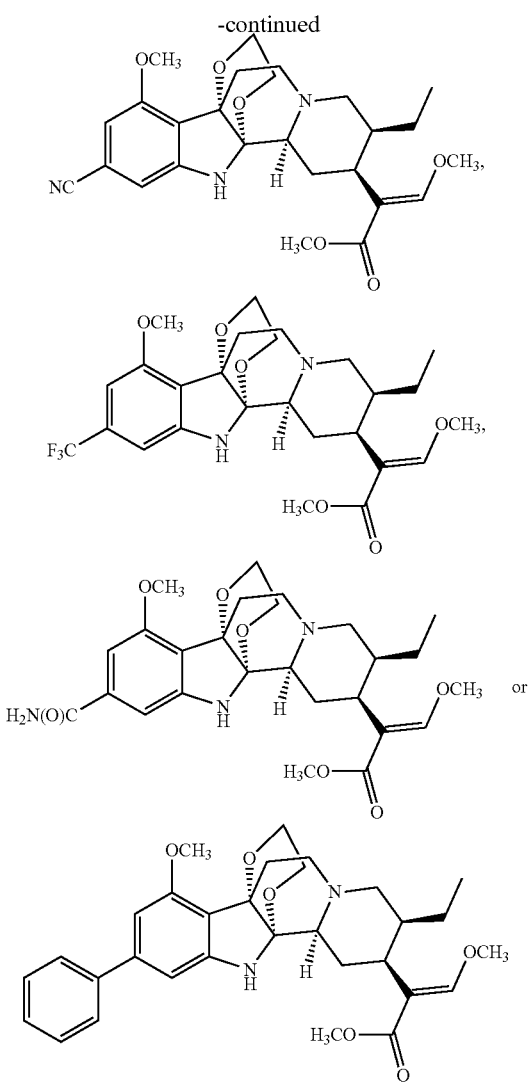

or a pharmaceutically acceptable salt or ester thereof.

In some embodiments, the compound having the structure:

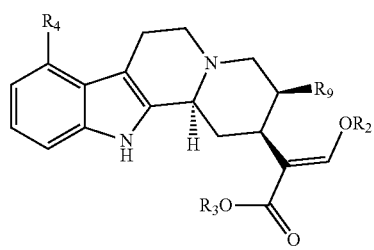

$R_2$ and $R_3$ are each, independently, —H or -alkyl;
$R_4$ is —H, —OH, -alkyl or —O-alkyl; and
$R_9$ is $C_1$-alkyl, $C_3$-$C_{12}$ alkyl, $C_3$-$C_{12}$ alkenyl, alkyl-OH, alkyl-O-alkyl, cycloalkyl, alkyl-cycloalkyl, alkyl-aryl or alkyl-heteroaryl,
or a pharmaceutically acceptable salt or ester thereof.

In some embodiments, the compound wherein $R_9$ is —$CH_3$, —$CH_2CH_2CH_3$, —$CH_3CH$=$CH_2$, —$CH_2OH$, —$CH_2$-cyclopropyl, —$CH_2$-cyclobutyl or —$CH_2CH_2$-phenyl.

In some embodiments, the compound having the structure:

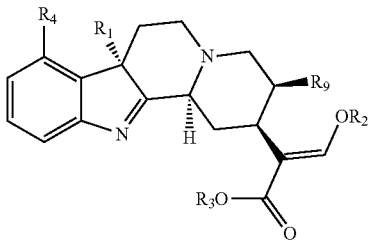

$R_1$ is OH, —O-alkyl, —O(CO)-alkyl;
$R_2$ and $R_3$ are each, independently, —H or -alkyl;
$R_4$ is —H, —OH, -alkyl or —O-alkyl; and
$R_9$ is $C_1$-alkyl, $C_3$-$C_{12}$ alkyl, alkenyl, alkyl-OH, alkyl-O-alkyl, cycloalkyl, alkyl-cycloalkyl, alkyl-aryl or alkyl-heteroaryl, or a pharmaceutically acceptable salt or ester thereof.

In some embodiments, the compound wherein $R_9$ is —$CH_3$, —$CH_2CH_2CH_3$, —$CH$=$CH_2$, —$CH_3CH$=$CH_2$, —$CH_2OH$, —$CH_2$-cyclopropyl, —$CH_2$-cyclobutyl or —$CH_2CH_2$-phenyl.

In some embodiments, the compound having the structure:

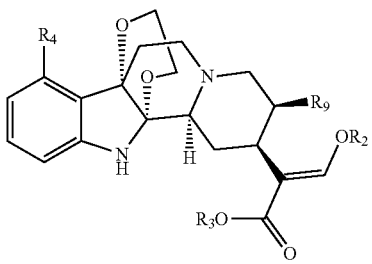

$R_2$ and $R_3$ are each, independently, —H or -alkyl;
$R_4$ is —H, —OH, -alkyl or —O-alkyl; and
$R_9$ is $C_1$-alkyl, $C_3$-$C_{12}$ alkyl, alkenyl, alkyl-OH, alkyl-O-alkyl, cycloalkyl, alkyl-cycloalkyl, alkyl-aryl or alkyl-heteroaryl,
or a pharmaceutically acceptable salt or ester thereof In some embodiments, the compound wherein $R_9$ is —$CH_3$, —$CH_2CH_2CH_3$, —$CH$=$CH_2$, —$CH_3CH$=$CH_2$, —$CH_2OH$, —$CH_2$-cyclopropyl. —$CH_2$-cyclobutyl or —$CH_2CH_2$-phenyl.

The present invention also provides a compound having the structure:

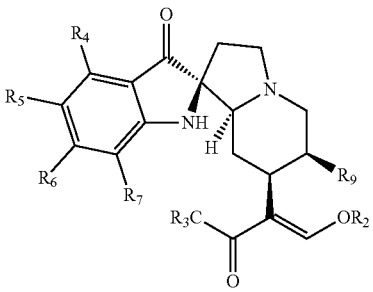

wherein $R_2$ and $R_3$ are each, independently, —H or -alkyl;

$R_4$ is —H, —OH, -alkyl or —O-alkyl;

$R_5$, $R_6$ and are each, independently, —H, —F, —Cl, —Br, —I, CN, $CF_3$, $NO_2$, —OH, —$NH_2$, —C(O)$NH_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl; and $R_9$ is alkyl, alkenyl, alkyl-OH, cycloalkyl, alkyl-cycloalkyl, alkyl-aryl or alkyl-heteroaryl, wherein when $R_9$ is ethyl, then $R_6$ is other than H or at least two of $R_5$, $R_6$ and $R_7$ are other than H, and wherein when $R_2$ and $R_3$ are each —$CH_3$, and $R_4$ is —$OCH_3$, and each of $R_5$, and $R_7$ is —H, $R_9$ is ethyl, then $R_6$ is other than —$OCH_3$, or a pharmaceutically acceptable salt or ester thereof.

In some embodiments, the compound wherein $R_5$ is other than H or at least two of $R_5$, $R_6$ and $R_7$ is other than H; and $R_9$ is alkyl, alkenyl, alkyl-OH, cycloalkyl, alkyl-cycloalkyl, alkyl-aryl or alkyl-heteroaryl.

In some embodiments, the compound wherein $R_9$ is —$CH_3$, —$CH_2CH_3$, —$CH_2CH_2CH_3$, —CH=$CH_2$, —$CH_3$CH=$CH_2$, —$CH_2$OH, —$CH_2$-cyclopropyl, —$CH_2$-cyclobutyl or —$CH_2CH_2$-phenyl.

In some embodiments, the compound wherein $R_5$, $R_6$ and $R_7$ are each H; and $R_9$ is $C_1$-alkyl, $C_3$-$C_{12}$ alkyl, alkenyl, alkyl-OH, alkyl-O-alkyl, cycloalkyl, alkyl-cycloalkyl, alkyl-aryl or alkyl-heteroaryl.

In some embodiments, the compound wherein $R_9$ is —$CH_3$, —$CH_2CH_2CH_3$, —CH=$CH_2$, —$CH_3$CH=$CH_2$, —$CH_2$OH, —$CH_2$-cyclopropyl, —$CH_2$-cyclobutyl or —$CH_2CH_2$-phenyl.

In some embodiments, the compound wherein $R_5$ and $R_7$ are each H and $R_6$ is other than H.

In some embodiments, the compound having the structure:

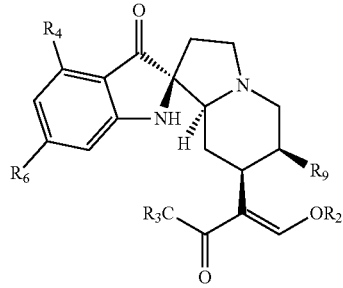

wherein $R_2$ and $R_3$ are each, independently, —H or —$CH_3$;

$R_4$ is —$OCH_3$;

$R_6$ is —F, —Cl, —Br, —I, —CN, —$CF_3$, —$NO_2$, —OH, —$CH_3$, —C(O)$NH_2$ or phenyl; and $R_9$ is —$CH_3$, —$CH_2CH_3$, —$CH_2CH_2CH_3$, —CH=$CH_2$, —$CH_2$OH, $CH_2$-cyclopropyl or —$CH_2CH_2$-phenyl, or a pharmaceutically acceptable salt or ester thereof.

In some embodiments, the compound wherein $R_5$ and $R_6$ are each other than H and $R_7$ is H.

In some embodiments, the compound having the structure:

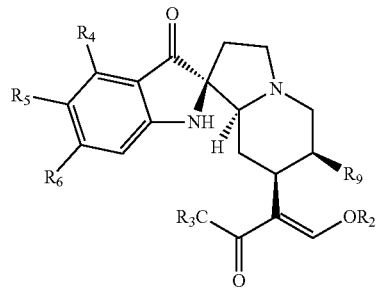

wherein $R_2$ and $R_3$ are each, independently, —H or —$CH_3$;

$R_4$ is —$OCH_3$;

$R_5$ and $R_6$ are each, independently, —F, —Cl, —Br, —I, —CN, —$CF_3$, —$NO_2$, —OH, —$CH_3$, —$OCH_3$, —C(O)$NH_2$ or phenyl; and $R_9$ is —$CH_3$, —$CH_2CH_3$, —$CH_2CH_2CH_3$, —CH=$CH_2$, —$CH_3$CH=$CH_2$, —$CH_2$OH, —$CH_2$-cyclopropyl, —$CH_2$-cyclobutyl or —$CH_2CH_2$-phenyl, or a pharmaceutically acceptable salt or ester thereof.

In some embodiments, the compound wherein $R_6$ and $R_7$ are each other than H and $R_5$ is H.

In some embodiments, the compound having the structure:

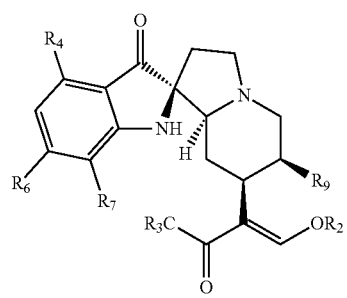

wherein $R_2$ and $R_3$ are each, independently, —H or —$CH_3$;

$R_4$ is —$OCH_3$;

$R_6$ and $R_7$ are each, independently, —F, —Cl, —Br, —I, —CN, —$CF_3$, —$NO_2$, —OH, —$CH_3$, —$OCH_3$, —C(O)$NH_2$ or phenyl; and $R_9$ is —$CH_3$, —$CH_2CH_3$, —$CH_2CH_2CH_3$, —CH=$CH_2$, —$CH_3$CH=$CH_2$, —$CH_2$OH, —$CH_2$-cyclopropyl, —$CH_2$-cyclobutyl or —$CH_2CH_2$-phenyl, or a pharmaceutically acceptable salt or ester thereof.

In some embodiments, the compound wherein $R_5$ and $R_7$ are each other than H and $R_6$ is H.

In some embodiments, the compound having the structure:

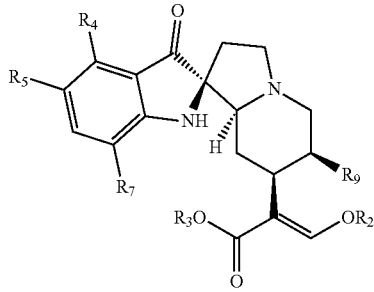

wherein
$R_2$ and $R_3$ are each, independently, —H or —$CH_3$;
$R_4$ is —$OCH_3$;
$R_5$ and $R_7$ are each, independently, —F, —Cl, —Br, —I, —CN, —$CF_3$, —$NO_2$, —OH, —$CH_3$, —$OCH_3$, —C(O)$NH_2$ or phenyl; and
$R_9$ is —$CH_3$, —$CH_2CH_3$, —$CH_2CH_2CH_3$, —CH=$CH_2$, —$CH_3$CH=$CH_2$, —$CH_2$OH, —$CH_2$-cyclopropyl, —$CH_2$-cyclobutyl or —$CH_2CH_2$-phenyl,
or a pharmaceutically acceptable salt or ester thereof.

In some embodiments, the compound wherein $R_2$ and $R_3$ are each —$CH_3$.

In some embodiments, the compound wherein $R_4$ is —$OCH_3$.

In some embodiments, the compound having the structure:

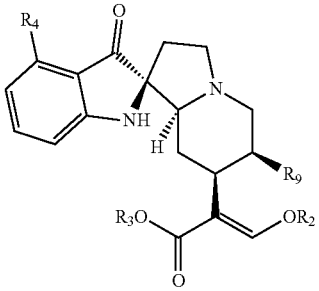

$R_2$, $R_3$ and $R_4$ are each, independently, —H or -alkyl; and
$R_9$ is $C_1$-alkyl, $C_3$-$C_{12}$ alkyl, alkenyl, alkyl-OH, alkyl-O-alkyl, cycloalkyl, alkyl-cycloalkyl, alkyl-aryl or alkyl-heteroaryl,
or a pharmaceutically acceptable salt or ester thereof In some embodiments, the compound wherein $R_9$ is —$CH_3$, —$CH_2CH_2CH_3$, CH=$CH_2$, —$CH_3$CH=$CH_2$, —$CH_2$OH, —$CH_2$-cyclopropyl, —$CH_2$-cyclobutyl or —$CH_2CH_2$-phenyl.

The present invention also provides a compound having the structure:

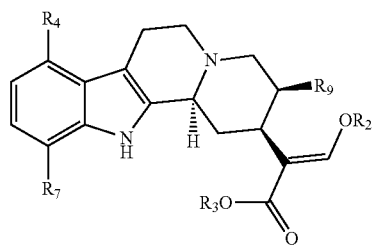

wherein
$R_2$ and $R_3$ are each, independently, —H or -alkyl;
$R_4$ is —H, —OH, -alkyl or —O-alkyl;
$R_7$ is —F, —Cl, —Br, —I, —CN, —$CF_3$, —$NO_2$, —OH, —$NH_2$, —C(O)$NH_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl; and
$R_9$ is alkyl, alkenyl, alkyl-OH, alkyl-O-alkyl, cycloalkyl, alkyl-cycloalkyl, alkyl-aryl or alkyl-heteroaryl,
wherein when $R_2$ and $R_3$ are each H, $R_4$ is —$OCH_3$ and $R_9$ is ethyl, then $R_7$ is other than Br or furanyl,
or a pharmaceutically acceptable salt or ester thereof.

The present invention also provides a compound having the structure:

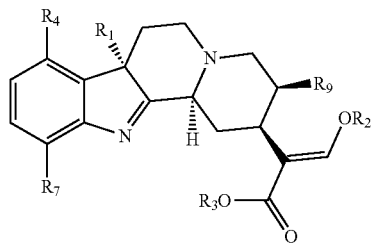

Wherein
$R_1$ is —OH, —O-alkyl or —O(CO)-alkyl;
$R_2$ and $R_3$ are each, independently, —H or -alkyl;
$R_4$ is —H, —OH, -alkyl or —O-alkyl;
$R_7$ is —F, —Cl, —Br, —I, —CN, —$CF_3$, —$NO_2$, —OH, —$NH_2$, —C(O)$NH_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl; and
$R_9$ is alkyl, alkenyl, alkyl-OH, alkyl-O-alkyl, cycloalkyl, alkyl-cycloalkyl, alkyl-aryl or alkyl-heteroaryl,
or a pharmaceutically acceptable salt or ester thereof.

The present invention also provides a compound having the structure:

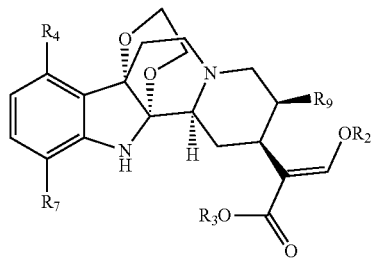

wherein
$R_2$ and $R_3$ are each, independently, —H or -alkyl;
$R_4$ is —H, —OH, -alkyl or —O-alkyl;
$R_7$ is —F, —Cl, —Br, —I, —CN, —$CF_3$, —$NO_2$, —OH, —$NH_2$, —C(O)$NH_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl; and
$R_9$ is alkyl, alkenyl, alkyl-OH, alkyl-O-alkyl, cycloalkyl, alkyl-cycloalkyl, alkyl-aryl or alkyl-heteroaryl,
or a pharmaceutically acceptable salt or ester thereof.

The present invention also provides a compound having the structure:

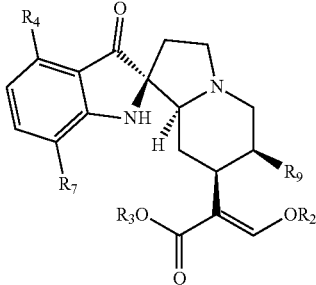

wherein

R$_2$ and R$_3$ are each, independently, —H or -alkyl;

R$_4$ is —H, —OH, -alkyl or —O-alkyl;

R$_7$ is —F, —Cl, —Br, —I, —CN, —CF$_3$, —NO$_2$, —OH, —NH$_2$, —C(O)NH$_2$, —NH(CO)-alkyl, —NH(CO)NH-alkyl, —NH(CO)-aryl, —NH(CO)NH-aryl, —O-alkyl, —O-aryl, —O-heteroaryl, alkyl, aryl or heteroaryl; and R$_9$ is alkyl, alkenyl, alkyl-OH, alkyl-O-alkyl, cycloalkyl, alkyl-cycloalkyl, alkyl-aryl or alkyl-heteroaryl, wherein when R$_2$ and R$_3$ are each H, R$_4$ is —OCH$_3$ and R$_9$ is ethyl, then R$_7$ is other than furanyl, or a pharmaceutically acceptable salt or ester thereof.

In some embodiments, the compound having the structure:

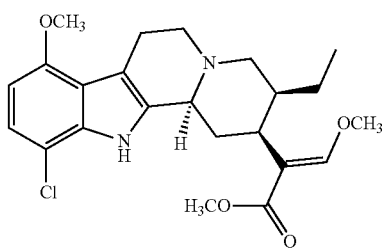

or

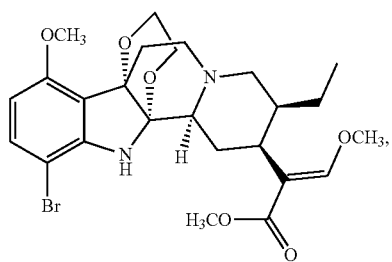

or a pharmaceutically acceptable salt or ester thereof.

In some embodiments, the compound having the structure:

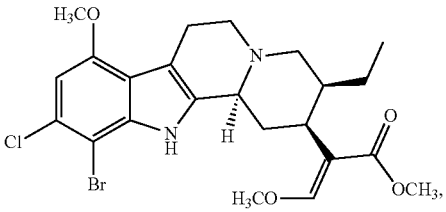 [SMILES: CC[C@@H]1CN2CCc3c([nH]c4c(Br)c(Cl)cc(OC)c34)[C@@H]2C[C@@H]1/C(=C\OC)C(=O)OC]

or a pharmaceutically acceptable salt or ester thereof.

In some embodiments, the compound having the structure:

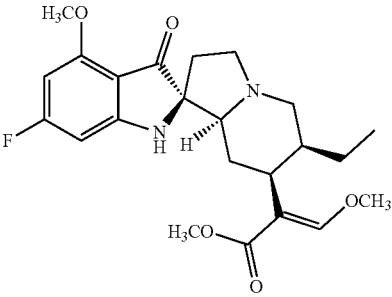

or a pharmaceutically acceptable salt or ester thereof.

In some embodiments, the compound having the structure:

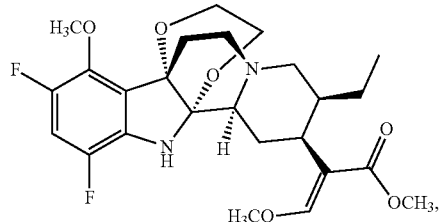

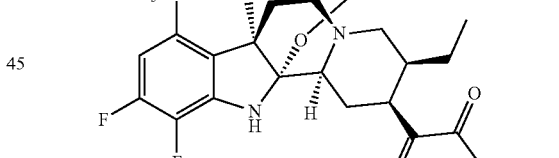 or

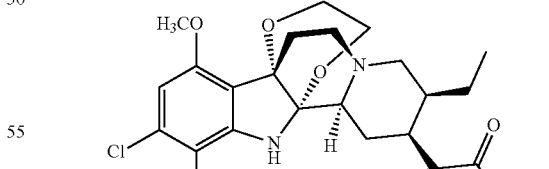

or a pharmaceutically acceptable salt or ester thereof.

The present invention also provides a pharmaceutical composition comprising the compound of the present invention and a pharmaceutically acceptable carrier.

In some embodiments, a method of activating a mu-opioid receptor comprising contacting the mu-opioid receptor with the compound or the composition of the present invention; or of antagonizing a mu-opioid receptor, a delta-opioid receptor and/or a kappa-opioid receptor comprising contacting the mu-opioid receptor, the delta-opioid receptor and/or the kappa-opioid receptor with the compound or the composition of the present invention.

In some embodiments, a method of treating a subject afflicted with pain, a depressive disorder, a mood disorder or an anxiety disorder comprising administering an effective amount of the compound or the composition of the present invention to the subject so as to thereby treat the subject afflicted with pain, the depressive disorder, the mood disorder or the anxiety disorder.

In some embodiments, a method of treating a subject afflicted with pain comprising administering to the subject an effective amount of an NMDA receptor antagonist, an NMDA receptor partial agonist, a neurokinin 1 receptor antagonist, or a delta-opioid receptor agonist and an effective amount of the compound or the composition of the present invention so as to thereby treat the subject afflicted with pain.

In some embodiments, a method of treating a subject afflicted with a depressive disorder, a mood disorder or an anxiety disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a delta-opioid receptor agonist and an effective amount of the compound or the composition of the present invention so as to thereby treat the subject afflicted with the depressive disorder, the mood disorder or the anxiety disorder.

In some embodiments, a method of treating a subject afflicted with borderline personality disorder comprising administering an effective amount of the compound or the composition of the present invention to the subject so as to treat the subject afflicted with the borderline personality disorder.

In some embodiments, a method of treating a subject afflicted with opioid addiction or opioid withdrawal symptoms comprising administering an effective amount of the compound or the composition of the present invention to the subject so as to treat the subject afflicted with the opioid addiction or opioid withdrawal symptoms.

In some embodiments, a method of treating a subject afflicted with borderline personality disorder comprising administering to the subject an effective amount of an NMDA receptor antagonist, an NMDA receptor partial agonist, a neurokinin 1 receptor antagonist, or a DOR agonist and an effective amount of the compound or the composition of the present invention so as to thereby treat the subject afflicted with borderline personality disorder; or
  of treating a subject afflicted with opioid addiction or opioid withdrawal symptoms comprising administering to the subject an effective amount of an NMDA receptor antagonist, an NMDA receptor partial agonist or a neurokinin 1 receptor antagonist and an effective amount of the compound or the composition of the present invention so as to thereby treat the subject afflicted with the opioid addiction or opioid withdrawal symptoms.

In some embodiments, a method of treating a subject afflicted with opioid addiction or opioid withdrawal symptoms comprising administering to the subject an effective amount of naloxone or methylnaltrexone and an effective amount the compound or the composition of the present invention so as to thereby treat the subject afflicted with the opioid addiction or opioid withdrawal symptoms; or
  of treating a subject afflicted with pain, a depressive disorder, a mood disorder, an anxiety disorder, or borderline personality disorder, comprising administering to the subject an effective amount of naloxone or methylnaltrexone and an effective amount the compound or the composition of the present invention so as to thereby treat the subject afflicted with pain, the depressive disorder, the mood disorder, the anxiety disorder, or borderline personality disorder.

In some embodiments, a method of treating a subject afflicted with a depressive disorder, a mood disorder, an anxiety disorder, or borderline personality disorder, comprising administering to the subject an effective amount of a selective serotonin reuptake inhibitor or a serotonin-norepinephrine reuptake inhibitor and an effective amount of the compound or the composition of the present invention so as to thereby treat the subject afflicted with the depressive disorder, mood disorder, anxiety disorder, or borderline personality disorder.

In some embodiments, a pharmaceutical composition comprising the compound of the present invention, an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone, methylnaltrexone, a selective serotonin reuptake inhibitor or a serotonin-norepinephrine reuptake inhibitor, and a pharmaceutically acceptable carrier.

In some embodiments, a process of making the compound of the present invention substantially as described herein.

In some embodiments, a process for producing the compound having the following structure:

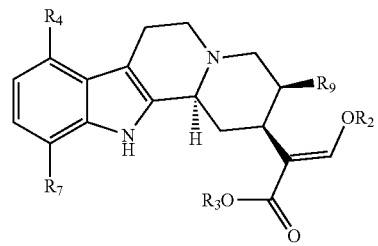

$R_2$ and $R_3$ are each -alkyl;
$R_4$ is —O-alkyl;
$R_7$ is a boronate ester; and
$R_9$ is $C_1$-alkyl, $C_3$-$C_{12}$ alkyl, $C_3$-$C_{12}$ alkenyl, alkyl-OH, alkyl-O-alkyl, cycloalkyl, alkyl-cycloalkyl, alkyl-aryl or alkyl-heteroaryl,
comprising:
(i) contacting the compound having the structure:

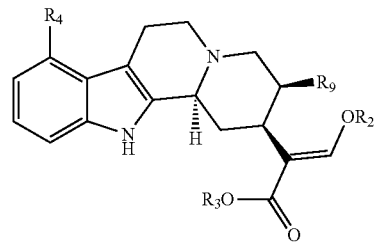

with a borylating agent in the presence of a metal catalyst and ligand to produce the compound.

In some embodiments, a process for producing the compound having the following structure:

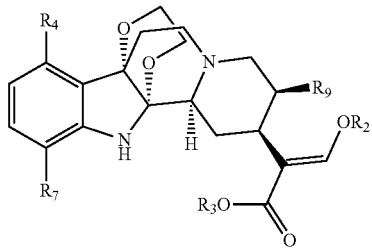

$R_2$ and $R_3$ are each -alkyl;

$R_4$ is —O-alkyl;

$R_7$ is a boronate ester; and $R_9$ is $C_1$-alkyl, $C_3$-$C_{12}$ alkyl, $C_3$-$C_{12}$ alkenyl, alkyl-OH, alkyl-O-alkyl, cycloalkyl, alkyl-cycloalkyl, alkyl-aryl or alkyl-heteroaryl, comprising:

(i) contacting the compound having the structure:

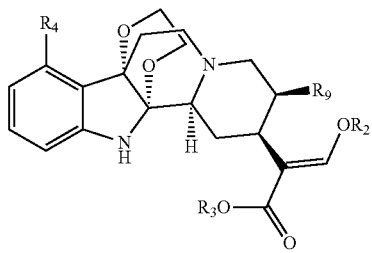

with a borylating agent in the presence of a metal catalyst and ligand to produce the compound.

In some embodiments, a process for producing the compound having the following structure:

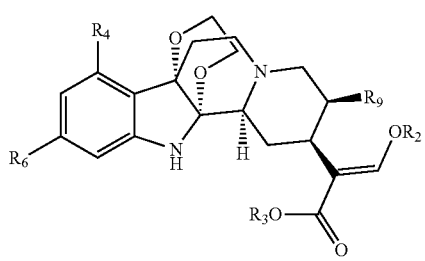

$R_2$ and $R_3$ are each -alkyl;

$R_4$ is —O-alkyl;

$R_6$ is a boronate ester; and $R_9$ is $C_1$-alkyl, $C_3$-$C_{12}$ alkyl, $C_3$-$C_{12}$ alkenyl, alkyl-OH, alkyl-O-alkyl, cycloalkyl, alkyl-cycloalkyl, alkyl-aryl or alkyl-heteroaryl, comprising:

(i) contacting the compound having the structure:

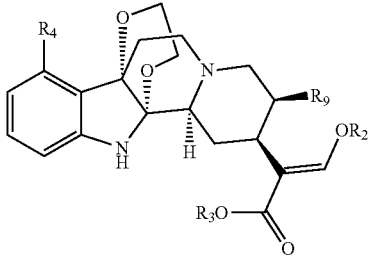

with a borylating agent in the presence of a metal catalyst and ligand to produce the compound.

In one embodiment, $R_1$ is O—($C_{1-5}$ alkyl). In one embodiment, $R_1$ is O—($C_{1-10}$ alkyl). In one embodiment, $R_1$ is O—($C_1$ alkyl). In one embodiment, $R_1$ is —OH.

In one embodiment, $R_1$ is —O(CO)—($C_{1-5}$ alkyl). In one embodiment, $R_1$ is —O(CO)—($C_{1-10}$ alkyl).

In one embodiment, $R_2$ is ($C_{1-5}$ alkyl). In one embodiment, $R_2$ is ($C_{1-10}$ alkyl). In one embodiment, $R_2$ is ($C_1$ alkyl).

In one embodiment, $R_3$ is ($C_{1-5}$ alkyl). In one embodiment, $R_3$ is ($C_{1-10}$ alkyl). In one embodiment, $R_3$ is ($C_1$ alkyl).

In one embodiment, $R_4$ is O($C_1$ alkyl). In one embodiment, $R_4$ is O($C_{1-10}$ alkyl). In one embodiment, $R_4$ is O($C_1$ alkyl).

In some embodiments, the method wherein the subject is afflicted with pain, a depressive disorder, a mood disorder, or an anxiety disorder.

In some embodiments, the anxiety disorder includes, but is not limited to, is anxiety, generalized anxiety disorder (GAD), panic disorder, social phobia, social anxiety disorder, acute stress disorder, obsessive-compulsive disorder (OCD), or post-traumatic stress disorder (PTSD).

In some embodiments, the depressive disorder includes, but is not limited to, depression, major depression, dysthymia, cyclothymia, postpartum depression, seasonal affective disorder, atypical depression, psychotic depression, bipolar disorder, premenstrual dysphoric disorder, situational depression or adjustment disorder with depressed mood. Depressive disorders can also include other mood disorders and is not limited to the above list.

In some embodiments, the NMDA receptor antagonist is an arylcyclohexylamine, dextromorphinan or adamantane.

In some embodiments, the NMDA receptor antagonist is dextromethorphan, dextrorphan, dextrallorphan, memantine, amantadine, rimantadine, nitromemantine (YQW-36), ketamine (and its analogs, e.g. tiletamine), phencyclidine (and its analogs, e.g. tenocyclidine, eticyclidine, rolicyclidine), methoxetamine (and its analogs), gacyclidine (GK-11), neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDG EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A) or AP-7.

In some embodiments, the NMDA receptor partial agonist is NRX-1074 or rapastinel (GLYX-13).

In some embodiments, the neurokinin 1 receptor antagonist is aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888 or GR 82334.

In some embodiments, the neurokinin 2 receptor antagonist is saredutant, ibodutant, nepadutant, GR-159897 or MEN-10376.

In some embodiments, the neurokinin 3 receptor antagonist is osanetant, talnetant, SB-222200 or SB-218795.

In some embodiments, the DOR agonist is tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863 or 7-spiroindanyloxymorphone.

The term "MOR agonist" is intended to mean any compound or substance that activates the mu-opioid receptor (MOR). The agonist may be a partial, full or super agonist.

The term "DOR agonist" is intended to mean any compound or substance that activates the delta-opioid receptor (DOR). The agonist may be a partial, full or super agonist.

The term "KOR agonist" is intended to mean any compound or substance that activates the kappa-opioid receptor (KOR). The agonist may be a partial, full or super agonist.

The term "super agonist" is intended to mean a compound or substance that activates a receptor with a greater maximal response (higher $E_{max}$) than said receptor's primary endogenous ligand.

The term "MOR antagonist" is intended to mean any compound or substance that blocks or dampens activity of the mu-opioid receptor (MOR). In some instances, the MOR antagonist disrupts the interaction and inhibits the function of an agonist or inverse agonist at the MOR. The antagonist may be a competitive, non-competitive, uncompetitive, or silent antagonist.

The term "DOR antagonist" is intended to mean any compound or substance that blocks or dampens activity of the delta-opioid receptor (DOR). In some instances, the DOR antagonist disrupts the interaction and inhibits the function of an agonist or inverse agonist at the DOR.

The antagonist may be a competitive, non-competitive, uncompetitive, or silent antagonist.

The term "KOR antagonist" is intended to mean any compound or substance that blocks or dampens activity of the kappa-opioid receptor (KOR). In some instances, the KOR antagonist disrupts the interaction and inhibits the function of an agonist or inverse agonist at the KOR. The antagonist may be a competitive, non-competitive, uncompetitive, or silent antagonist.

The present invention also provides a compound of the present invention or a salt or ester thereof, for use in treating a subject afflicted with pain, a depressive disorder, an anxiety disorder or a mood disorder.

The present invention further provides a pharmaceutical composition comprising an amount of a compound of the present invention or a salt or ester thereof, for use in treating a subject afflicted with pain, a depressive disorder, an anxiety disorder or a mood disorder.

The present invention also provides a compound of the present invention or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with pain, a depressive disorder, an anxiety disorder or a mood disorder.

The present invention also provides a compound of the present invention or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with pain, a depressive disorder, an anxiety disorder or a mood disorder.

In some embodiments, a package comprising:
  a) a first pharmaceutical composition comprising an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist and a pharmaceutically acceptable carrier;
  b) a second pharmaceutical composition comprising an amount of any compound of the present invention, or a salt or ester thereof; and
  c) instructions for use of the first and second pharmaceutical compositions together to treat a subject afflicted with pain, a depressive disorder, an anxiety disorder or a mood disorder.

In some embodiments, a therapeutic package for dispensing to, or for use in dispensing to, a subject afflicted with pain, a depressive disorder, an anxiety disorder or a mood disorder, which comprises:
  a) one or more unit doses, each such unit dose comprising:
    (i) an amount of any compound of the present invention, or a salt or ester thereof; and
    (ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
    wherein the respective amounts of said compound and said agonist or antagonist in said unit dose are effective, upon concomitant administration to said subject, to treat the subject, and
  (b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

A pharmaceutical composition in unit dosage form, useful in treating a subject afflicted with pain, a depressive disorder, an anxiety disorder or a mood disorder, which comprises:
  (i) an amount of any compound of the present invention, or a salt or ester thereof; and (ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist, wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

In some embodiments of the present method, compound, package, use or pharmaceutical composition, the compound has the structure:

In some embodiments of the above method, wherein the compound activates mu-opioid receptors in the subject.

In some embodiments of the above method, wherein the compound antagonizes mu-opioid receptors, delta-opioid receptors and/or the kappa-opioid receptors in the subject.

In some embodiments of the above method, wherein the compound antagonizes delta-opioids receptors and/or the kappa-opioids receptors and activates mu-opioid receptors in the subject.

In some embodiments of the above method, wherein the subject is afflicted with a depressive disorder. In some embodiments of the above method, wherein the subject is afflicted with a mood disorder. In some embodiments of the above method, wherein the subject is afflicted with an anxiety disorder.

In some embodiments of the above method, the method further comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone, methylnaltrexone, a selective serotonin reuptake inhibitor or a serotonin-norepinephrine reuptake inhibitor.

In some embodiments, a pharmaceutically acceptable salt of any of the above compounds of the present invention.

In some embodiments, a salt of the compound of the present invention is used in any of the above methods, uses, packages or compositions.

In some embodiments, a pharmaceutically acceptable salt of the compound of the present invention is used in any of the above methods, uses, packages or compositions.

In some embodiments, an ester of the compound of the present invention is used in any of the above methods, uses, packages or compositions.

Any of the above compounds may be used in any of the disclosed methods, uses, packages or pharmaceutical compositions.

Any of the compounds used in the disclosed methods, uses, packages or pharmaceutical compositions may be replaced with any other compound disclosed in the present invention.

Any of the above generic compounds may be used in any of the disclosed methods, uses, packages or compositions.

Except where otherwise specified, the structure of a compound of this invention includes an asymmetric carbon atom, it is understood that the compound occurs as a racemate, racemic mixture, a scalemic mixture and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$ or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$ (D), or $^3H$ (T). Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

Deuterium (2H or D) is a stable, non-radioactive isotope of hydrogen and has an atomic weight of 2.0144. Hydrogen atom in a compound naturally occurs as a mixture of the isotopes 10 (hydrogen or protium), D (2H or deuterium), and T (30 or tritium). The natural abundance of deuterium is 0.0156%. Thus, a compound with a level of deuterium at any site of hydrogen atom in the compound that has been enriched to be greater than its natural abundance of 0.0156%, is novel over its non-enriched counterpart.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_6$ hydroxyalkyl. $C_1$-$C_n$ as in "$C_1$-$C_n$ alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein a hydrogen contained therein is replaced by a bond to an —OH group.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to atoms with each ring being independently unsubstituted or substituted. Examples of such non-aromatic bicycle elements include but are not limited to: decahydronaphthalene. Examples of such, aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The term "ester" is intended to a mean an organic compound containing the R—O—CO—R' group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5th Edition (1996), March's Advanced Organic Chemistry: Reactions, Mechanisms, and Structure, Michael B. Smith, Jerry March, (Wiley-Interscience) 5th Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reactions and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols; alkali or organic salts of acidic residues such as carboxylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkali metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition. (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid-dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Material and Methods
BRET:
HEK-293T cells were obtained from the American Type Culture Collection (Rockville, MD) and were cultured in a 5% $CO_2$ atmosphere at 37° C. in Dulbecco's Modified Eagle Medium (high glucose ((11965; Life Technologies Corp.; Grand Island, NY) supplemented with 10% FBS (Premium Select, Atlanta Biologicals; Atlanta, GA) and 100 U/mL penicillin and 100 µg/mL streptomycin (415140, Life Technologies).

Mouse $K_i$ Determination:
IBNtxA and [$^{125}$I]BNtxA were synthesized as previously described (Majumdar, S. et al. 2011; Majumdar, S. et al. 2011; Pickett, J. et al. 2015). Na$^{125}$I was purchased from Perkin-Elmer (Waltham, MA).

DNA Constructs:
The mouse MOR (mMOR), the mouse DOR (mDOR), and the rat KOR (rKOR) were provided by Dr. Lakshmi Devi at Mount Sinai Hospital. The human MOR (hMOR), human DOR (hDOR), human KOR (hKOR), and GRK2 were obtained from the Missouri S&T Resource Center. The human G protein constructs used here have been previously described and were provided by C. Gales or were obtained from the Missouri S&T Resource Center unless otherwise noted (Rives, M.-L. 2012, Negri, A. 2013). The G proteins used included untagged G$\alpha$oB (G$\alpha$oD); G$\alpha$oB with Renilla luciferase 8 (RLuc8) inserted at position 91 (G$\alpha$oB-RLuc8); G$\beta$1 ($\beta$1); untagged G$\gamma$2 ($\gamma$2); G$\gamma$2 which we fused to the full-length mVenus at its N-terminus via the amino acid linker GSAGT (mVenus-$\gamma$2). The plasmids employed in the arrestin recruitment assay, RLuc8-arrestin3-Sp1 and mem-linker-citrine-SH3, were synthesized in-house as previously described (Clayton, C. C. et al. 2014). All constructs were sequence-confirmed prior to use in experiments.

Transfection:
The following cDNA amounts were transfected into HEK-293T cells (5×10$^6$ cells/plate) in 10-cm dishes using polyethylenimine (PET) in a 1:1 ratio (diluted in Opti-MEM, Life Technologies): G protein activation: 2.5 µg MOR/DOR/KOR, 0.125 µg G$\alpha_{oB}$-RLuc8, 6.25 µg $\beta_1$, 6.25 µg mVenus-$\gamma$2; cAMP Inhibition: 1.25 µg MOR/DOR/KOR, 1.25 µg G$\alpha_{oB}$, 1.25 µg $\beta_1$, 1.25 µg $\gamma$2, 10 µg CAMYEL. Cells were maintained in the HEK-293T media described above. After 24 hours the media was changed, and the experiment was performed 24 hours later (48 hours after transfection).

G Protein BRET Protocol:
HEK 293-T transfected cells were dissociated and resuspended in phosphate-buffered saline. Approximately 200,000 cells per well were added to a black-framed, white well 96-well plate (no. 60050; Perkin Elmer; Waltham, MA, USA). Following this, 5 µM solution of the luciferase substrate coelenterazine H was added to each well. After 5 min, ligands were added and the BRET signal was measured at 5 min on a PHERAstar FS plate reader (BMG Labtech, Cary, NC, USA). The BRET signal was calculated as the ratio of the light emitted by the energy acceptor, mVenus (510-540 nm), over the light emitted by the energy donor, RLuc8 (485 nm). After agonist stimulation, a decrease of the BRET signal was measured, which reflected a change of conformation or dissociation between the different subunits of the G protein. This drug-induced BRET signal was transformed (multiplied by −1) and normalized using the Emax of the full agonists DAMGO (MOR), DPDPE (DOR) or U-50,488 (KOR), which was defined as the 100% maximal response for G-protein activation. Assays were repeated twice at hMOR, hDOR, and hKOR and data represent normalized mean±s.e.m. of those independent trials.

CAMYEL (Camp) Protocol:
Transfected cells were dissociated and re-suspended in phosphate-buffered saline (PBS). Approximately 200,000 cells/well were added to a black-framed, white well 96-well plate (#60050; Perkin Elmer; Waltham, MA). The microplate was centrifuged and the cells were re-suspended in PBS. Cells were first incubated with forskolin (1 μM) for 5 minutes prior to coelenteratzine H addition. Coelenterazine H (5 μM) was then added to each well for 5 minutes. Following coelenterazine H incubation, a fixed concentration of the reference agonist (5×EC$_{50}$) was added, and the BRET signal was measured at 30 minutes on a PHERAstar FS plate reader. The BRET signal was quantified by calculating the ratio of the light emitted by the energy acceptor, mVenus (510-540 nm) or citrine (510-540 nm), over the light emitted by the energy donor, RLuc8 (485 nm). This drug-induced BRET signal was normalized using the E$_{max}$ of [D-Ala$^2$, N-Me-Phe$^4$, Gly-ol$^5$]-enkephalin (DAMGO), [D-Pen(2,5)]enkephalin (DPDPE), or U-50,488 as the maximal response at MOR, DOR, and KOR respectively. Dose response curves were fit using a three-parameter logistic equation in GraphPad Prism 6. Assay of 7-OH series compounds was repeated three times at mMOR.

Radioligand Competition Binding Assays:

Radioligand Competition Binding Assays with Mouse Receptors. [$^{125}$I]BNtxA binding was carried out in membranes prepared from Chinese Hamster Ovary (CHO) cells stably expressing murine clones of MOR, DOR, and KOR, as previously described (Majumdar, S. et al. 2011, Pickett, J. E. et al. 2015 and Pan, Y. et al. 1999). Assays were performed at 25° C. for 90 min in 50 mM potassium phosphate buffer, pH 7.4, containing 5 mM magnesium sulfate. After the incubation, the reaction was filtered through glass-fiber filters (Whatman Schleicher & Schuell, Keene, NH) and washed three times with 3 mL of ice-cold 50 mM Tris-HCl, pH 7.4, on a semiautomatic cell harvester. Nonspecific binding was defined by addition of levallorphan (8 μM) to matching samples and was subtracted from total binding to yield specific binding. Ki values were calculated by nonlinear regression analysis (GraphPad Prism, San Diego, CA). Protein concentrations were determined using the Lowry method with BSA as the standard (Lowry, 0. H. et al. 1951).

Example 1. Synthesis

Through a regio-selective, iridium catalyzed C—H borylation, selective C—H functionalization was accomplished at the C12 position to provide the C12 boronate ester 12a. This was followed by substitution or cross-coupling reactions from the boronate ester to obtain the resulting C12-chloro (69) and C12-bromo (70) analogues of mitragynine in good yields (Scheme 1).

Although the iridium catalyzed C—H borylation is known to preferentially borylate 2,3-substituted indoles in the 7-position (Paul, S. et al. 2006; Antropow, A. H. et al. 2018; Leitch, J. A. et al. 2017), it is difficult to predict the efficiency and selectivity of this chemical process, as well as other C—H functionalization reactions, in complex compounds such as mitragynine, due to the presence of a number of functional groups. This is the first example that demonstrates that C12 analogs of mitragynine can be accessed in a single borylation step, followed by subsequent boronate substitution to obtain the desired analog.

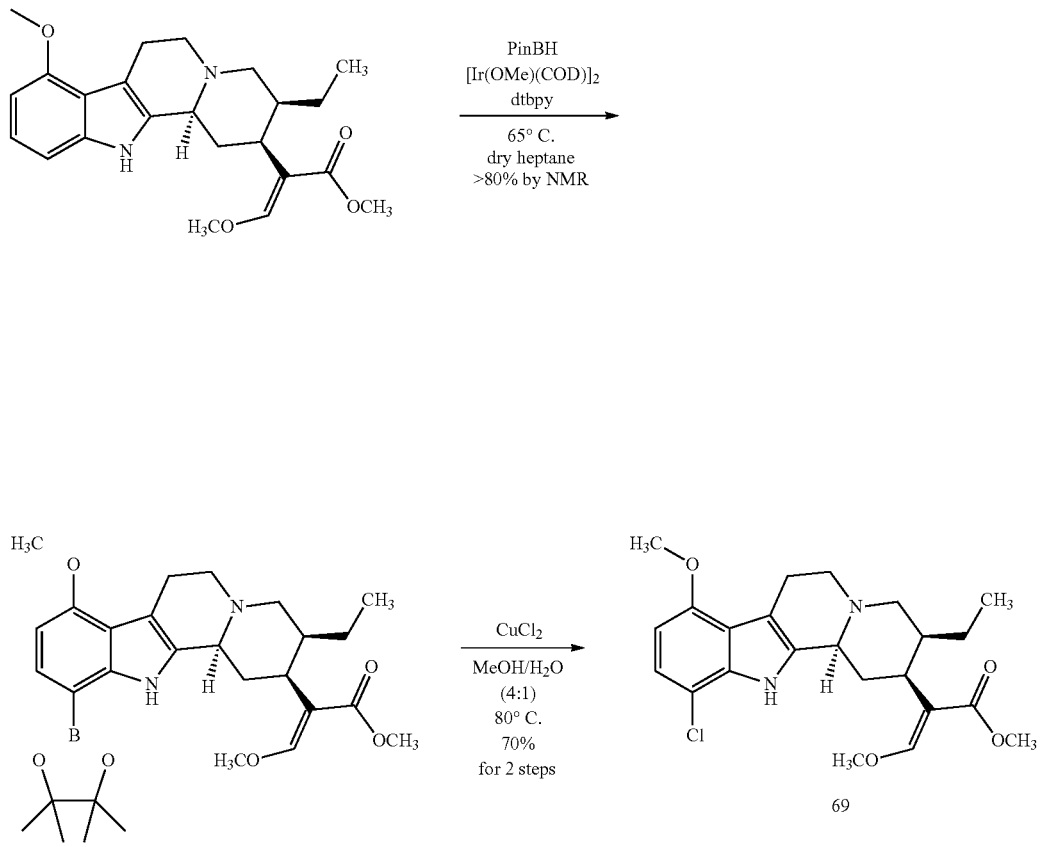

Scheme 1. C12 substitution on mitragynine (12).

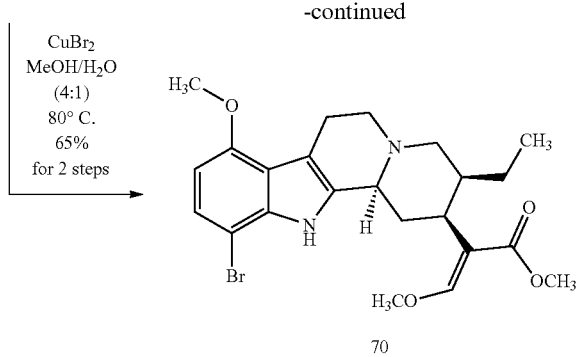

The selective C11 borylation on mitragynine was accomplished by using mitragynine-ethylene glycol adduct 1, where the indole's double bond is temporarily masked by an ethylene glycol group (Scheme 2).

Using the Ir-catalyzed borylation conditions and phenanthroline ligand (ligand needed to be optimized), borylation products 1a and 1b were observed with a 16:1 (1a:1b) product ratio, favoring the C11 position, followed by substitution/oxidation of the boronate ester, to give C11-chloro (3), C11-bromo (4), C11-hydroxy (6) MG-EG (Scheme 2). Thus, the conversion of mitragynine to MG-EG and change of the catalyst's ligand reversed the functionalization selectivity (compared to mitragynine) to favor the C11 functionalization with excellent selectivity.

Scheme 2a. Protection of MG 12 to MG-EG 1. Borylation to achieve C11 (1a) and C12 (1b) boronate ester followed by substitution to bromo (4) substituted MG-EG compounds.

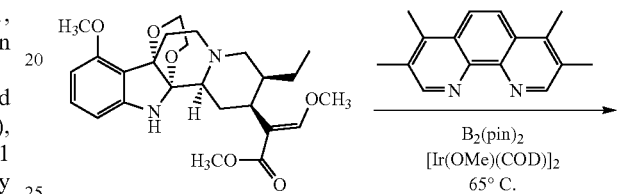

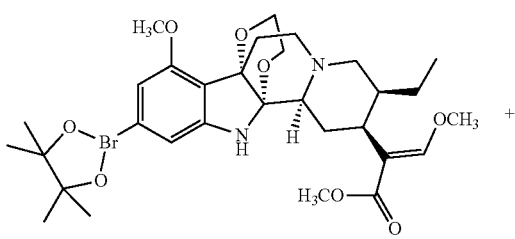

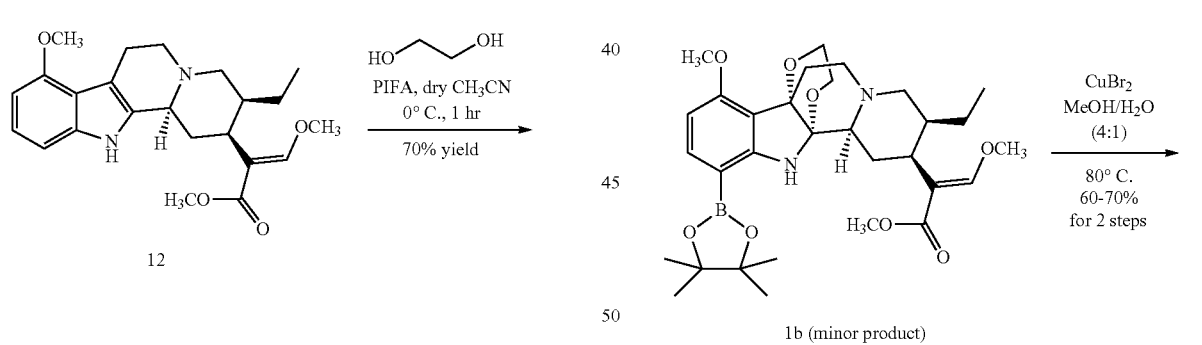

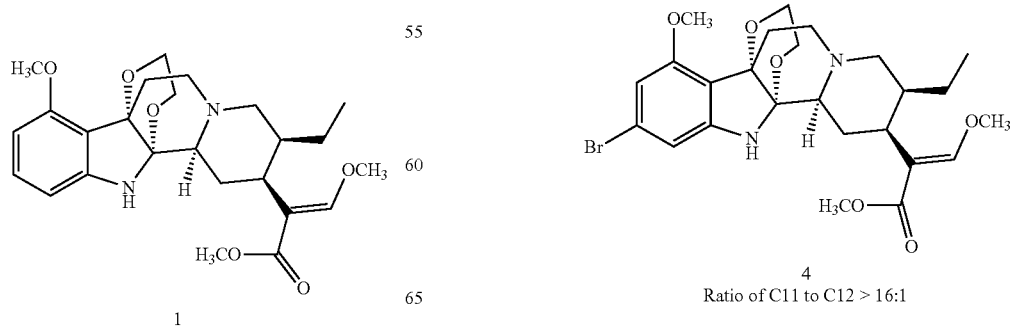

Scheme 2b. Protection of MG 12 to MG-EG 1. Borylation to achieve C11 (1a) and C12 (1b) boronate ester followed by substitution to chloro (3) substituted MG-EG compounds.

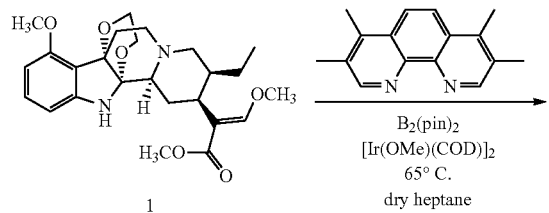

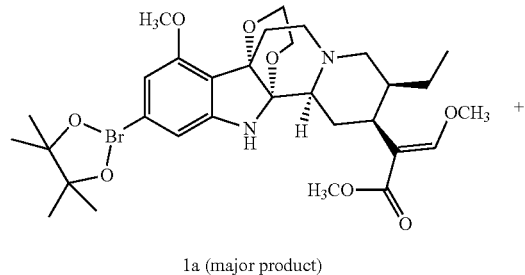

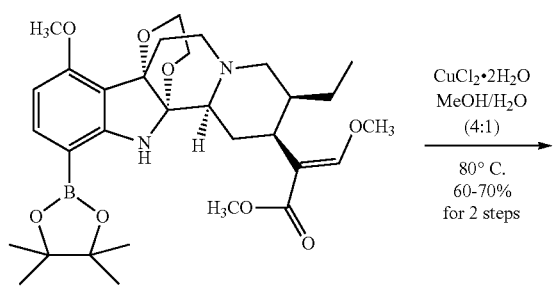

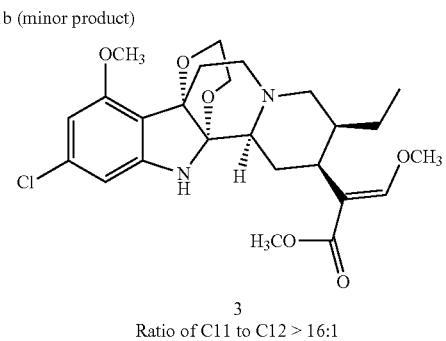

3
Ratio of C11 to C12 > 16:1

Scheme 2c. Protection of MG 12 to MG-EG 1. Borylation to achieve C11 (1a) and C12 (1b) boronate ester followed by substitution to hydroxy (6) substituted MG-EG compounds.

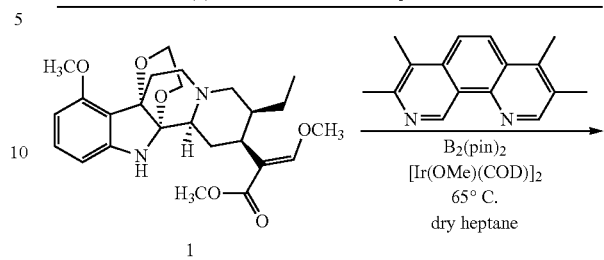

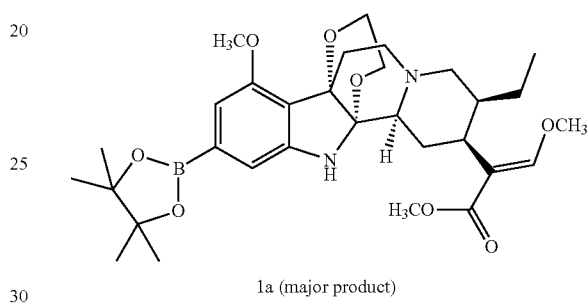

1a (major product)

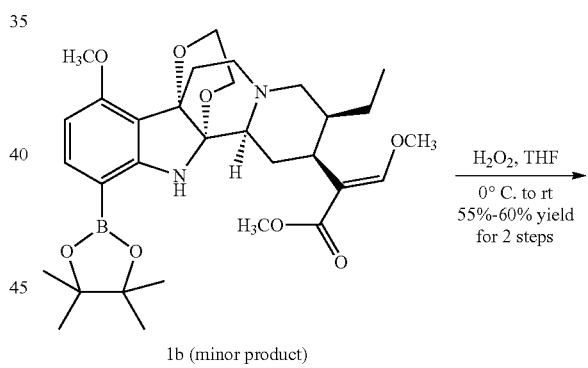

1b (minor product)

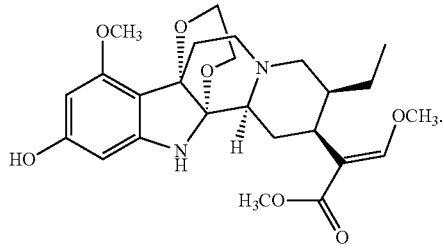

6

The C11 boronate ester 1a and 11-bromo-MG-EG (4) was converted to various 11-substituted EG-protected mitragynine compounds (5, 7, 9, 10, 11, and 19 Scheme 3).

Scheme 3. Synthesis of various 11-substituted MG-EG compounds.
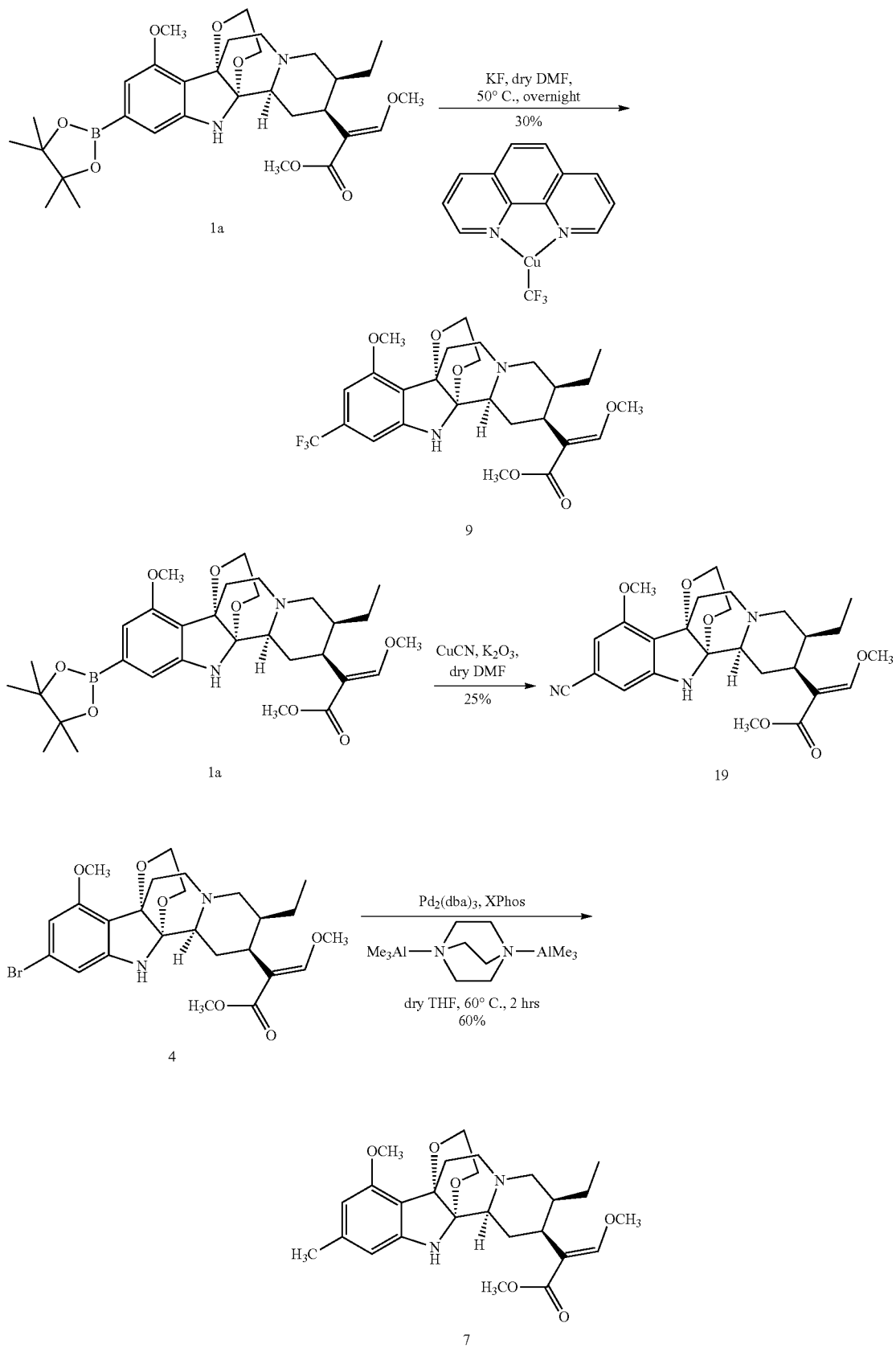

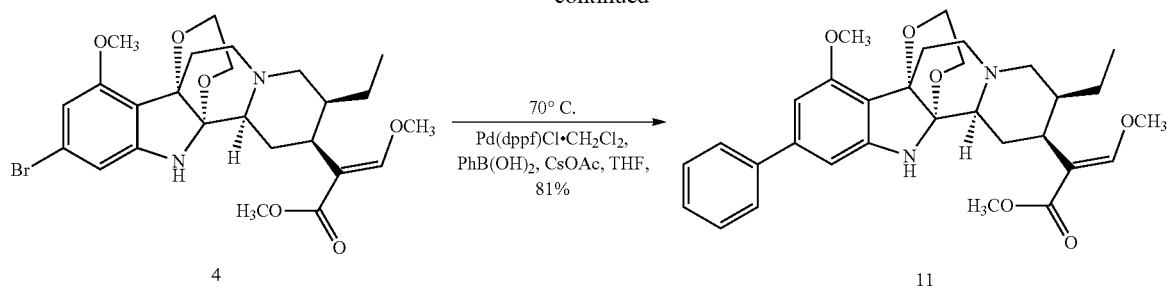
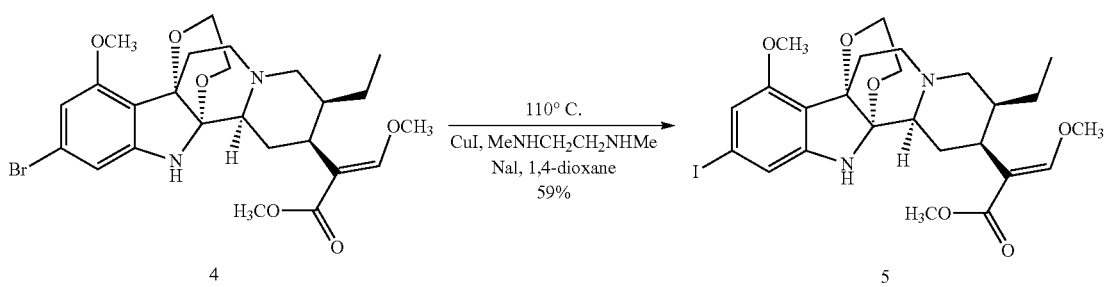
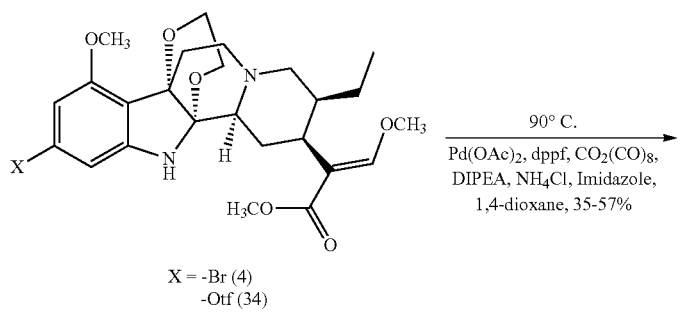
X = -Br (4)
   -Otf (34)
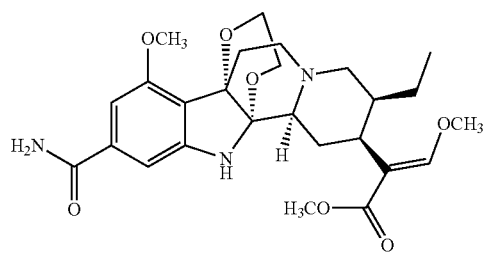
10
The C11 boronate ester was converted to 11-fluoro-MG-EG (2) by two paths (Scheme 4): Path A, the C11 boronate ester 1a was converted to 11-hydroxy-MG-EG (6) followed by a triflation to get (34), stannylation (6b) and fluorination (2); Path B, the C11 boronate ester 1a was converted to 11-bromo-MG-EG (4) followed by stannylation (6b) and fluorination (2).

Scheme 4. Synthesis of 11-fluoro-MG-EG compound.

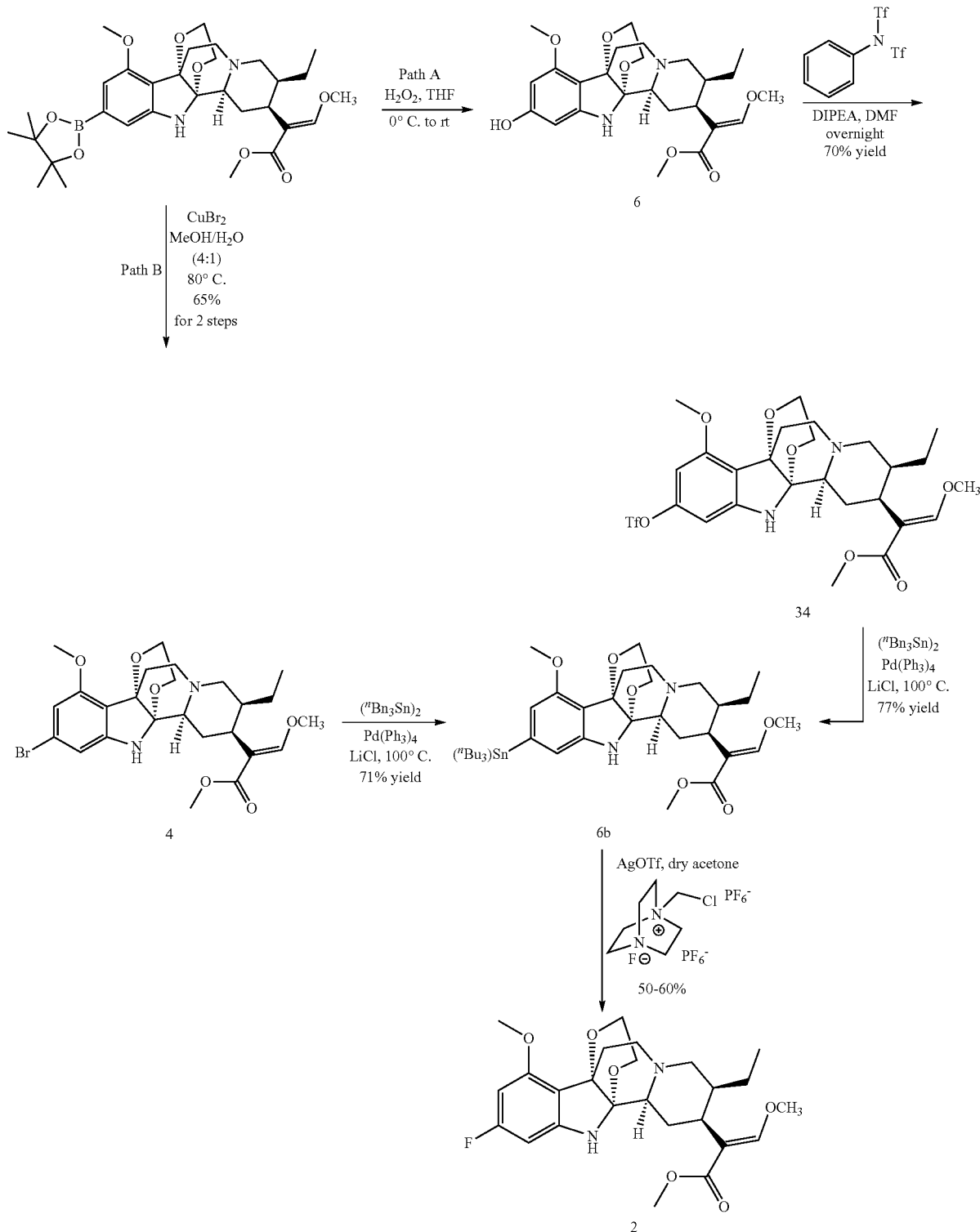

Scheme 5 shows the conversion of 11-substituted MG-EG compounds to the corresponding derivatives of mitragynine (12-22), 7-OH (23-33), and MP (35-45) scaffolds. The deprotection to 12-15 was carried out by a mild reduction. These deprotected mitragynine derivatives (12-15) were then converted to 7-OH analogues (23-26) by oxidation with Oxone. MP (35) was synthesized from 7-OH (23) by a rearrangement employing zinc triflate. Compounds 16-22, 27-33 and 36-45 are prepared by analogous methods.

Scheme 5a. Synthesis of C11 substituted scaffolds of mitragynine.
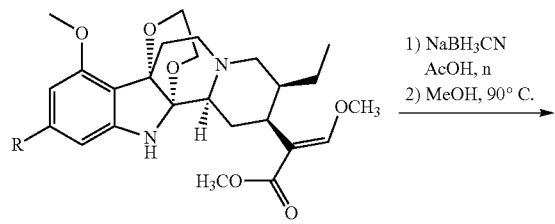
1) NaBH₃CN AcOH, n
2) MeOH, 90° C.
R = H (1)
F (2)
Cl (3)
Br (4)
I (5)
OH (6)
CH₃ (7)
CN (8)
CF₃ (9)
CONH₂ (10)
Phenyl (11)
Scheme 5b. Synthesis of C11 substituted scaffolds of 7-OH.
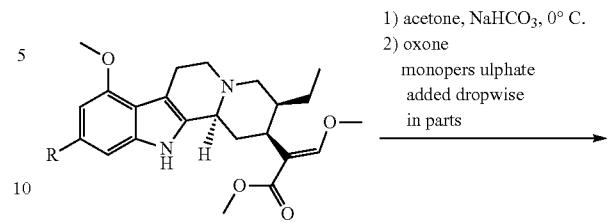
1) acetone, NaHCO₃, 0° C.
2) oxone monopersulphate added dropwise in parts
R = H (12)
F (13)
Cl (14)
Br (15)
I (16)
OH (17)
CH₃ (18)
CN (19)
CF₃ (20)
CONH₂ (21)
Phenyl (22)
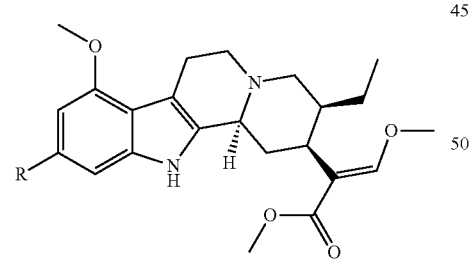
R = H (12) (80%)
F (13) (70%)
Cl (14) (70%)
Br (15) (80%)
I (16)
OH (17)
CH₃ (18)
CN (19)
CF₃ (20)
CONH₂ (21)
Phenyl (22)
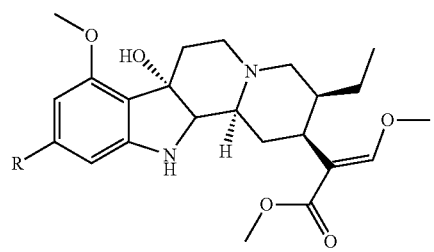
R = H (23) (50%)
F (24) (52%)
Cl (25) (50%)
Br (26) (50%)
I (27)
OH (28)
CH₃ (29)
CN (30)
CF₃ (31)
CONH₂ (32)
Phenyl (33)

Scheme 5c. Synthesis of C11 substituted scaffolds of MP.

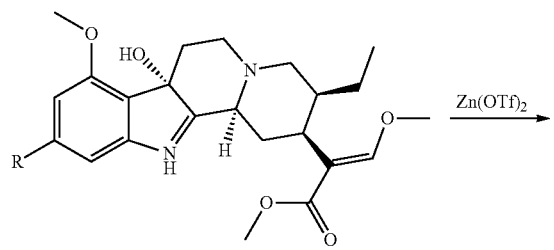

R = H (23)
F (24)
Cl (25)
Br (26)
I (27)
OH (28)
CH₃ (29)
CN (30)
CF₃ (31)
CONH₂ (32)
Phenyl (33)

Zn(OTf)₂ →

R = H (35) (40%)
F (36)
Cl (37)
Br (38)
I (39)
OH (40)
CH₃ (41)
CN (42)
CF₃ (43)
CONH₂ (44)
Phenyl (45)

Scheme 6a. Synthesis of 12-substituted MG-EG compounds.

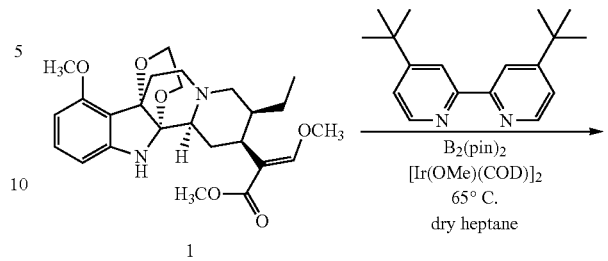

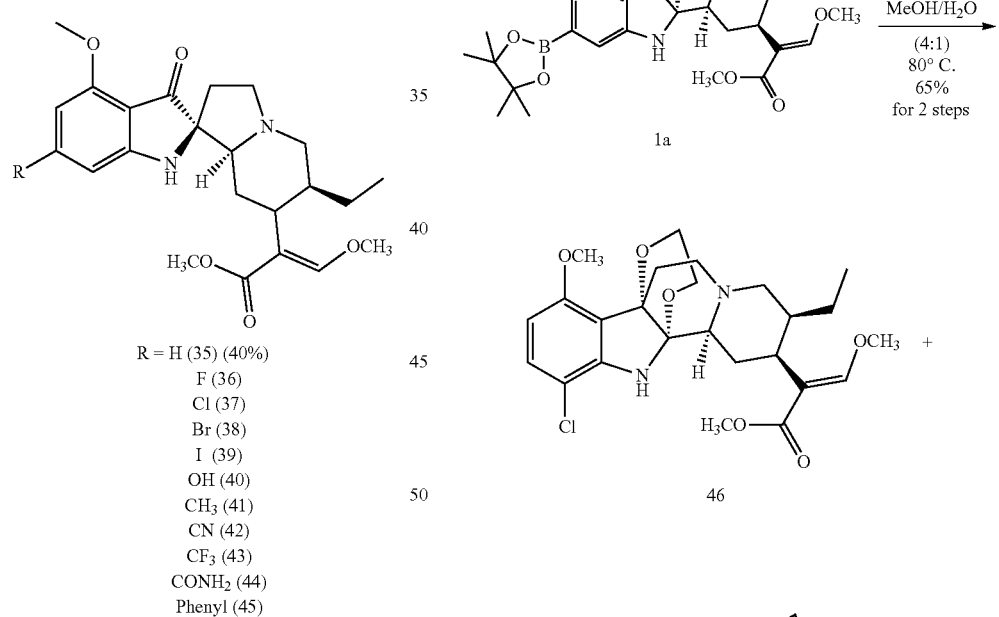

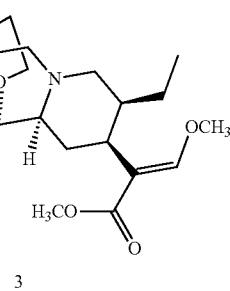

Ratio of C11 to C12 = 1:1

Using the Ir-catalyzed borylation conditions and bipyridyl ligand, borylation (1a and 1b) was observed with 1:1 selectivity. Borylation was followed by substitution to procure C11 and C12 substituted analogues. The C12 chloro (46), bromo (47) MG-EG analogs were thus also synthesized using this alternative sequence (Scheme 6a).

12-fluoro-MG-EG (53) is synthesized using the same procedure as shown in Scheme 4 from the corresponding boronate, or alternatively by an electrophilic aromatic substitution from 1 (Scheme 6b).

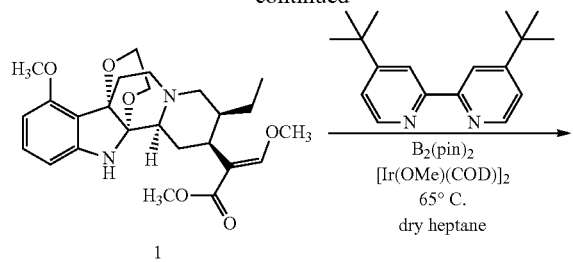
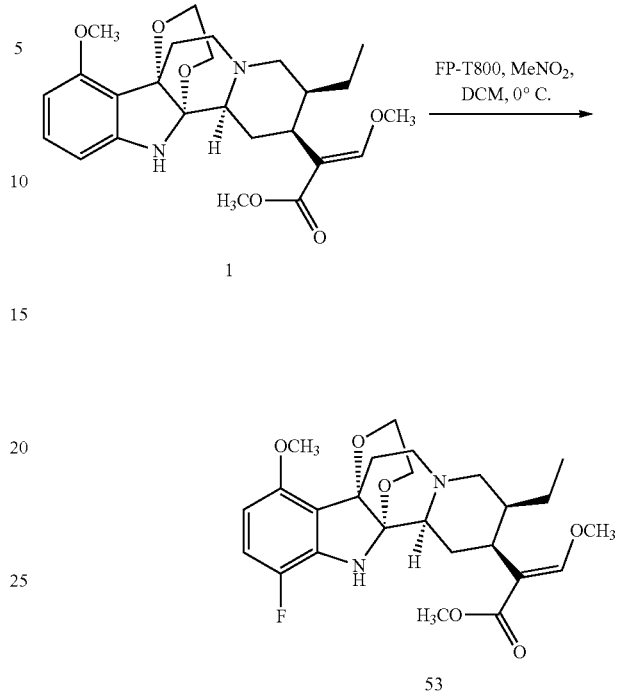
Scheme 6b. Alternative synthesis of 12-substituted MG-EG compounds.
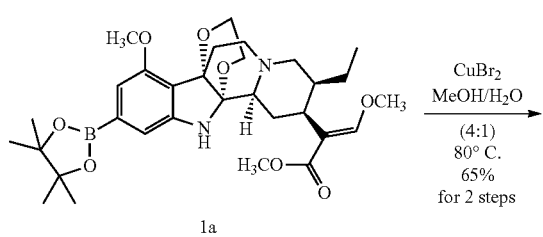
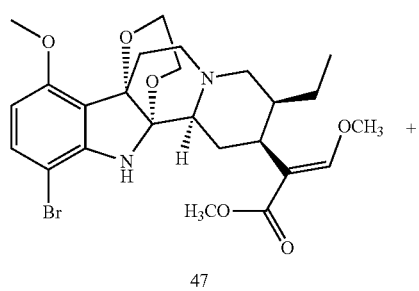
The C12 boronate ester 1b and 12-bromo-MG-EG (4) are converted to various C12 substituted MG-EG compounds (48-54) using procedures and reagents analogous to those used for C11 compounds (Scheme 7, for reference see Scheme 3).
Scheme 7. Synthesis of other 12-substituted MG-EG analogues.
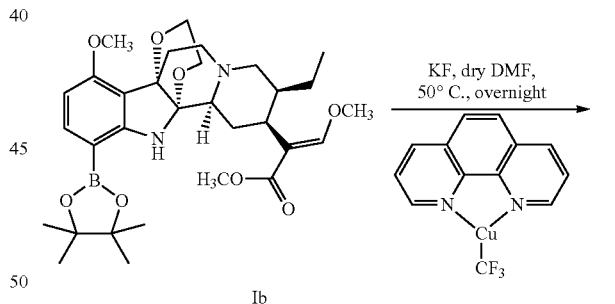
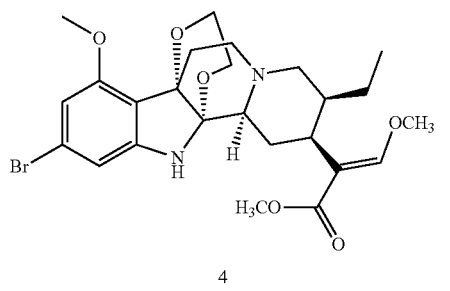
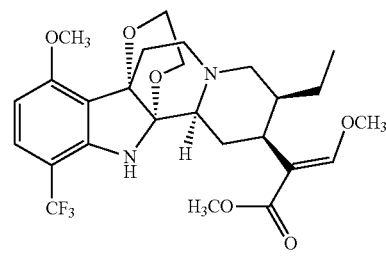

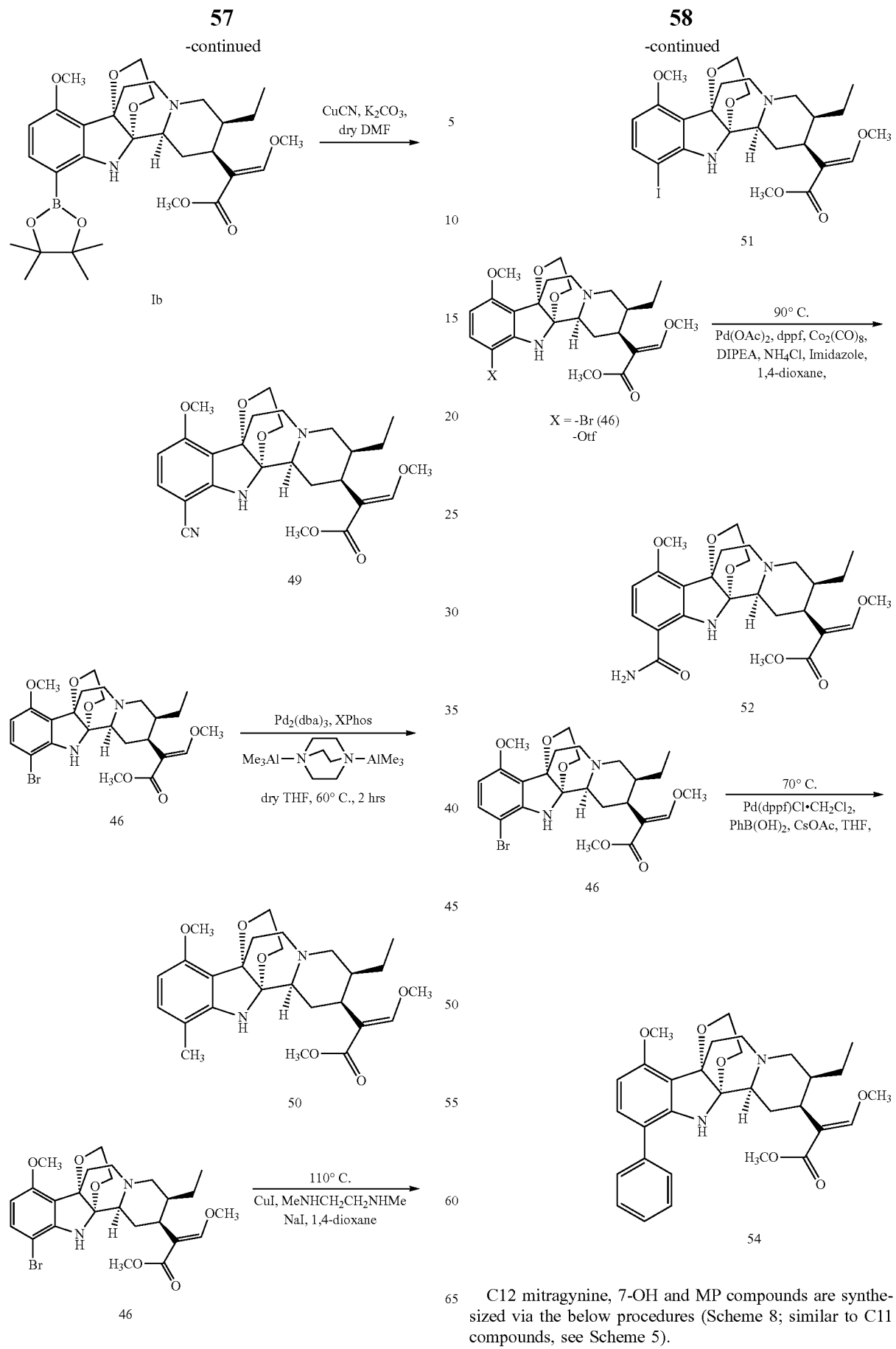
C12 mitragynine, 7-OH and MP compounds are synthesized via the below procedures (Scheme 8; similar to C11 compounds, see Scheme 5).

Scheme 8. Synthesis of C12 analogs of mitragynine scaffolds.

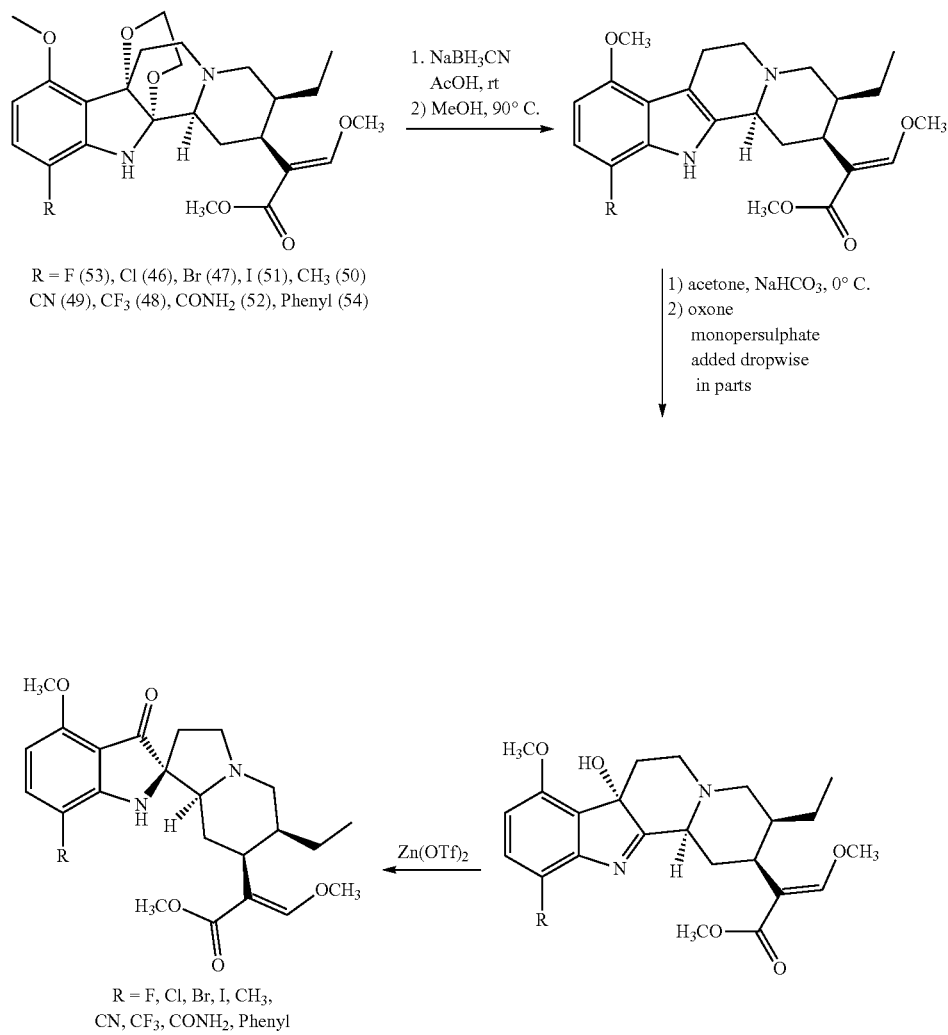

R = F (53), Cl (46), Br (47), I (51), CH₃ (50)
CN (49), CF₃ (48), CONH₂ (52), Phenyl (54)

R = F, Cl, Br, I, CH₃,
CN, CF₃, CONH₂, Phenyl

The C20 analogs are synthesized de novo (Kruegel, A. C. et al. 2016). The sequence (as shown in Scheme 9) starts from the key intermediate 55, which is submitted to the through Mannich-Micheal cyclization sequence with a modified vinyl ketone (shown in Scheme 9, 55 to 56 conversion), affording a cyclic ketone (not shown), followed by olefination and ene ester reduction to render the key intermediate 56. Deprotonation of the 56 and the Claisen condensation with methyl formate gives the enol ester intermediate 57, which is alkylated to provide the versatile intermediate 58. This intermediate is subjected to various reduction/cross-coupling reactions (shown in Scheme 10), after deprotection of the TBS group, to afford C20 modified mitragynine compounds. The C20 modified mitragynines is converted to the corresponding MG-EG, 7-OH and MP compounds via established protocols (see above).

Scheme 9. Synthesis of C20 analogs on the basis of total synthesis.

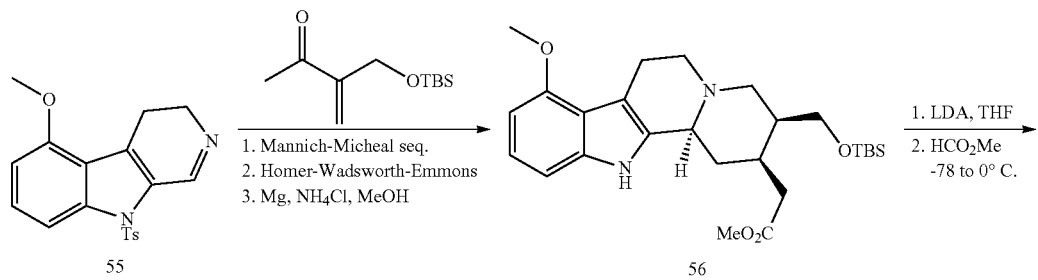

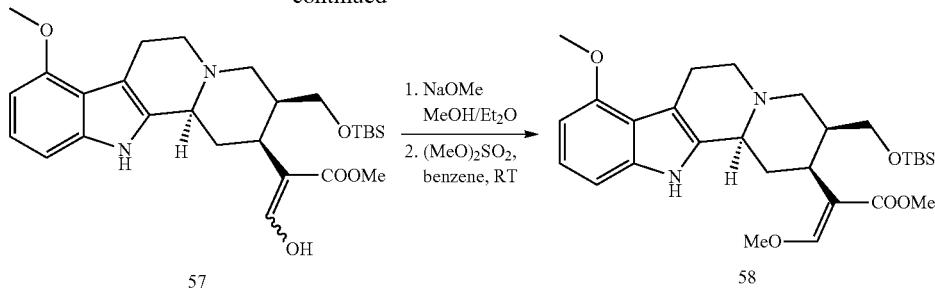

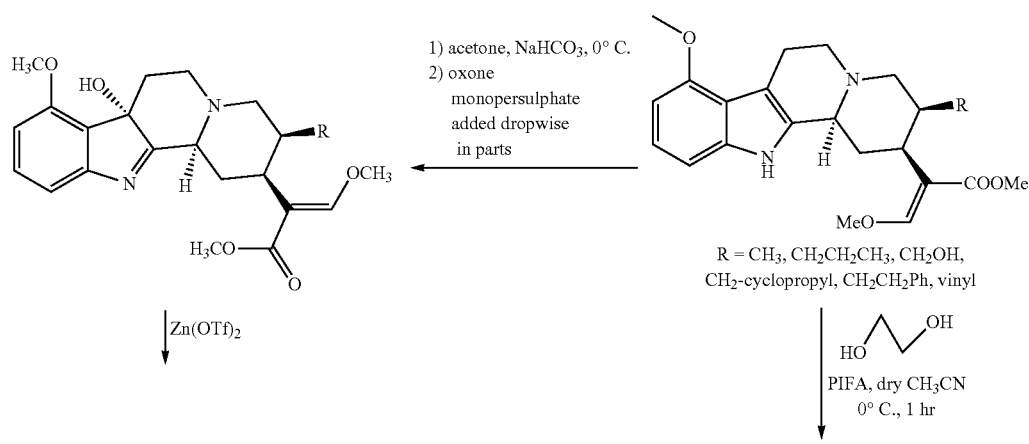

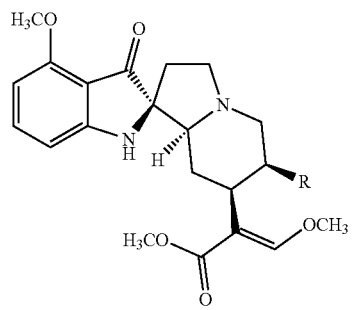

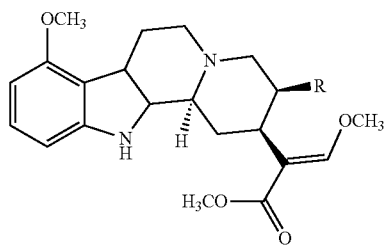

The versatile intermediate 58 is used to synthesize various C20 modified scaffolds via the following sequence (Scheme 10). The TBS protecting group in 58 is deprotected to yield 59 via one out of several established deprotection protocols (for example, Kaburagi, Y. and Kishi, Y. 2007), which is converted Lo a wide spectrum of derivatives 60-68 via cross coupling and/or substitution reactions. For instance, the bromination is conducted via standard procedures (Rouquet, G. et al. 2011), followed by the Stille reaction (Menzel. K. and Ku, G. C. 2003) to give the allyl derivative 61. The cyclopropylmethyl compound 66 is prepared by cyclopropanation (Yun, Y. K. et al 2002), the propyl compound 65 by selective hydrogenation from 61 (Cai, Y. et al. 2017), the methyl derivative 64 by reduction (Gevorgyan, V. et al. 1999), the vinyl compound 68 by a two-step oxidation-olefination sequence (Matsuo, G. et al. 2004) and phenylethyl 63 from 68 via iodination of terminal alkene (Lv, C. et al. 2016) followed by Hiyama cross coupling reaction (Lee, J. Y. and Fu, G. C. 2003, Scheme 10) or from 60 through Suzuki coupling using benzyl boron reagents (Kirchhoff, J. H. et al. 2002; Choi, J. and Fu G. C. 2017).

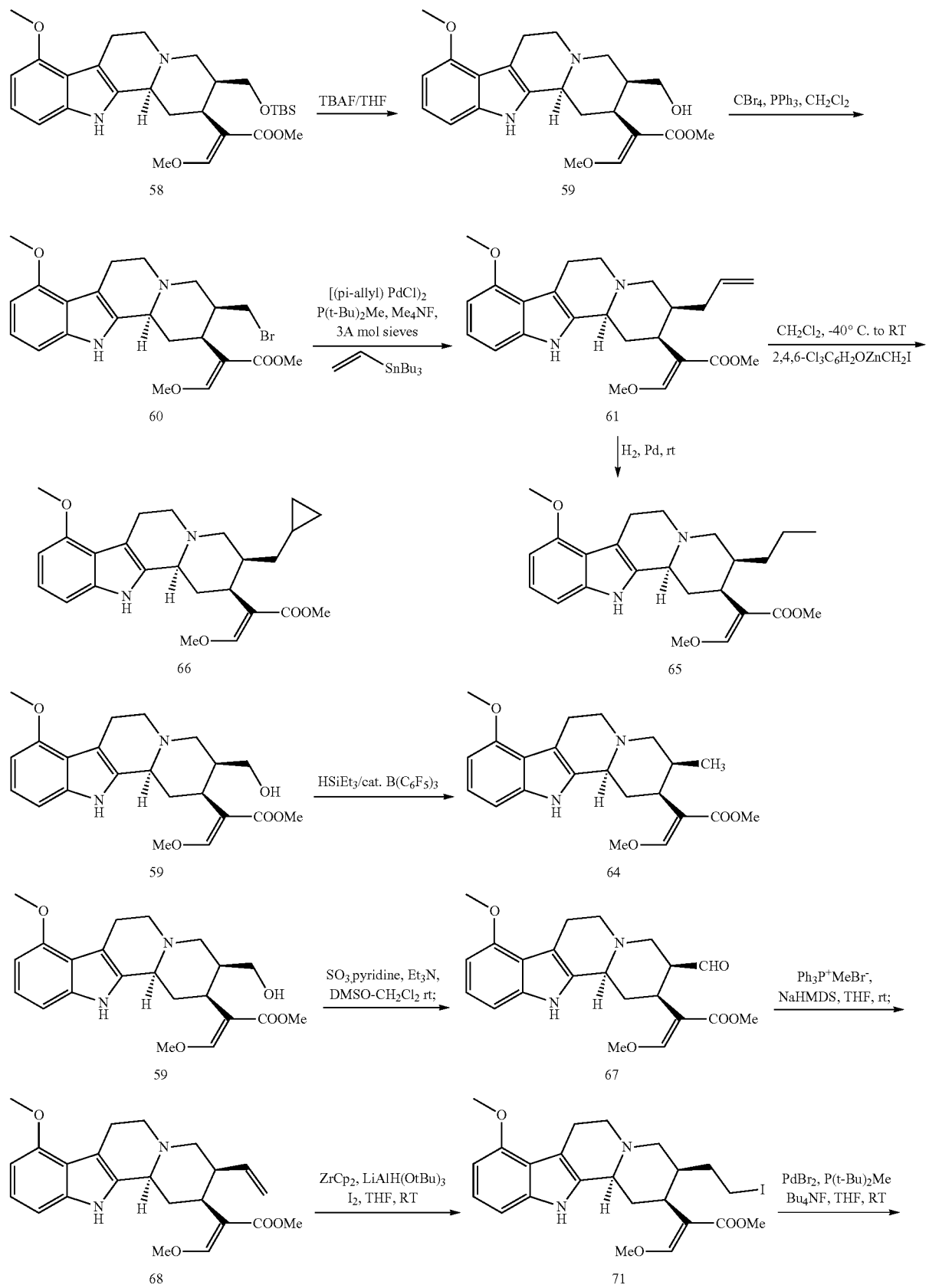
Scheme 10. Synthesis of C20 modified mitragynine compounds.

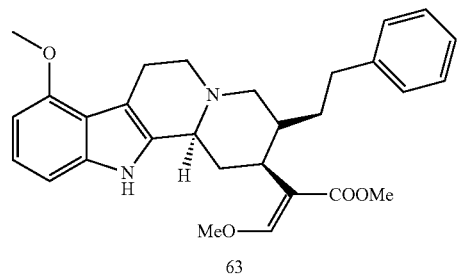

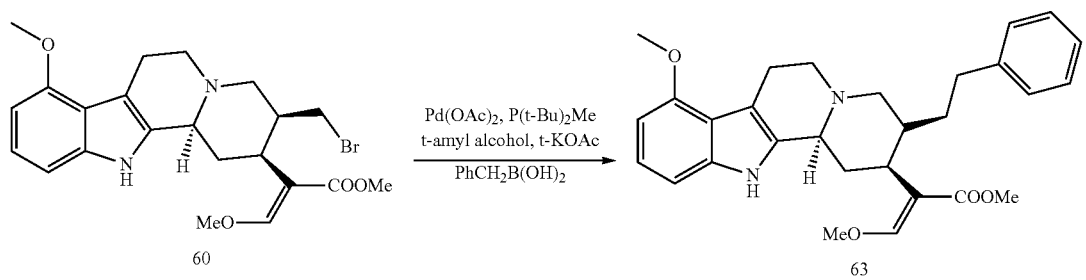

To synthesize the 10,11-disubstituted compounds and 11,12-disubstituted compounds the following sequence of reactions is followed. Electrophilic aromatic substitution reaction, e.g. fluorination, chlorination, bromination, nitration and methoxylation on compounds 2-11 provides a mixture of both 10,11- and 11,12-disubstituted MG-EG compounds (Scheme 11, Takayama, H. et al. 2006). The 11,12-MG compounds are also synthesized from compounds 2-11 by Ir-catalyzed selective C12 borylation as shown in Scheme 6.

Scheme 11. Synthesis of 10, 11- and 11, 12-disubstituted MG-EG compounds.

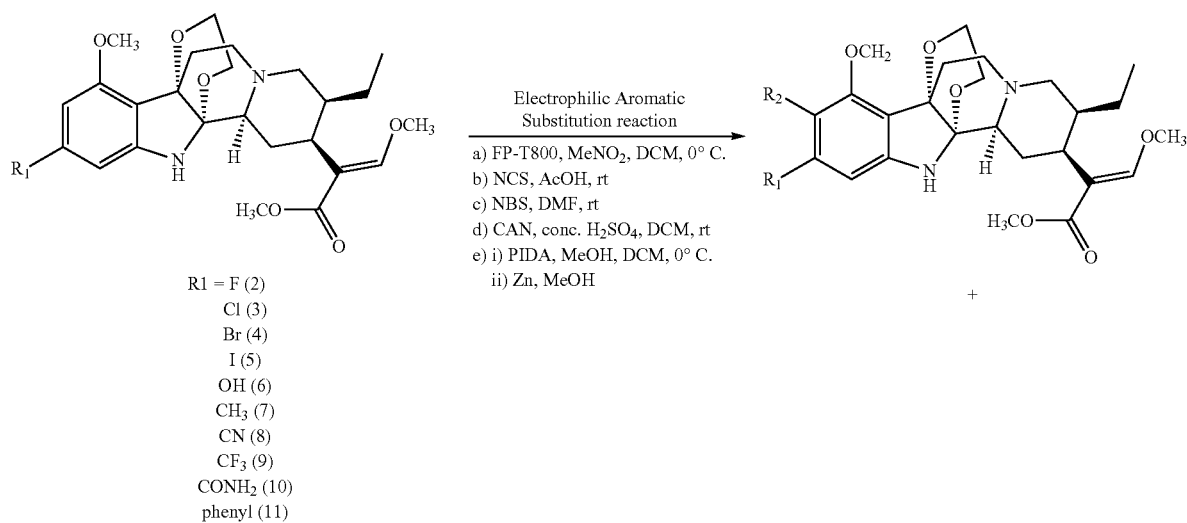

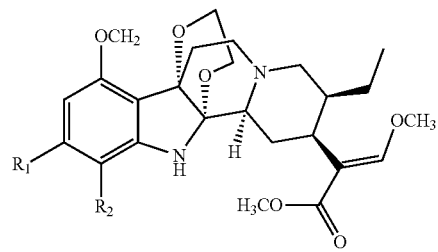

R₁ = F, Cl, Br, I, CH₃,
CN, CF₃, CONH₂, Phenyl.
R₂ = F, (a), Cl (b), Br (c),
NO₂ (d), OMe, (e)

The disubstituted MG-EG compounds are converted to disubstituted mitragynine, 7-OH and MP series by reduction, oxidations and rearrangements reactions (Scheme 12) as shown for the C11 analogs above.

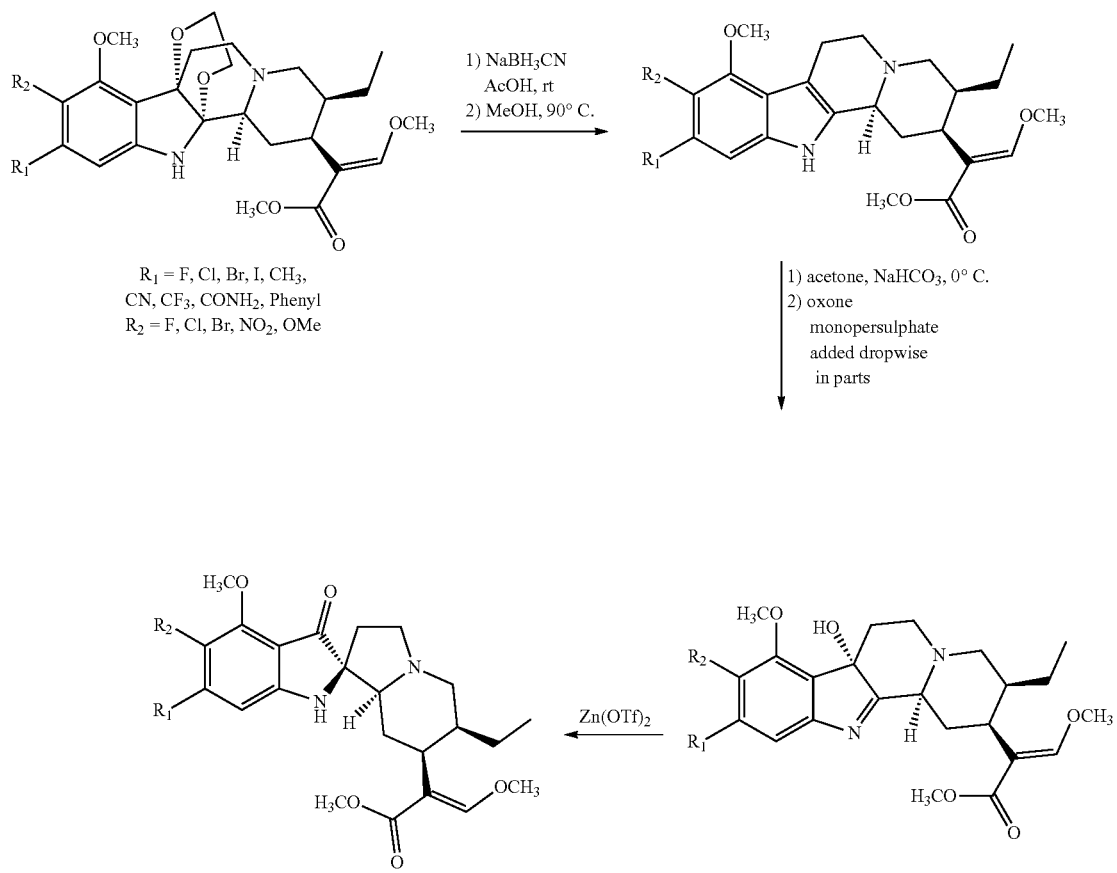

Scheme 12. Synthesis of C11 + C10 (Class IV) and C11 + C12 (Class VI) substituted scaffolds.

To synthesize the 10,12-disubstituted compounds the following sequence of reactions is followed. Electrophilic aromatic substitution reaction (Takayama, H. et al. 2006) on compounds 46-54 provides give 10,12-disubstituted MG-EG compounds (Scheme 13). The disubstituted MG-EG compounds are further converted to disubstituted mitragynine, 7-OH and MP by reduction, oxidations and rearrangement reactions as shown above.

Scheme 13. Synthesis of 10, 12-disubstituted scaffolds

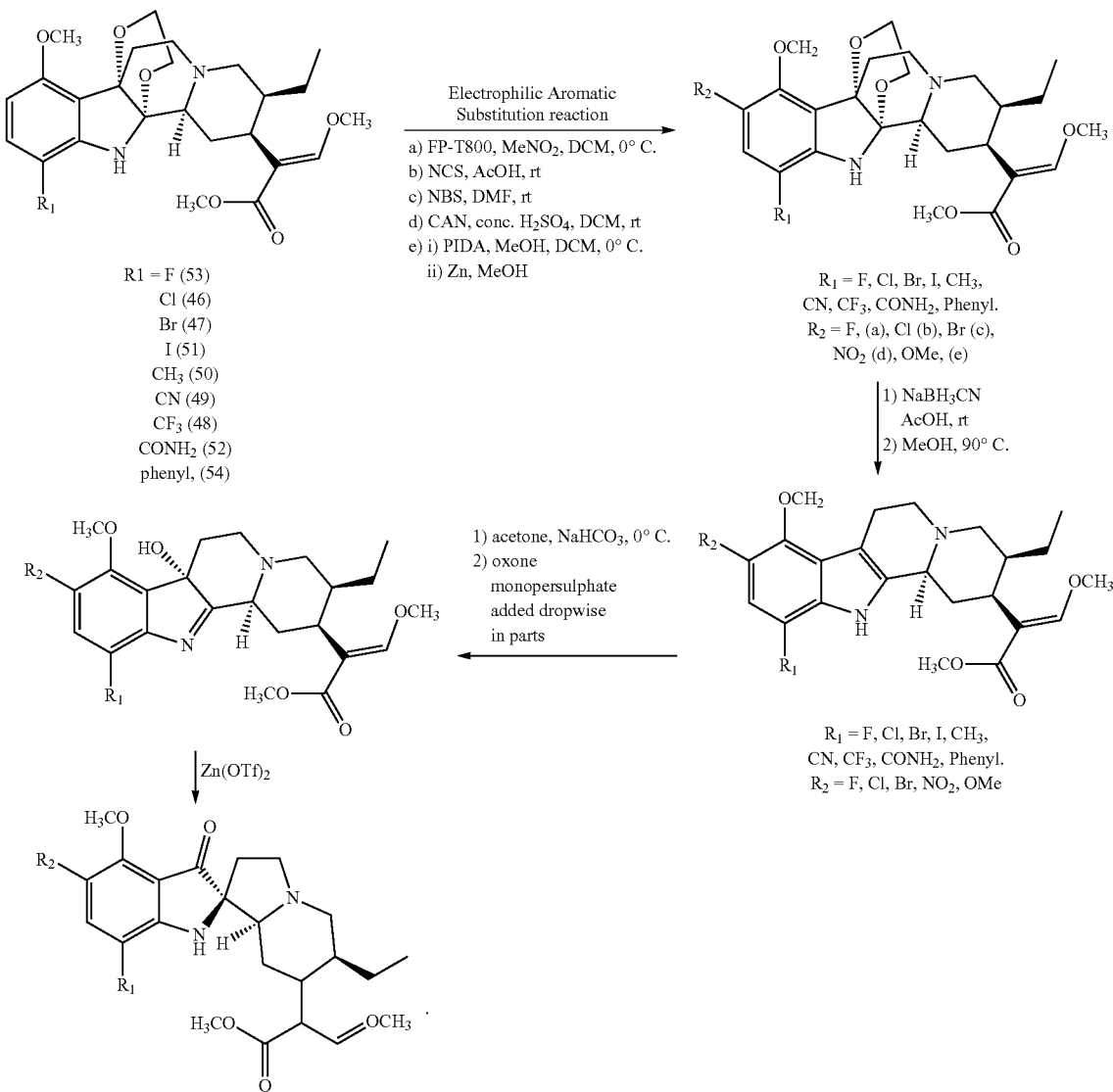

Experimental Protocol
General Consideration (Synthesis)

Reagents and solvents were obtained from commercial sources and were used without further purification unless otherwise stated (including anhydrous solvents). All reactions were performed in a dried glassware (flame-dried or oven-dried overnight) under an argon atmosphere unless otherwise seated and monitored by TLC using solvent mixtures appropriate to each reaction. All column chromatography was performed on silica gel (40-63 µm). For compounds containing a basic nitrogen, $Et_3N$ was often used in the mobile phase in order to provide better resolution. In these cases, TLC plates were pre-soaked in the $Et_3N$-containing solvent and then allowed Lo dry briefly before use in analysis, such that an accurate representation of Rf was obtained. Nuclear magnetic resonance spectra were recorded on 400 or 500 MHz instruments as indicated. Chemical shifts are reported as δ values in ppm referenced to $CDCl_3$ ($^1$H NMR=7.26 and $^{13}$C NMR=77.16). Multiplicity is indicated as follows: s (singlet); d (doublet); t (triplet); q (quartet); dd (doublet of doublets); dt (doublet of triplets); td (triplet of doublets); m (multiplet); br (broad). in some cases, spectra are complicated by the presence of multiple conformers, resulting in peak broadening or additional splitting. As a result of these effects, multiple peaks may correspond to the same proton group or carbon atom. When possible, this is indicated by an "and" joining two listed peaks or spectral regions. All carbon peaks are rounded Lo one decimal place unless such rounding would cause two close peaks to become identical. In these cases, two decimal places are retained. Low resolution mass spectra (LRMS) were recorded on a quadrupole mass spectrometer (ionization mode: APCI+ or ESI+). High-resolution mass spectra (HRMS) were recorded on a quadrupole time-of-flight mass spectrometer (ionization mode: ESI+). Reaction in vials at elevated temperature were performed in an aluminum heating block and the temperature was regulated by a thermometer immersed in a vial containing silicon oil.

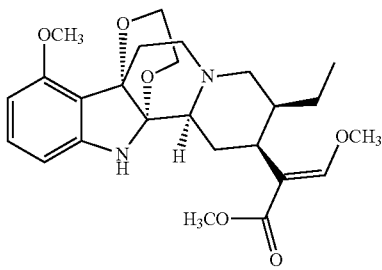

Compound 1 (EG-MG).

Reaction was performed according to a published procedure (Takayama, H. et al. 2006). To a solution of mitragynine (600 mg, 1.51 mmol) in dry MeCN (12 mL) were added dry ethylene glycol (12 mL) and PIFA (649 mg, 1.51 mmol) at 0° C. and the mixture was stirred for 1 h at 0° C. under argon atmosphere. After adding chilled aqueous $NaHCO_3$ solution (120 mL), the mixture was extracted three times with $CH_2Cl_2$ (3×40 mL). The combined extract was washed with brine, dried over $MgSO_4$, and evaporated. Product was purified by column chromatography using 1:9 to 2:8 EA:Hex+2% $Et_3N$. Product 1 was obtained as a light green solid (468 mg, 68%).

$^1$H NMR (400 MHz, $CDCl_3$) δ 7.41 (s, 1H), 7.07 (dd, J=8.3, 7.7 Hz, 1H), 6.43-6.26 (m, 2H), 4.25 (s, 1H), 3.92 (td, J=11.6, 2.7 Hz, 1H), 3.86-3.81 (m, 4H, signal overlap), 3.78 (s, 3H), 3.10 (s, 3H), 3.67 (dd, J=11.3, 2.3 Hz, 1H), 3.46-3.38 (m, 1H), 2.98 (dd, J=11.6, 2.2 Hz, 1H), 2.92 (dt, J=13.0, 3.6 Hz, 1H), 2.53-2.42 (m, 2H), 2.39-2.30 (m, 2H), 2.28-2.23 (m, 1H), 2.15 (dt, J=14.4, 2.5 Hz, 1H), 1.87-1.69 (m, 3H), 1.56 (d, J=11.1 Hz, 1H), 1.24-1.21 (m, 1H), 0.84 (t, J=7.4 Hz, 3H). $^{13}$C NMR (101 MHz, $CDCl_3$) 169.1, 160.4, 156.9, 149.0, 129.9, 115.8, 111.7, 105.3, 102.8, 90.8, 81.3, 62.3, 61.6, 61.2, 60.8, 58.5, 55.3, 51.3, 50.2, 40.5, 40.1, 35.4, 24.2, 19.2, 13.1, LR-MS (APCI+) calcd. for $C_{25}H_{35}N_2O_6^+$ [M+H]$^+$: 459.2, found 459.7.

C—H Borylation Reaction (Selectivity C11:C12=16-20:1) of 1 and Subsequent Transformations General procedure: Starting material 1 (50 mg, 0.11 mmol), [Ir(COD)OMe]$_2$ (3.6 mg, 5.5 μmol), 3,4,7,8-Tetramethyl-1,10-phenanthroline (3.9 mg, 16 μmol) and $B_2Pin_2$ (111 mg, 0.44 mmol) were balanced into an oven dried vial. Vial was purged with argon and dry heptane (2.5 mL) was added under argon. Vial was sealed with Teflon lined screw cap and heated to 65° C. RM becomes a dark red-brown solution after 5-15 minutes of heating. After 15-24 h when LR-MS indicated complete consumption of SM the RM was concentrated to dryness on rotavap (RM is prone to bumping, if necessary MeOH can be used to wash down any material that splashed). This intermediate was immediately used to prepare the —Cl 3, —Br 4, —OH 6, —CN 8 and —CF$_3$ 9 derivatives without further purification.

Up to 100 mg of SM 2 can be used in one reaction vial (8 ml volume) to prepare the boronate ester intermediate using only (1.5 mL) of dry Heptane. It is however necessary to divide the crude intermediate into multiple reaction vessels for the subsequent reaction (the reactions are very sensitive to the ratio of MeOH/H$_2$O and total reaction volume). The intermediate boronate ester is air and moisture sensitive and unstable during column purification. Other solvents than those used for further reactions (mainly chlorinated e.g. DCM and CHCl$_3$) can lead to a significant protodeborylation. Compounds prepared from the boronate ester intermediate are sometimes contaminated with decomposition products from excess of $B_2Pin_2$. These can be removed either by a repeated chromatography purification (preferably PTLC) or after further reaction seeps.

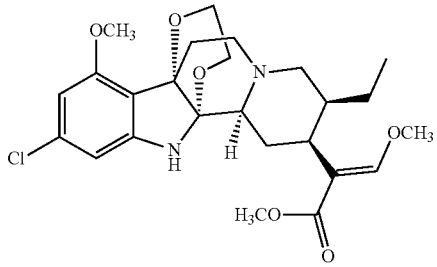

Compound 3 (11-chloro-MG-EG).

Boronate ester intermediate was prepared as described in general procedure from 2 (50 mg, 0.11 mmol). To the dark residue of intermediate was added $CuCl_2.2H_2O$ (53.0 mg, 0.31 mmol) and a mixture of MeOH+H$_2$O (4+1 mL). Vial was sealed, and the RM was then heated to 80° C. with vigorous stirring (slower stirring will cause incomplete conversion due to precipitation during the reaction). After 12 h, TLC (EA:Hex 1:1+2% $Et_2N$) and LR-MS indicated complete conversion of the intermediate. RM was diluted with brine (15 mL) and extracted with DCM (3×10 mL). Combined DCM extracts were dried over with $Na_2SO_4$ and evaporated. Product was purified by PTLC using EA:Hex 1:4+2% $Et_3N$. Plate was developed twice. Product 3 was obtained as a white solid (33 mg, 60%).

$^1$H NMR (400 MHz, $CDCl_3$) δ 7.40 (s, 1H), 6.39-6.36 (m, 2H), 4.30 (s, 1H), 3.91 (td, J=11.7, 2.9 Hz, 1H), 3.84-3.74 (m, 7H), 3.69 (s, 3H), 3.66 (dd, J=11.4, 2.5 Hz, 1H), 3.45-3.36 (m, 1H), 2.98 (dd, J=11.6, 2.2 Hz, 1H), 2.91 (dt, J=13.0, 3.6 Hz, 1H), 2.50-2.40 (m, 2H), 2.38-2.19 (m, 3H), 2.12 (dt, J=14.3, 2.5 Hz, 1H), 1.87-1.66 (m, 3H), 1.56 (d, J=11.4 Hz, 1H), 1.21-1.18 (m, 1H), 0.84 (t, J=7.4 Hz, 3H). $^{13}$C NMR (126 MHz, $CDCl_3$ δ 169.2, 160.6, 157.2, 149.8, 135.1, 114.5, 111.8, 105.9, 103.9, 91.0, 81.0, 62.45, 61.8, 61.3, 60.9, 58.6, 55.7, 51.4, 50.3, 40.6, 40.2, 35.5, 24.3, 19.3, 13.2. LR-MS (APCI+) calcd. for $C_{25}H_{34}ClN_2O_5^+$ [M+H]$^+$: 493.2, found 493.9.

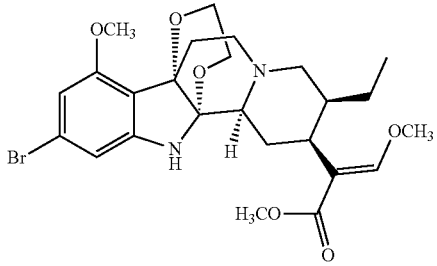

Compound 4 (11-bromo-MG-EG).

Boronate ester intermediate was prepared as described in general procedure from 2 (50 mg, 0.11 mmol). To the dark residue of intermediate was added CuBr$_2$ (73 mg, 0.33 mmol) and a mixture of MeOH+H$_2$O (4+1 mL). Vial was sealed, and the RM was then heated to 80° C. with vigorous stirring (slower stirring will cause incomplete conversion due to a precipitation of reactants during the reaction). After 12 h, TLC (EA:Hex 1:1+2% $Et_3N$) and LR-MS indicated complete conversion of the intermediate. RM was diluted with brine (15 mL) and extracted with DCM (3×10 mL). Combined DCM extracts were dried over Na$_2$SO$_4$ and evaporated. Product was purified by PTLC using EA:Hex 1:4+2% Et$_3$N. Plate was developed twice. Product 4 was obtained as a pale-yellow solid (59 mg, 60%).

$^1$H NMR (400 MHz, CDCl$_3$) δ 7.40 (s, 1H), 6.54 (s, 2H), 4.29 (s, 1H), 3.91 (td, J=11.6, 2.8 Hz, 1H), 3.82 (s, 3H), 3.82-3.74 (m, 4H), 3.70 (s, 3H), 3.66 (dd, J=11.6, 2.7 Hz, 1H), 3.41 (dd, J=11.6, 2.5 Hz, 1H), 2.98 (dd, J=11.5, 2.2 Hz, 1H), 2.91 (dt, J=13.0, 3.5 Hz, 1H), 2.49-2.40 (m, 2H), 2.38-2.29 (m, 2H), 2.29-2.22 (m, 1H), 2.13 (dd, J=14.4, 2.5 Hz, 1H), 1.83-1.69 (m, 3H), 1.56 (d, J=15.0 Hz, 1H), 1.24-1.21 (m, 1H), 0.84 (t, J=7.4 Hz, 3H). $^{13}$C NMR (126 MHz, CDCl$_3$) δ 169.2, 160.5, 157.3, 150, 122.8, 115.0, 111.7, 108.7, 106.7, 91.0, 81.1, 62.5, 61.8, 61.3, 60.9, 58.6, 55.7, 51.4, 50.2, 40.6, 40.2, 35.4, 24.2, 19.3, 13.2. LR-MS (APCI+) calcd. for C$_{25}$H$_{34}$BrN$_2$O$_5$$^+$ [M+H]$^+$: 537.2, found 537.2.

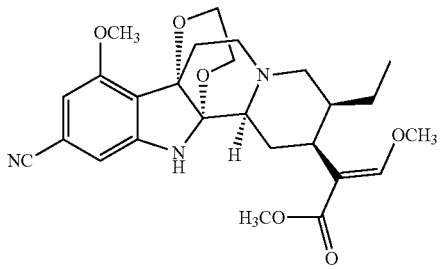

Compound 8 (11-cyano-MG-EG).

Boronate ester intermediate was prepared as described in general procedure from 2 (40 mg, 87 μmol). To the dark solid residue was added CuCN (31 mg, 0.35 mmol) and K$_2$CO$_3$ (36 mg, 0.26 mmol) followed by dry DMF (2 mL). The RM was then heated to 80° C. After 12 h the reaction mixture was cooled to RT diluted with diethyl ether and washed with brine (10 mL), dried over Na$_2$SO$_4$ and concentrated. Residue was purified by PTLC (EA:Hex 1:4+2% Et$_3$N). Product 8 was obtained as a yellow-brown solid (7 mg, 25%).

$^1$H NMR (500 MHz, CDCl$_3$) δ 7.42 (s, 1H), 6.67 (d, 3=1.1 Hz, 1H), 6.63 (d, J=1.1 Hz, 1H), 4.48 (s, 1H), 3.99-3.89 (m, 1H), 3.88 (s, 3H); 3.81 (s, 3H), 3.76-3.72 (m, 1H), 3.71 (s, 3H), 3.50-3.38 (m, 1H), 3.00 (dd, J=11.7, 2.1 Hz, 1H), 2.92 (dt, J=13.1, 3.6 Hz, 1H), 2.56-2.43 (m, 2H), 2.40-2.24 (m, 3H), 2.14 (dt, J=14.4, 2.5 Hz, 1H), 1.81-1.74 (m, 2H), 1.76-1.67 (m, 1H), 1.58 (d, J=11.5 Hz, 1H), 1.34-1.18 (m, 1H), 0.85 (L, J=7.4 Hz, 3H). $^{13}$C NMR (126 MHz, CDCl$_3$) 169.0, 160.5, 156.9, 149.5, 121.4, 119.4, 112.9, 111.5, 108.6, 107.0, 90.8, 81.2, 62.7, 61.7, 61.1, 60.6, 58.4, 55.8, 51.3, 49.9, 40.4, 39.8, 35.0, 24.1, 19.2, 13.2. LR-MS (APCI+) calcd. for C$_{26}$H$_{34}$N$_3$O$_6$$^+$ [M+H]$^+$: 484.3, found 484.6.

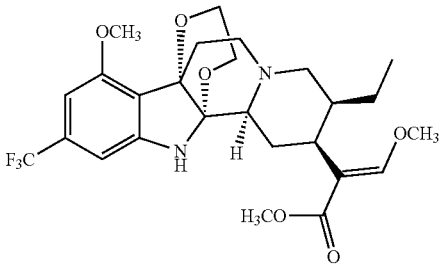

Compound 9 (11-CF$_3$-MG-EG).

Boronate ester intermediate was prepared as described in general procedure from 2 (40 mg, 87 μmol). To the dark solid residue of intermediate was added [(phen)CuCF$_3$] (95.2 mg, 0.30 mmol) and KF (5.0 mg, 86 μmol) followed by anhydrous DMF (2 mL). RM was further heated to 50° C. After 12 h the reaction mixture was cooled to RT, diluted with diethyl ether and washed with brine (10 mL), dried over Na$_2$SO$_4$ and concentrated. Residue was purified by PTLC (EA:Hex 1:4+2% Et$_3$N). Product 9 was obtained as a yellow-brown solid (9.4 mg, 30%).

$^1$H NMR (500 MHz, CDCl$_3$) δ 7.41 (s, 1H), 6.66 (d, J=1.1 Hz, 1H), 6.62 (d, J=1.1 Hz, 1H), 4.47 (s, 1H), 3.98-3.88 (m, 1H), 3.87 (s, 3H), 3.80 (s, 3H), 3.75-3.71 (m, 2H), 3.70 (s, 3H), 3.49-3.37 (m, 1H), 2.99 (dd, J=11.7, 2.1 Hz, 1H), 2.91 (dt, J=13.1, 3.6 Hz, 1H), 2.55-2.42 (m, 2H), 2.39-2.23 (m, 3H), 2.13 (dt, J 2.5 Hz, 1H), 1.80-1.73 (m, 2H), 1.75-1.66 (m, 1H), 1.57 (d, J=11.5 Hz, 1H), 1.31-1.19 (m, 1H), 0.84 (t, J=7.4 Hz, 3H).

$^{13}$C NMR (126 MHz, CDCl$_3$) δ 169.2, 160.6, 157.0, 149.4, 111.7, 102.4, 100.3, 91.1, 81.3, 62.7, 61.8, 61.3, 60.8, 58.6, 55.8, 51.5, 50.2, 40.6, 40.2, 35.3, 32.1, 24.3, 22.9, 19.3, 14.3, 13.2. $^{19}$F NMR (376 MHz, CDCl$_3$) δ−62.47.

LR-MS (APCI+) calcd. for C$_{26}$H$_{34}$F$_3$N$_2$O$_6$$^+$ [M+H]$^+$: 527.2, found 527.6.

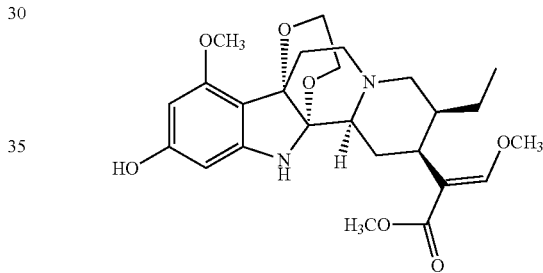

Compound 6 (11-hydroxy-MG-EG).

Boronate ester intermediate was prepared as described in general procedure from 2 (50 mg, 0.11 mmol). The dark residue was dissolved in 0.7 ml of THF and 30% H$_2$O$_2$ (102 UL, 0.66 mmol) was added dropwise at 0° C. The reaction mixture was then stirred for 30 min at room temperature. RM was then quenched with 5% Na$_2$S$_2$O$_3$.5H$_2$O (1 ml) and extracted with DCM (3×10 mL). Combined DCM extracts were dried over Na$_2$SO$_4$ and evaporated. Product was purified by PTLC using EA:Hex 1:4+2% Et$_3$N. Plate was developed twice. Product 6 was obtained as a pale-brown solid (29.0 mg, 55%).

$^1$H NMR (400 MHz, CDCl$_3$) δ 1.40 (s, 1H), 5.96-5.83 (m, 2H), 4.23 (s, 1H), 3.94-3.83 (m, 2H), 3.80 (s, 3H), 3.78 (s, 3H), 3.70 (s, 3H), 3.64 (dd, J=8.5, 2.3 Hz, 1H), 3.43 (d, J=9.4 Hz, 1H), 3.00 (dd, J=11.7, 2.1 Hz, 1H), 2.92 (dt, J=12.9, 3.6 Hz, 1H), 2.49-2.43 (m, 2H), 2.39-2.19 (m, 4H), 2.11 (dt, J=14.4, 2.5 Hz, 1H), 1.85-1.70 (m, 2H), 1.58 (d, J=11.4 Hz, 1H), 1.31 (s, 1H), 0.85 (t, J=7.3 Hz, 3H). $^{13}$C NMR (101 MHz, CDCl$_3$) δ 169.2, 160.6, 158.4, 157.8, 149.6, 111.9, 108.0, 93.5, 91.5, 90.9, 81.1, 62.3, 61.9, 61.5, 61.4, 58.6, 55.4, 51.4, 50.7, 40.7, 40.1, 35.9, 24.3, 19.4, 13.2. LR-MS (APCI+) calcd. for C$_{25}$H$_{35}$N$_2$O$_7$$^+$ [M+H]$^+$: 415.2, found 475.8.

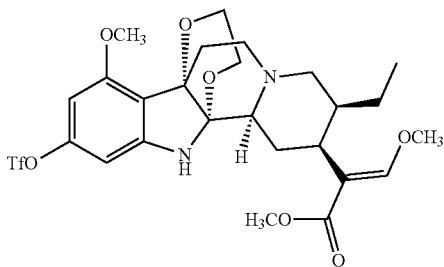

Compound 34 (11-triflate-MG-EG).

To a solution of SM 6 (115 mg, 0.24 mmol) in dry DMF (3 mL) at room temperature was added DIPEA (2 mL, 1.2 mmol) and N-phenyl-bis(trifluoromethanesulfonimide) (173 mg, 0.48 mmol). The reaction mixture was stirred at 50° C. overnight, quenched by the addition of saturated aqueous NaHCO$_3$ and extracted with DCM (3×15 mL). The combined organic phases were washed with brine, dried over Na$_2$SO$_4$ and evaporated. Product was purified by column chromatography using EA:Hex 3:7+2% Et$_3$N. Product 34 was obtained as a yellow powder (117 mg, 80%).

$^1$H NMR (400 MHz, CDCl$_3$) s 7.41 (s, 1H), 6.28 (d, J=3.8 Hz, 2H), 4.46 (s, 1H), 3.92 (td, J=11.7, 3.1 Hz, 1H), 3.84 (s, 3H), 3.82-3.74 (m, 4H), 3.73-3.65 (m, 4H), 3.43 (dd, J=11.1, 2.5 Hz, 1H), 2.99 (dd, J=11.5, 2.1 Hz, 1H), 2.92 (dt, J=13.1, 3.6 Hz, 1H), 2.51-2.40 (m, 2H), 2.38-2.22 (m, 3H), 2.14 (dt, J=14.4, 2.5 Hz, 1H), 1.81-1.74 (m, 2H), 1.74-1.64 (m, 1H), 1.57 (d, J=11.2 Hz, 1H), 1.22-1.15 (m, 1H), 0.85 (t, J=7.4 Hz, 3H). $^{19}$F NMR (471 MHz, CDCl$_3$) δ−72.03. $^{13}$C NMR (126 MHz, CDCl$_3$) δ 169.2, 160.6, 157.3, 150.0, 149.9, 122.8, 120.1, 117.5, 115.8, 115.0, 111.6, 98.6, 96.8, 91.1, 81.0, 62.6, 61.8, 61.3, 60.9, 58.6, 55.9, 51.4, 50.2, 40.5, 40.1, 35.4, 24.3, 19.3, 13.2. LR-MS (APCI+) calcd. for C$_{25}$H$_{35}$N$_2$O$_7$$^+$ [M+H]$^+$: 607.2, found 607.9.

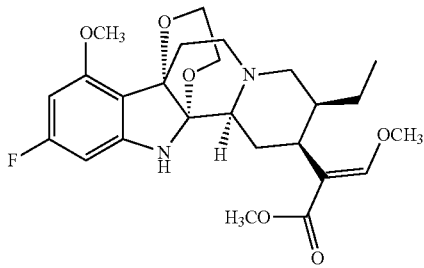

Compound 2 (11-fluoro-MG-EG).

To a solution 9f SM 34 (50 mg, 0.09 mmol) in dioxane (1.5 mL) at RT was added lithium chloride (19.8 mg, 0.47 mmol), Pd(PPh$_3$)$_4$ (16.3 mg, 0.014 mmol, 15 mol %) and bis(tri-n-butyltin) (465 µL, 0.93 mmol). After stirring for 24 h at 100° C., the reaction mixture was cooled to RT and concentrated in vacuo. The residue was dissolved in hexane and then filtered through a pad of celite. After washing several times with hexane, the combined washings were evaporated. Product was used for the next step without purification. To the solution of the arylstannane intermediate (95 mg, 0.13 mmol) in acetone (2.0 mL) at RT was added silver triflate (63 mg, 0.25 mmol) and 1-chloromethyl-4-fluoro-1,4-diazoniabicyclo [2.2.2]octane bis(hexafluorophosphate) (50 mg, 0.15 mmol). The reaction mixture was stirred for 20 min at 23° C. and then concentrated in vacuo. The residue was purified by PTLC using EA:Hex 1:4+2% Et$_3$N. Product 2 was obtained as a white solid (30 mg, 50%).

$^1$H NMR (400 MHz, CDCl$_3$) δ 7.40 (s, 1H), 6.39-5.84 (m, 2H), 4.31 (s, 1H), 3.91 (td, J=11.7, 2.7 Hz, 1H), 3.84-3.75 (m, 7H), 3.70 (s, 3H), 3.66 (dd, J=11.5, 2.5 Hz, 1H), 3.42 (dd, J=11.6, 2.4 Hz, 1H), 3.02-2.93 (m, 1H), 2.91 (dt, J=13.0, 3.6 Hz, 1H), 2.44 (d, J=11.6 Hz, 2H), 2.40-2.19 (m, 3H), 2.19-2.05 (m, 1H), 1.90-1.64 (m, 3H), 1.58 (s, 1H), 1.26 (s, 1H), 0.84 (t, J=7.4 Hz, 3H). $^{13}$C NMR (126 MHz, CDCl$_3$) δ 169.2, 163.8, 159.1 (d, J=376.7 Hz), 157.5, 149.8 (d, J=14.3 Hz), 111.8, 111.3, 93.0 (d, J=26.3 Hz), 91.3, 91.1 (d, J=9.8 Hz), 80.9, 62.4, 61.8, 61.4, 61.0, 58.5, 55.7, 51.45, 50.4, 40.6, 40.2, 35.7, 24.3, 19.3, 13.2. $^{19}$F NMR (471 MHz, CDCl$_3$) δ−110.19 (dd, J=11.8, 9.1 Hz).

LR-MS (APCI+) calcd. for C$_{25}$H$_{34}$FN$_2$O$_5$$^+$ [M+H]$^+$: 477.2, found 477.1.

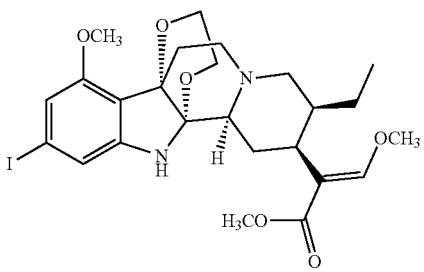

Compound 5 (11-iodo-MG-EG).

Starting material 4 (20.0 mg, 37.2 µmol), dried NaI (15.6 mg, 0.1 mmol), CuI (0.5 mg, 2.6 µmol) and N,N'-dimethylethylenediamine (2.3 mg, 26 µmol) were balanced into an oven-dried vial. Vial was purged with argon and dry 1,4-dioxane (0.25 mL) was added under a stream of argon. RM was heated to 110° C. for 24 h. LR-MS indicated formation of product but with a low conversion (TLC is not indicative enough due to a low difference in Rf value of starting compound and product). RM was evaporated and dried on high vacuum. More NaI (63.7 mg, 0.42 mmol), CuI (3 mg, 16 µmol) and N,N'-dimethylethylenediamine (9.4 mg, 11 µmol) were added followed by dry 1,4-dioxane (0.3 mL) under Ar. RM was heated 22h after which LR-MS indicated nearly total conversion. RM was diluted with DCM (10 mL) and washed 3× with diluted aq. NH$_3$ (H$_2$O: 28% aq.NH$_3$ 10:0.1 mL), DCM was dried over Na$_2$SO$_4$ and evaporated. Crude product was filtered through silicagel in EA:Hex 1:1+2% Et$_3$N and further purified by PTLC (EA:Hex 1:4+ 2% Et$_3$N, 2× developed). Product 5 was obtained as a yellow solid (13 mg, 59%).

$^1$H NMR (500 MHz, CDCl$_3$) δ 7.40 (s, 1H), 6.72 (d, J=10.1 Hz, 2H), 4.28 (s, 1H), 3.91 (td, J=11.8, 2.9 Hz, 1H), 3.85-3.80 (m, 3H), 3.80-3.74 (m, 4H), 3.72-3.63 (m, 4H), 3.47-3.37 (m, 1H), 3.03-2.94 (m, 1H), 2.90 (dt, J=13.2, 3.6 Hz, 1H), 2.51-2.39 (m, 2H), 2.38-2.29 (m, 2H), 2.28-2.21 (m, 1H), 2.11 (dt, J=14.5, 2.6 Hz, 1H), 1.84-1.66 (m, 3H), 1.55 (d, J=11.1 Hz, 1H), 1.24-1.16 (m, 1H), 0.84 (t, J=7.2 Hz, 3H). $^{13}$C NMR (126 MHz, CDCl$_3$) δ 169.2, 160.6, 157.4, 150.2, 116.0, 114.7, 112.7, 111.7, 94.0, 90.9, 81.3, 62.5, 61.8, 61.3, 60.8, 58.6, 55.8, 51.4, 50.2, 40.6, 40.2, 35.4, 24.3, 19.3, 13.2. LR-MS (APCI+): calcd. for C$_{31}$H$_{39}$N$_2$O$_6$$^+$ [M+H]$^+$: 585.1, found 585.2.

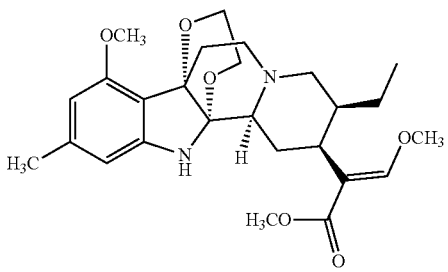

Compound 7 (11-methyl-MG-EG).

Starting material 4 (30 mg, 56 μmol), Pd$_2$(dba)$_3$ (6 mg, 6.7 μmol), Xphos (4.4 mg, 9.2 μmol) and DABAL-Me3 (57 mg, 0.22 mmol) were balanced into an oven dried vial. Vial was purged with argon and dry THF (1.5 mL) was added under argon. Vial was sealed with a Teflon lined screw cap and heated to 60° C. After stirring for 2 h complete conversion was observed by TLC-MS. The reaction mixture was cooled to RT and concentrated in vacuo. Product was purified by column chromatography using EA:Hex 1:4+2% Et$_3$N. Product 7 was obtained as a yellow solid (16 mg, 61%).

$^1$H NMR (500 MHz, CDCl$_3$) δ 7.41 (s, 1H), 6.21 (d, J=0.8 Hz, 2H), 4.17 (s, 1H), 3.91 (td, J=11.6, 2.6 Hz, 1H), 3.86-3.82 (m, 1H), 3.82 (s, 3H), 3.78 (s, 3H), 3.69 (s, 3H), 3.65 (dd, J=11.4, 2.4 Hz, 1H), 3.47-3.33 (m, 1H), 2.98 (dd, J=11.5, 2.1 Hz, 1H), 2.91 (dt, J=13.1, 3.6 Hz, 1H), 2.45 (tt, J=9.4, 2.9 Hz, 2H), 2.40-2.28 (m, 2H), 2.27 (s, 3H), 2.24-2.19 (m, 1H), 2.13 (dt, J=14.9, 2.8 Hz, 1H), 1.85-1.71 (m, 3H), 1.55 (d, J=11.3 Hz, 1H), 1.25-1.16 (m, 1H), 0.83 (t, J=7.4 Hz, 3H). $^{13}$C NMR (126 MHz, CDCl$_3$) δ 169.2, 160.4, 156.7, 149.1, 140.3, 113.0, 111.7, 106.0, 103.8, 90.9, 81.2, 62.3, 61.6, 61.3, 60.9, 58.5, 55.2, 51.3, 50.3, 40.5, 40.1, 35.6, 24.2, 22.1, 19.2, 13.1. LR-MS (APCI+) calcd. for C$_{26}$H$_{37}$N$_2$O$_6^+$ [M+H]$^+$: 473.3, found 473.8.

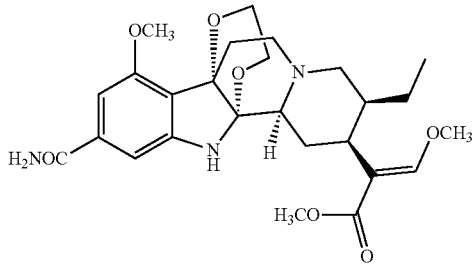

Compound 10 (11-carbamide-MG-EG).

Starting material 4 (20.0 mg, 37 pool), Pd(OAc)$_2$ (0.5 mg, 2.2 μmol), dppf (2.6 mg, 4.7 μmol), imidazole (2.6 mg, 38 μmol), Co$_2$(CO)$_8$ (7.6 mg, 22 μmol) and NH$_4$Cl (8.0 mg, 0.15 mmol) were balanced into an oven-dried vial. Vial was purged with argon and dry 1,4-dioxane (0.8 mL) was added followed by dipea (26 μL, 0.15 mmol) under stream of argon. Vial was sealed with a Teflon lined screw cap and the RM was heated to 90° C. After 15 h TLC (EA:Hex 1:1+2% Et$_3$N) indicated only partial conversion and additional Co$_2$(CO)$_8$ (8.0 mg, 23 μmol), NH$_4$Cl (8.0 mg, 0.15 mmol) and dipea (26 μL, 0.15 mmol) were added. Heating was continued for 24 h more (no further conversion was observed). RM was diluted with MeOH and adsorbed on celite. Compound was purified by column chromatography with gradient of EA:Hex 1:1+2% Et$_3$N with 5 to 10% MeOH. Product was further purified on PTLC in acetone:Hex 1:1+2% Et$_3$N and coeluting Et$_3$N salts were removed by washing of its CHCl$_3$ solution with 2M Na$_2$CO$_3$. Product 10 was obtained as a pale-yellow solid (6.5 mg, 35%).

Reaction was repeated from 34 (25 mg, 41 μmol), Pd(CAc)$_2$ (0.8 mg, 3.6 μmol), dppf (2.7 mg, 4.9 μmol), imidazole (0.9 mg, 13 μmol), Co$_2$(CO)e (9.7 mg, 28 μmol) and NH$_4$Cl (9.3 mg, 0.17 mmol) were balanced into an oven-dried vial. Vial was purged with argon and dry 1,4-dioxane (0.9 mL) was added followed by dipea (30 μL, 0.17 mmol) under a stream of argon. Vial was sealed with a Teflon lined screw cap and the RM was heated to 90° C. After 21.5 h TLC (EA:Hex 1:1+2% Et$_3$N) indicated full conversion, RM was diluted with MeOH and adsorbed on celite. Product was pre-separated by column chromatography in EA+2% Et$_3$N to acetone+2% Et$_3$N (compound is spreading and not separating very well). Product was further purified on PTLC in EA:acetone 2:1 t 2% Et$_3$N (2xxx developed). Compound was eluted from SiO$_2$ with acetone (no Et$_3$N) to prevent elution of Et$_3$N salt. Product 10 was obtained as a pale-yellow solid (11.7 mg, 57%).

$^1$H NMR (500 MHz, CDCl$_3$) δ 7.40 (s, 10), 6.94 (s, 1H), 6.66 (s, 1H), 5.79 (d, J=181.3 Hz, 2H), 4.41 (s, 1H), 3.98-3.85 (m, 4H), 3.19 (s, 4H), 3.70 (s, 4H), 3.43 (d, J=11.9 Hz, lii), 2.99 (d, J=11.3 Hz, 1H), 2.95-2.87 (m, 1H), 2.47 (t, J=11.8 Hz, 2H), 2.41-2.29 (m, 2H), 2.29-2.23 (m, 1H), 2.16 (d, J=17.7 Hz, 1H), 1.85-1.68 (m, 3H), 1.56 (d, J=11.3 Hz, 1H), 1.25 (s, 1H), 0.84 (t, J=7.3 Hz, 3H). $^{13}$C NMR (126 MHz, CDCl$_3$) δ 169.7, 169.2, 160.6, 157.2, 149.3, 135.7, 120.1, 111.8, 103.7, 103.3, 91.2, 81.3, 62.7, 61.8, 61.4, 60.8, 58.6, 55.8, 51.4, 50.2, 40.6, 40.2, 35.3, 24.3, 19.3, 13.2. LR-MS (APCI+) calcd. for C$_{26}$H$_{36}$N$_3$O$_7^+$ [M+H]$^+$: 502.3, found 502.6.

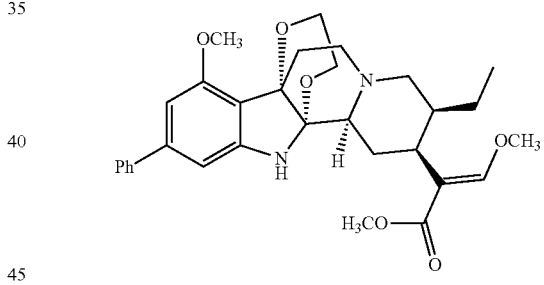

Compound 11 (11-phenyl-MG-EG).

Starting material 4 (20 mg, 37 μmol), phenylboronic acid (9.8 mg, 80 μmol), CsOAc (16.1 mg, 81 μmol) and Pd(dpf)Cl$_2$·CH$_2$Cl$_2$ (2.0 mg, 2.4 μmol) were balanced into an oven-dried vial. Vial was purged with argon and dry THF (0.3 mL) was added under a stream of argon. Vial was closed with a Teflon lined solid screw cap and heated to 70° C. After 7 h LR-MS and TLC indicated full consumption of starting material. RM was diluted with brine (5 mL) and extracted with DCM (3×5 mL). Combined DCM extracts were dried over Na$_2$SO$_4$ and evaporated. Crude residue was purified by PTLC (EA:Hex 1:4+2% Et$_3$N and Et$_2$O+1% Et$_3$N). Product 11 was obtained as a pale-yellow solid (16.1 mg, 81%).

$^1$H NMR (400 MHz, CDCl$_3$) δ 7.57-7.50 (m, 2H), 7.44-7.37 (m, 3H), 7.35-7.29 (m, 1H), 6.62-6.56 (m, 2H), 4.33 (s, 1H), 3.98-3.81 (m, 5H), 3.79 (s, 3H), 3.70 (s, 4H), 3.49-3.42 (m, 1H), 3.00 (dd, J=11.5, 2.1 Hz, 1H), 2.93 (dt, J=13.0, 3.6 Hz, 1H), 2.56-2.43 (m, 2H), 2.43-2.32 (m, 2H), 2.32-2.23 (m, 1H), 2.19 (dt, J=14.3, 2.5 Hz, 1H), 1.92-1.69 (m, 3H), 1.58 (d, J=11.1 Hz, 1H), 1.28-1.21 (m, 1H), 0.85 (t, J=7.4

Hz, 3H). $^{13}$C NMR (126 MHz, CDCl$_3$) 169.3, 160.6, 157.1, 149.5, 143.9, 142.0, 128.7, 127.3 (overlap of two aromatic carbons of the phenyl ring), 115.1, 111.8, 104.5, 102.6, 91.1, 81.4, 62.6, 61.8, 61.4, 61.0, 58.6, 55.5, 51.4, 50.4, 40.6, 40.3, 35.7, 24.3, 19.3, 13.2. LR-MS (APCI+) calcd. for C$_{31}$H$_{39}$N$_2$O$_6$$^+$ [M+H]$^+$: 535.3, found 536.0.

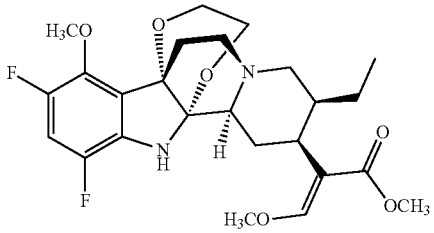

10,12-Difluoromitragynine-Ethylene Glycol Adduct:

11-tributyltinmitragynine-ethylene glycol adduct 6b (20 mg, 26.7 μmol), F-TEDA-PF$_6$ (34.8 mg, 106 μmol), AgOTf (13.7 mg, 53.4 μmol) and NaHCO$_3$ (6.7 mg, 80.1 μmol) were combined in a vial and dry acetone (0.6 mL) was added. The RM was stirred at 50° C. for 20 mins and additional F-TEDA-PF$_6$ (17.9 mg, 53 μmol) was added. After 90 mins the RM was cooled down to room temperature and diluted with water and extracted with DCM (3×5 mL). Combined DCM extracts were washed with brine, dried over Na$_2$SO$_4$ and evaporated. The product was purified by PTLC using EtOAc:Hex 1:5+2% Et$_3$N and obtained as an amorphous light brown powder (2.6 mg, 20%).

$^1$H NMR (500 MHz, CDCl$_3$) 7.42 (s, 1H), 6.73 (dd, J=11.8, 9.4 Hz, 1H), 4.21 (s, 1H), 3.98 (d, J=2.1 Hz, 1h), 3.95 (d, J=1.8 Hz, 3H), 3.88-3.83 (m, 1H), 3.79 (s, 3H), 3.73 (d, J=2.7 Hz, 1H), 3.71-3.69 (m, 3H), 3.45 (dd, J=11.8, 2.6 Hz, 1H), 3.13-3.07 (m, 1H), 3.00 (dd, J=11.5, 2.3 Hz, 1H), 2.91 (dt, J=13.1, 3.6 Hz, 1H), 2.54-2.48 (m, 1H), 2.45 (dd, J=11.5, 2.0 Hz, 1H), 2.34 (t, J=12.4 Hz, 2H), 2.26 (dd, J=11.9, 3.0 Hz, 1H), 2.15-2.09 (m, 1H), 1.86 (td, J=13.8, 4.3 Hz, 1H), 1.77 (d, J=12.4 Hz, 15), 1.74-1.67 (m, 1H), 1.22 (s, 1H), 0.84 (d, J=7.4 Hz, 3H). LRMS (APCI+) calcd. for C$_{25}$H$_{33}$F$_2$N$_2$O$_6$$^+$ [M+H]$^+$: 495.2, found 495.4.

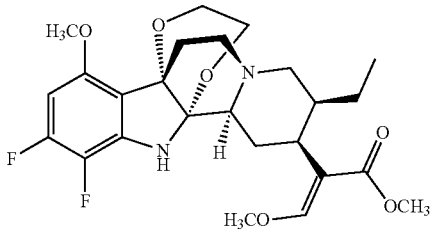

11,12-Difluoromitragynine-Ethylene Glycol Adduct:

11-Fluoromitragynine-ethylene glycol adduct 2 (6 mg, 12.6 μmol) and F-TEDA-BF$_4$ (4.1 mg, 12.6 μmol) were dissolved in anhydrous acetone (0.4 mL) in a vial and the RM was stirred at 50° C. After 10 min additional F-TEDA-BF$_4$ (8.2 mg, 25.2 μmol) was added. After 45 min the RM was evaporated to dryness and the product was purified by PTLC using EtOAc:Hex 1:5+2% Et$_3$N and obtained as an amorphous yellow powder (1.5 mg, 24%)

$^1$H NMR (500 MHz, CDCl$_3$) δ 7.41 (s, 1H), 6.18-6.05 (m, 1H), 4.19 (s, 1H), 4.02 (d, J=2.7 Hz, 35), 3.93 (d, J=17.8 Hz, 1H), 3.81-3.78 (m, 4H), 3.72-3.68 (m, 4ll), 3.43 (d, J=11.7 Hz, 1H), 2.99 (d, J 11.5 Hz, 1H), 2.91 (d, J=13.0 Hz, 1H), 2.51-2.39 (m, 25), 2.28 (dd, J=33.6, 13.1 Hz, 3H), 2.11 (d, J=14.0 Hz, 1H), 1.84-1.68 (m, 3H), 1.53 (s, 1H), 1.23 (s, 1H), 0.84 (t, J=6.7 Hz, 3H). LRMS (APCI+) calcd. for C$_{25}$H$_{33}$F$_2$N$_2$O$_6$$^+$ [M+H]$^+$: 495.2, found 495.4.

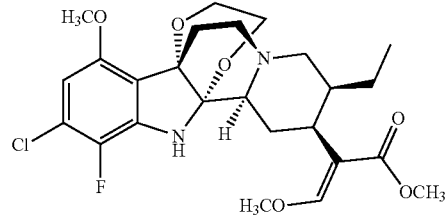

11-Chloro-12-Fluoromitragynine-Ethylene Glycol Adduct:

C11-Chloromitragynine-ethylene glycol adduct 3 (10 mg, 20.2 μmol) and F-TEDA-BF$_4$ (6.5 mg, 20.2 μmol) were dissolved in anhydrous acetone (0.6 mL) in a vial and the RM was stirred at 50° C. After 10 min additional F-TEDA-BF$_4$ (13 mg, 40.4 μmol) was added and stirring continued. After 45 min the RM was evaporated to dryness and the product was purified by PTLC using EtOAc:Hex 1:5+2% Et$_3$N and obtained as an amorphous yellow powder (2 mg, 20%).

$^1$H NMR (500 MHz, CDCl$_3$) δ 7.42 (s, 1H), 6.64-6.24 (m, 1H), 4.21 (s, 1H), 4.00 (d, J=2.5 Hz, 3H), 3.92-3.83 (m, 1H), 3.83-3.78 (m, 4H), 3.75-3.66 (m, 4H), 3.44 (d, J=8.6 Hz, 1H), 2.95 (d, J=37.5 Hz, 2H), 2.46 (d, J=27.6 Hz, 2H), 2.38-2.22 (m, 3H), 2.19-2.07 (m, 1H), 1.75 (s, 3H), 1.56-1.49 (m, 1H), 1.20-1.11 (m, 1H), 0.87-0.83 (m, 3H). LAMS (APCI+) calcd. for C$_{25}$H$_{33}$ClFN$_2$O$_6$$^+$ [M+H]$^+$: 511.2, found 511.3.

Deprotection of Mitragynine-Ethylene Glycol Adduct Derivatives

General procedure: Reactions were performed according to procedure described for C10 isomers (Takayama, H. 2006).

Starting material (0.11 mmol) was dissolved in AcOH (2.0 mL) under argon and NaCNBH$_3$ (13.7 mg, 0.22 mmol) was added to the solution. After stirring at RT for 15 min another portion of NaCNBH$_3$ (13.7 mg, 0.22 mmol) was added and the stirring continued for 1 h. After this time MeOH (81 μL) was added and the RM was heated to 90° C. for 14 h. RM was added into a cold concentrated NH$_4$OH solution and extracted with DCM. After drying over Na$_2$SO$_4$, the DCM extract was evaporated. Product was purified by PTLC using an appropriate solvent mixture as described for each derivative.

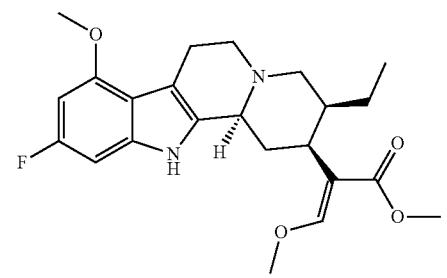 [SMILES: CC[C@@H]1CN2CCc3c([nH]c4cc(F)cc(OC)c34)[C@@H]2C[C@@H]1/C(=C\OC)C(=O)OC]

Compound 13 (11-fluoro-MG).

Reaction was performed according to the general procedure. Crude material was purified by PTLC using EA:Hex 1:4+2% Et$_3$N. Product 13 was obtained as a yellow solid (32 mg, 70%)

$^1$H NMR (500 MHz, CDCl$_3$) δ 7.74 (s, 1H), 7.43 (s, 1H), 6.59 (dd, J=9.3, 2.0 Hz, 1H), 6.26 (dd, J 11.8, 2.0 Hz, 1H), 3.84 (s, 3H), 3.73 (s, 3H), 3.70 (s, 3H), 3.18-2.97 (m, 4H), 2.96-2.83 (m, 2H), 2.62-2.36 (m, 3H), 1.84-1.73 (m, 2H), 1.69-1.55 (m, 1H), 1.29-1.16 (m, 1H), 0.86 (t, J=7.4 Hz, 3H). $^{13}$C NMR (126 MHz, CDCl$_3$) δ 169.3, 160.7, 160.2 (d, J=235.1 Hz), 154.7 (d, J=12.4 Hz), 136.2 (d, J 15.2 Hz), 133.8 (d, J=3.3 Hz), 114.1, 111.6, 108.0, 90.4 (d, J=26.4 Hz), 90.2 (d, J=28.7 Hz), 61.7, 61.3, 57.9, 55.6, 53.8, 51.5, 40.8, 40.0, 30.1, 23.9, 19.2, 13.0. LR-MS (APCI+): calcd. for C$_{23}$H$_{30}$FN$_2$O$_4^+$ [M+H]$^+$: 417.2, found 417.6.

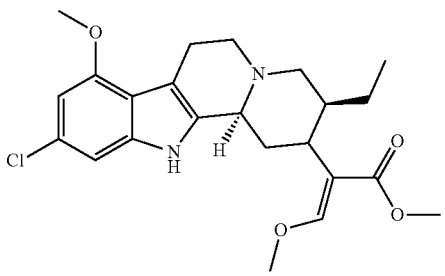 [SMILES: CC[C@@H]1CN2CCc3c([nH]c4cc(Cl)cc(OC)c34)[C@@H]2CC1/C(=C\OC)C(=O)OC]

Compound 14 (11-chloro-MG).

Reaction was performed according to the general procedure. Crude material was purified by PTLC using EA:Hex 1:4+2% Et$_3$N. Product 14 was obtained as a yellow solid (42 mg, 70%).

$^1$H NMR (400 MHz, CDCl$_3$) δ 7.84 (s, 1H), 7.42 (s, 1H), 6.89 (d, J=1.6 Hz, 1H), 6.43 (d, J=1.5 Hz, 1H), 3.85 (s, 3H), 3.72 (s, 3H), 3.70 (s, 3H), 3.15-2.97 (m, 4H), 2.95-2.86 (m, 2H), 2.61-2.33 (m, 3H), 1.85-1.70 (m, 2H), 1.66-1.57 (m, 1H), 1.32-1.16 (m, 1H), 0.86 (t, J=7.4 Hz, 3H). $^{13}$C NMR (101 MHz, CDCl$_3$) δ 169.3, 160.7, 154.6, 137.1, 134.3, 127.2, 116.5, 111.6, 108.2, 104.5, 101.4, 61.7, 61.3, 57.9, 55.6, 53.8, 51.5, 45.7, 40.8, 40.0, 23.8, 19.3, 13.0. LR-MS (APCI+) calcd. for C$_{23}$H$_{30}$ClN$_2$O$_4^+$ [M+H]$^+$: 433.2, found 433.3.

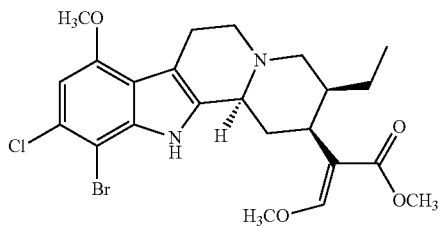 [SMILES: CC[C@@H]1CN2CCc3c([nH]c4c(Br)c(Cl)cc(OC)c34)[C@@H]2C[C@@H]1/C(=C\OC)C(=O)OC]

11-Chloro-12-bromomitragynine:

11-Chloromitragynine (14) (20 mg, 50 μmol) and NBS (9 mg, 50 μmol) were dissolved in anhydrous CH$_2$Cl$_2$ (0.5 mL) in a vial under Argon. The reaction mixture was cooled to 0° C. and TFA (0.1 mL, 5.7 μmol) was added. The reaction was continued for 2 h at 0° C. until LRMS and TLC indicated complete consumption of SM. The reaction mixture was quenched with saturated aq. NaHCO$_3$ and extracted with EtOAc (3×5 mL). Combined EtOAc extracts were dried over Na$_2$SO$_4$ and evaporated. The product was purified by PTLC using EtOAc:Hex 1:4+2% Et$_3$N and obtained as an amorphous yellow powder (11 mg, 43%).

$^1$H NMR (500 MHz, CDCl$_3$) δ 7.84 (s, 1H), 7.44 (s, 1H), 6.55 (s, 1H), 3.84 (s, 3H), 3.75 (s, 3H), 3.70 (s, 3H), 3.18-3.11 (m, 1H), 3.11-2.97 (m, 3H), 2.94-2.85 (m, 2H), 2.55-2.42 (m, 3H), 1.83 (dt, J=12.6, 3.1 Hz, 1H), 1.80-1.71 (m, 1H), 1.62 (t, J=6.6 Hz, 1H), 1.20 (dt, J=9.2, 3.4 Hz, 1H), 0.86 (t, J=7.3 Hz, 3H). LRMS (APCI+) calcd. for C$_{23}$H$_{29}$BrClN$_2$O$_4^+$ [M+H]$^+$: 511.1, found 511.2.

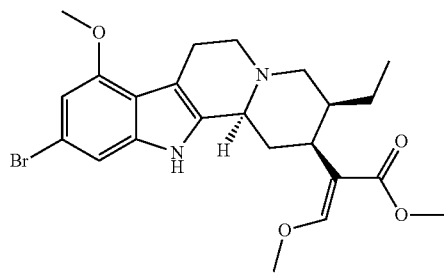 [SMILES: CC[C@@H]1CN2CCc3c([nH]c4cc(Br)cc(OC)c34)[C@@H]2C[C@@H]1/C(=C\OC)C(=O)OC]

Compound 15 (11-bromo-MG).

Reaction was performed according to the general procedure. Crude material was purified by PTLC using EA:Hex 1:4+2% Et$_3$N. Product 15 was obtained as a yellow solid (35 mg, 78%).

$^1$H NMR (500 MHz, CDCl$_3$) δ 7.77 (s, 1H), 7.43 (s, 1H), 7.05 (d, J=1.4 Hz, 1H), 6.55 (d, J=1.5 Hz, 1H), 3.85 (s, 3H), 3.73 (s, 3H), 3.71 (s, 3H), 3.14-2.97 (m, 4H), 2.94-2.87 (m, 2H), 2.55-2.41 (m, 3H), 1.83-1.71 (m, 2H), 1.62 (dd, J=8.6, 5.3 Hz, 1H), 1.24-1.15 (m, 1H), 0.86 (t, J=7.4 Hz, 3H). $^{13}$C NMR (126 MHz, CDCl$_3$) δ 169.3, 160.7, 154.7, 137.5, 134.3, 116.8, 114.5, 111.5, 108.3, 107.4, 104.0, 61.7, 61.2, 57.9, 55.7, 53.8, 51.5, 40.8, 40.0, 30.0, 23.9, 19.2, 13.0. LR-MS (APCI+) calcd. for C$_{23}$H$_{30}$BrN$_2$O$_4^+$ [M+H]$^+$: 477.2, found 477.4.

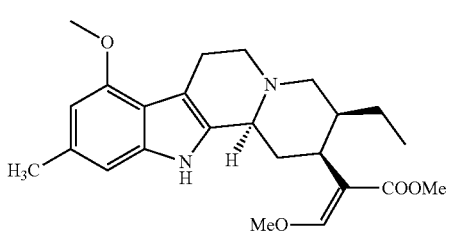 [SMILES: CC[C@@H]1CN2CCc3c([nH]c4cc(C)cc(OC)c34)[C@@H]2C[C@@H]1/C(=C\OC)C(=O)OC]

Compound 18 (11-methyl-MG).

Starting material (25 mg, 53 μmol) was dissolved in AcOH (1.0 mL) under argon and NaCNBH$_3$ (5 mg, 79 μmol) was added to the solution. After stirring at RT for 30 min the SM was fully consumed. RM was added into a cold concentrated NH$_4$OH solution and extracted with DCM. After drying over Na$_2$SO$_4$, the DCM extract was evaporated. Crude material was purified by PTLC using EA:Hex 1:4+2% Et$_3$N. Product 18 was obtained as a yellow solid (15 mg, 70%).

$^1$H NMR (500 MHz, CDCl$_3$) δ 7.53 (s, 1H), 7.43 (s, 1H), 6.69 (d, J=1.0 Hz, 1H), 6.28 (d, J=1.1 Hz, 1H), 3.85 (s, 3H), 3.72 (s, 3H), 3.70 (s, 3H), 3.15-2.98 (m, 4H), 2.96-2.88 (m, 2H), 2.56-2.42 (m, 3H), 2.40 (s, 3H), 1.82-1.73 (m, 2H), 1.65-1.58 (m, 1H), 1.23-1.17 (m, 1H), 0.86 (t, J=7.4 Hz, 3H). $^{13}$C NMR (126 MHz, CDCl$_3$) δ 169.4, 160.6, 154.3, 137.7, 133.1, 132.0, 115.7, 111.7, 107.8, 104.2, 101.8, 61.7, 61.4, 57.9, 55.4, 54.0, 51.5, 40.9, 40.1, 30.1, 24.0, 22.2, 19.3, 13.0. LR-MS (APCI+): calcd. for $C_{24}H_{33}N_2O_4^+$ [M+H]$^+$: 413.2, found 413.8.

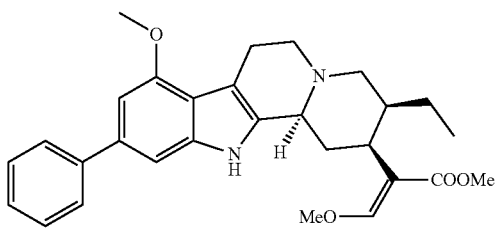 [SMILES: CC[C@@H]1CN2CCc3c([nH]c4cc(-c5ccccc5)cc(OC)c34)[C@@H]2C[C@@H]1/C(=C\OC)C(=O)OC]

Compound 22 (11-phenyl-MG).

Starting material (16 mg, 30 µmol) was dissolved in AcOH (0.6 mL) under argon and NaCNBH$_3$ (3.8 mg, 60 µmol) was added to the solution. After stirring at RT for 15 min another portion of NaCNBH$_3$ (3.8 mg, 60 µmol) was added and the stirring continued for 3h. RM was added into a cold concentrated NH$_4$OH solution and extracted with DCM. After drying over Na$_2$SO$_4$, the DCM extract was evaporated. Crude material was purified by FTLC using EA:Hex 1:4+2% Et$_3$N. Product 22 was obtained as a yellow solid (5 mg, 35%).

$^1$H NMR (500 MHz, CDCl$_3$) δ 7.73 (s, 1H); 7.65-7.57 (m, 2H), 7.44 (s, 1H), 7.43-7.39 (m, 2H), 7.32-7.27 (m, 1H), 7.12 (d, J=1.2 Hz, 1H), 6.70 (d, J=1.2 Hz, 1H), 3.94 (s, 3H), 3.74 (s, 3H), 3.71 (s, 3H), 3.22-3.08 (m, 2H), 3.07-2.97 (m, 3H), 2.97-2.90 (m, 1H), 2.59-2.50 (m, 2H), 2.49-2.41 (m, 1H), 1.87-1.74 (m, 1H), 1.69-1.58 (m, 2H), 1.24-1.20 (m, 1H), 0.87 (t, J=7.4 Hz, 3H). $^{13}$C NMR (126 MHz, CDCl$_3$) δ 169.4, 160.7, 154.6, 143.0, 137.8, 135.8, 134.6, 128.7, 127.5 (overlap of two aromatic carbons of the phenyl ring), 126.6, 117.2, 111.7, 108.1, 103.2, 100.1, 61.7, 61.5, 58.0, 55.6, 53.9, 51.5, 40.9, 40.1, 30.1, 24.0, 19.3, 13.0. LR-MS (APCI+): calcd. for $C_{29}H_{35}N_2O_4^+$ [M+H]$^+$: 475.3, found 475.8.

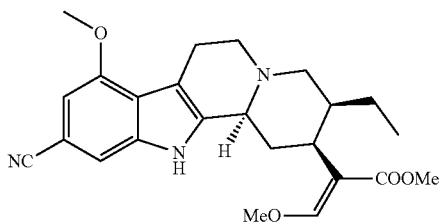 [SMILES: CC[C@@H]1CN2CCc3c([nH]c4cc(C#N)cc(OC)c34)[C@@H]2C[C@@H]1/C(=C\OC)C(=O)OC]

Compound 19 (11-cyano-MG).

Starting material (44 mg, 1 µmol) was dissolved in AcOH (0.8 mL) under argon and NaCNBH$_3$ (11.4 mg, 0.18 mmol) was added to the solution. After stirring at RT for 15 min another portion of NaCNBH$_3$ (21 mg, 0.33 mmol) was added and the stirring continued at 50° C. for 18 hrs. RM was added into a cold concentrated NH$_4$OH solution and extracted with DCM. After drying over Na$_2$SO$_4$, the DCM extract was evaporated. Crude material was purified by PTLC using EA:Hex 1:4+2% Et$_3$N. Product 19 was obtained as a yellow solid (13 mg, 34%).

$^1$H NMR (500 MHz, CDCl$_3$) δ 8.16 (s, 1H), 7.43 (s, 1H), 7.27 (d, J=1.2 Hz, 1H), 6.62 (d, J=1.2 Hz, 1H), 3.89 (s, 3H), 3.73 (s, 3H), 3.71 (s, 3H), 3.16 (dd, J=11.5, 2.3 Hz, 1H), 3.11-2.99 (m, 3H), 2.97-2.88 (m, 2H), 2.58-2.48 (m, 2H), 2.47-2.41 (m, 1H), 1.83 (dt, J=12.8, 3.1 Hz, 1H), 1.79-1.69 (m, 1H), 1.67-1.60 (m, 1H), 1.25-1.14 (m, 1H), 0.87 (t, J=7.3 Hz, 3H). $^{13}$C NMR (126 MHz, CDCl$_3$) δ 169.3, 160.8, 154.4, 138.0, 135.9, 121.3, 121.3, 111.4, 110.1, 109.3, 103.6, 102.2, 61.8, 61.3, 57.8, 55.7, 53.6, 51.6, 40.7, 40.0, 29.9, 23.7, 19.2, 13.0. LR-MS (APCI+): calcd. for $C_{24}H_{30}N_3O_4^+$ [M+H]$^+$: 424.2, found 424.8.

Oxidation of Mitragynine Derivatives in the 7-Position

General procedure: Starting material (73 µmol) was dissolved in acetone (2.2 mL). Sat. aq. NaHCO$_3$ was added and the stirred suspension was cooled in ice bath (0° C.). Oxone (94.5 µmol, 1.3-1.5 equivalents) in H$_2$O (0.7 mL) was added dropwise over 20 min. The reaction was monitored during the addition of oxone by TLC. After 25 min from the first addition the RM was diluted with H$_2$O (10 mL) and extracted 3×10 mL EA. Combined extracts were washed with brine (10 mL), dried over Na$_2$SO$_4$ and concentrated. Product was purified by PTLC using an appropriate solvent mixture as described for each derivative.

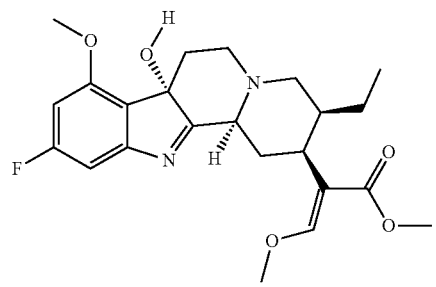 [SMILES: CC[C@@H]1CN2CC[C@@]3(O)C(=Nc4cc(F)cc(OC)c43)[C@@H]2C[C@@H]1/C(=C\OC)C(=O)OC]

Compound 24 (11-fluoro-7-OH).

Reaction was performed according to the general procedure. Crude material was purified by a repeated PTLC (EA:Hex 1:3+2% Et$_3$N and EA:Hex 3:7+2% Et$_3$N). Product 24 was obtained as a yellow solid (13 mg, 52%).

$^1$H NMR (400 MHz, CDCl$_3$) δ 7.43 (s, 1H), 6.91 (dd, J=8.5, 2.0 Hz, 1H), 6.45 (dd, J=11.3, 2.0 Hz, 1H), 3.84 (s, 3H), 3.80 (s, 3H), 3.69 (s, 3H), 3.12 (dd, J=11.1, 2.6 Hz, 1H), 3.06-2.96 (m, 2H), 2.91-2.73 (m, 3H), 2.66-2.56 (m, 2H), 2.51-2.43 (m, 1H), 1.89-1.82 (m, 1H), 1.73-1.53 (m, 3H), 1.30-1.14 (m, 1H), 0.82 (t, J=7.3 Hz, 3H). $^{13}$C NMR (126 MHz, CDCl$_3$) 186.2, 169.4, 165.0 (d, J=245.2 Hz), 160.9, 156.2 (d, J=11.8 Hz), 156.1 (d, J=13.1 Hz), 122.3, 111.4, 102.2 (d, J=24.4 Hz), 97.1 (d, J=27.4 Hz), 80.9, 61.9, 61.6, 58.3, 55.9, 51.5, 50.1, 40.6, 39.4, 36.1, 26.1, 19.1, 13.0. LR-MS (APCI+) calcd. for $C_{23}H_{30}FN_2O_5^+$ [M+H]$^+$: 433.2, found 433.

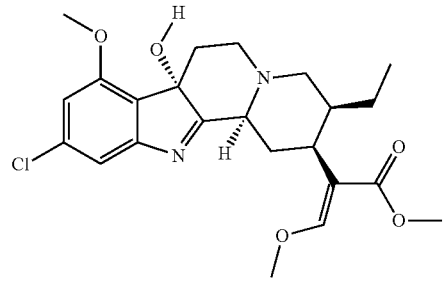

Compound 25 (11-chloro-7-OH).

Reaction was performed according to the general procedure. Crude material was purified by a repeated PTLC (EA:Hex 1:3+2% Et₃N and EA:Hex 3:7+2% Et₃N). Product 25 was obtained as a yellow solid (20.7 mg, 50%).

¹H NMR (400 MHz, CDCl₃) δ 7.44 (s, 1H), 7.21 (d, J=1.5 Hz, 1H), 6.73 (d, J=1.5 Hz, 1H), 3.86 (s, 3H), 3.81 (s, 3H), 3.70 (s, 3H), 3.14-2.97 (m, 3H), 2.93 (d, J=7.4 Hz, 1H), 2.87-2.72 (m, 2H), 2.70-2.55 (m, 2H), 2.48 (dd, J=11.5, 3.0 Hz, 1H), 1.86 (d, J=13.7 Hz, 1H), 1.75-1.54 (m, 3H), 1.33-1.17 (m, 1H), 0.82 (t, J=7.3 Hz, 3H). ¹³C NMR (126 MHz, CDCl₃) δ 185.8, 169.3, 160.7, 155.8, 135.9, 125.1, 115.0, 111.2, 109.6, 80.9, 61.8, 61.5, 58.1, 55.8, 51.3, 49.9, 45.7, 40.5, 39.2, 35.8, 26.0, 18.9, 12.8. LR-MS (APCI+) calcd. for $C_{23}H_{30}ClN_2O_5^+$ [M+H]⁺: 449.2, found 449.1.

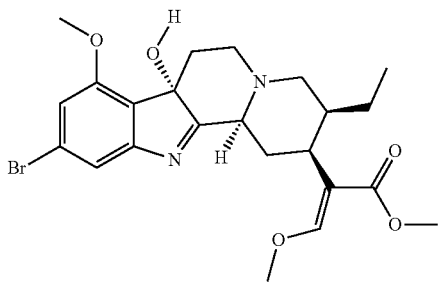 [SMILES: CC[C@@H]1CN2CC[C@@]3(O)C(=Nc4cc(Cl)cc(OC)c43)[C@@H]2C[C@@H]1/C(=C\OC)C(=O)OC]

Compound 26 (11-bromo-7-OH).

Reaction was performed according to the general procedure. Crude material was purified by a repeated PTLC (EA:Hex 1:3+2% Et₃N and EA:Hex 3:7+2% Et₃N). Product 26 was obtained as a yellow solid (16.1 mg, 45%).

¹H NMR (400 MHz, CDCl₃) δ 7.43 (s, 1H), 7.34 (d, J=1.3 Hz, 1H), 6.87 (d, J=1.3 Hz, 1H), 3.86 (s, 31), 3.80 (s, 3H), 3.69 (s, 3H), 3.15-2.96 (m, 3H), 2.84-2.71 (m, 2H), 2.65-2.56 (m, 2H), 2.51-2.44 (m, 1H), 2.30 (s, 1H), 1.85 (dt, J=13.7, 3.1 Hz, 1H), 1.73-1.56 (m, 3H), 1.30-1.18 (m, 1H), 0.82 (t, J=7.3 Hz, 3H). ¹³C NMR (126 MHz, CDCl₃) δ 186.0, 169.4, 160.9, 156.1, 156.1, 125.8, 123.6, 118.0, 112.6, 111.3, 81.1, 61.9, 61.7, 58.3, 56.0, 51.4, 50.0, 40.6, 39.4, 35.8, 26.1, 19.1, 13.0. LR-MS (APCI+) calcd. for $C_{23}H_{30}BrN_2O_5^+$ [M+H]⁺: 493.1, found 493.7.

Other derivatives 27-33 are prepared accordingly.

C—H Borylation Reaction (Selectivity C11:C12=1.3-1.1:1) of 1 and Subsequent Transformations General procedure: Starting material 1 (25 mg, 55 μmol), [Ir(COD)OMe]₂ (1.8 mg, 2.7 μmol), 4,4'-di-tert-butyl-2,2'-dipyridyl (2.2 mg, 8.1 μmol) and B₂Pin₂ (55 mg, 0.22 mmol) were balanced into an oven dried vial. Vial was purged with argon and dry heptane (1 mL) was added under argon. Vial was sealed with Teflon lined screw cap and heated to 65° C. RM becomes a dark brown solution after 5-15 minutes of heating. After 15-24 h when LR-MS indicated complete consumption of SM the RM was concentrated to dryness on rotavap (RM is prone to bumping, if necessary MeOH can be used to wash down any material that splashed). This intermediate was immediately used to prepare the mixture of —Br derivatives 4 and 47.

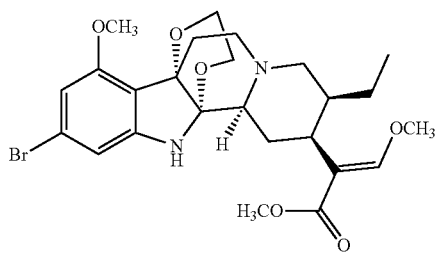

-continued

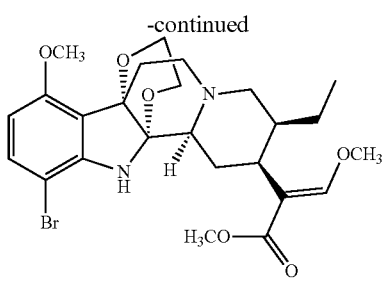

To the dark residue of intermediate was added CuBr₂ (37 mg, 0.17 mmol) and a mixture of MeOH+H₂O (2+0.5 mL). Vial was sealed, and the RM was then heated to 80° C. with vigorous stirring (slower stirring will cause incomplete conversion due to a precipitation of reactants during the reaction). After 15 h, TLC (EA:Hex 1:1+2% Et₃N) and LR-MS indicated complete conversion of the intermediate. RM was diluted with brine (15 mL) and extracted with DCM (3×5 mL). Combined DCM extracts were dried over Na₂SO₄ and evaporated. Product was purified by PTLC using EA:Hex 1:4+2% Et₃N. Plate was developed twice. Products 4 and 47 were obtained as an inseparable mixture (C11:C12 53:47) in the form of pale-yellow solid (20-24 mg, 60-83%).

¹H NMR (400 MHz, CDCl₃) (Partial integrals due to a presence of two regioisomers) δ 7.42 (s, 0.47H), 7.40 (s, 0.53H), 7.20 (d, 3=8.8 Hz, 0.42H), 6.53 (s, 1.1H), 6.31 (d, J=8.8 Hz, 0.43H), 4.40 (s, 0.43H), 4.29 (s, 0.57H), 3.96-3.87 (m, 1H), 3.82 (d, J=1.2 Hz, 3H), 3.79 (d, J=1.4 Hz, 4H), 3.72-3.63 (m, 4H), 3.45-3.38 (m, 1H), 3.02-2.86 (m, 2H), 2.52-2.41 (m, 2H), 2.40-2.29 (m, 2H), 2.26 (dd, J=11.7, 4.1 Hz, 1H), 2.18-2.09 (m, 1H), 1.87-1.67 (m, 3H), 1.58 (s, 1H), 1.24 (s, 1H), 0.89-0.80 (m, 3H). LR-MS (APCI+) calcd. for $C_{25}H_{34}BrN_2O_5^+$ [M+H]⁺: 537.2, found 537.2.

C—H Borylation Reaction (C12 Selective) of 12 and Subsequent Transformations

General procedure: Catalyst [Ir(COD)OMe]₂ (4 mg, 6.0 μmol) was dissolved in dry heptane (2.8 mL) in an oven dried vial under argon and HBPin (73 μL, 0.50 mmol), 4,4'-di-tert-butyl-2,2'-dipyridyl (3.1 mg, 12 μmol) and starting material 12 (49 mg, 0.12 mmol) were added under stream of argon consecutively with a 2 min stirring period at RT between each addition. Vial was sealed with a Teflon lined screw cap and heated to 65° C., RM is a dark red-brown mixture. After 15-24 h when LR-MS and TLC (on alumina) indicated complete consumption of SM the RM was concentrated to dryness on rotavap (RM is prone to bumping, if necessary MeOH can be used to wash down any material that splashed). This intermediate was immediately used to prepare the —Cl 69 and —Br 70 derivatives without further purification.

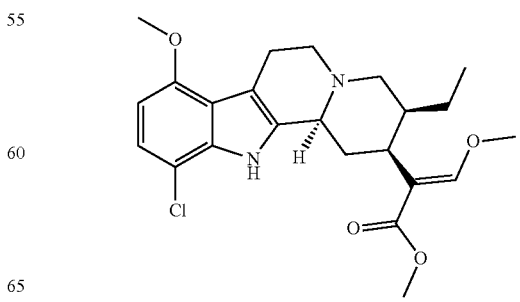

Compound 69 (12-chloro-MG-EG).

To the dark residue of intermediate was added CuCl$_2$·H$_2$O (75 mg, 0.44 mmol) and a mixture of MeOH+H$_2$O (4+1 mL). Vial was sealed, and the RM RM was then heated to 80° C. with vigorous stirring (slower stirring will cause incomplete conversion due to a precipitation of reactants during the reaction). After 12 h, TLC (EA:Hex 1:1+2% Et$_3$N) and LR-MS indicated complete conversion of the intermediate. Crude reaction mixture was adsorbed on silica and purified by column chromatography using EA:Hex 1:9+5% Et$_3$N. Product 69 was obtained in the form of yellow solid (31 mg, 61%).

$^1$H NMR (400 MHz, CDCl$_3$) δ 7.84 (s, 1H), 7.44 (s, 1H), 6.97 (d, J=8.3 Hz, 1H), 6.38 (d, J=8.3 Hz, 1H), 3.86 (s, 3H), 3.75 (s, 3H), 3.72 (s, 3H), 3.16 (dt, J=11.8, 2.4 Hz, 1H), 3.13-2.99 (m, 3H), 2.97-2.88 (m, 2H), 2.58-2.42 (m, 3H), 1.85 (dt, J=13.0, 3.1 Hz, 1H), 1.82-1.72 (m, 1H), 1.67-1.59 (m, 1H), 1.25-1.16 (m, 1H), 0.88 (t, J=7.4 Hz, 3H). $^{13}$C NMR (101 MHz, CDCl$_3$) δ 169.3, 160.7, 153.5, 134.6, 134.0, 120.8, 118.9, 111.6, 109.4, 108.8, 100.7, 77.2, 61.7, 61.4, 57.9, 55.7, 53.7, 51.5, 40.8, 40.0, 30.0, 23.9, 19.3, 13.0. LR-MS (APCI+) calcd. for C$_{23}$H$_{30}$ClN$_2$O$_4{}^+$ [M+H]$^+$: 433.2, found 433.3.

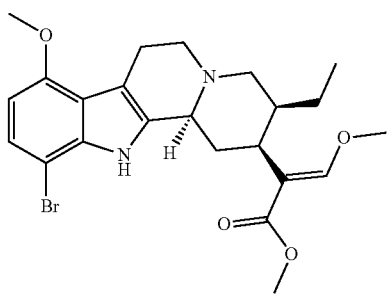 [SMILES: CC[C@@H]1CN2CCc3c([nH]c4c(Cl)ccc(OC)c34)[C@@H]2C[C@@H]1/C(=C\OC)C(=O)OC]

Compound 70 (12-bromo-MG-EG).

To the dark residue of intermediate was added CuBr$_2$ (84 mg, 0.38 mmol) and a mixture of MeOH+H$_2$O (4+1 mL). Vial was sealed, and the RM was then heated to 80° C. with vigorous stirring (slower stirring will cause incomplete conversion due to a precipitation of reactants during the reaction). After 12 h, TLC (EA:Hex 1:1+2% Et$_3$N) and LR-MS indicated complete conversion of the intermediate. Crude reaction mixture was adsorbed on silica and purified by column chromatography using EA:Hex 1:9+5% Et$_3$N. Product 70 was obtained in the form of pale-yellow solid (41 mg, 70%).

$^1$H NMR (500 MHz, CDCl$_3$) δ 7.78 (s, 1H), 7.45 (s, 1H), 7.11 (d, J=8.3 Hz, 1H), 6.36 (d, J=8.3 Hz, 1H), 3.85 (s, 3H), 3.75 (s, 3H), 3.71 (s, 3H), 3.16 (dd, J=11.3, 2.5 Hz, 1H), 3.13-2.99 (m, 3H), 2.96-2.88 (m, 2H), 2.57-2.43 (m, 3H), 1.85 (dt, J=13.0, 3.2 Hz, 1H), 1.82-1.72 (m, 1H), 1.63 (dd, J=8.8, 5.5 Hz, 1H), 1.28-1.17 (m, 1H), 0.87 (t, J=7.4 Hz, 3H). $^{13}$C NMR (126 MHz, CDCl$_3$) δ 169.3, 160.7, 154.1, 135.3, 134.5, 123.7, 118.8, 111.5, 109.6, 101.4, 96.2, 61.8, 61.4, 57.9, 55.7, 53.7, 51.5, 40.9, 40.0, 30.0, 24.0, 19.3, 13.0. LR-MS (APCI+) calcd. for C$_{23}$H$_{30}$BrN$_2$O$_4{}^+$ [M+H]$^+$: 477.2, found 477.4.

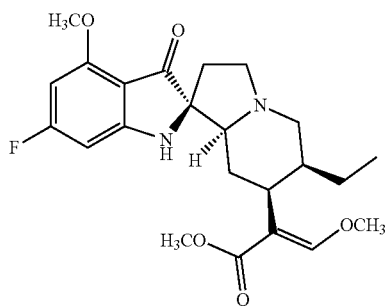 [SMILES: CC[C@@H]1CN2CC[C@]3(Nc4cc(F)cc(OC)c4C3=O)[C@@H]2C[C@@H]1/C(=C\OC)C(=O)OC]

11-Fluoromitragynine Pseudoindoxyl (36):

11-Fluoro-7-hydroxymitragynine (24) (18 mg, 43.4 μmol) was dissolved in anhydrous toluene (1 mL) in a vial under Argon. Zn(OTf)$_2$ (31.5 mg, 86.8 μmol) was added to the solution and the RM was stirred at 105° C. After 2 hrs the reaction mixture was cooled down to room temperature and quenched with saturated aq. NaHCO$_3$ and extracted with EtOAc (3×5 mL). Combined EtOAc extracts were dried over Na$_2$SO$_4$ and evaporated. The product was purified by PTLC using EtOAc:Hex 1:1+2% Et$_3$N and obtained as an amorphous yellow powder (11 mg, 40%).

$^1$H NMR (500 MHz, CDCl$_3$) δ 7.29 (s, 1H), 6.08 (dd, J=9.5, 1.9 Hz, 1H), 5.87 (dd, J=11.7, 1.9 Hz, 1H), 5.51 (s, 1H), 3.87 (s, 3H), 3.69 (s, 3H), 3.63 (s, 3H), 3.16 (d, J=11.5 Hz, 2H), 2.78 (dt, J=12.3, 3.4 Hz, 1H), 2.41-2.29 (m, 2H), 2.29-2.14 (m, 3H), 1.92 (s, 1H), 1.63 (s, 1H), 1.53 (s, 1H), 1.22-1.12 (m, 2H), 0.85 (t, J=7.3 Hz, 3H). LRMS (APCI+) calcd. for C$_{23}$H$_{30}$FN$_2$O$_5{}^+$ [M+H]$^+$: 433.2, found 432.5.

Any additional compounds described in Schemes 5-13 are prepared according to methods analogous to those described above.

Example 2. Cell-Based Functional Assays (BRET Assays)

The C11 derivatives of mitragynine, 7-hydroxymitragynine (7-OH), and mitragynine-ethylene glycol adduct (MG-EG) are novel molecular entities that show unexpected pharmacology at the opioid receptors (no prior art would enable those knowledgeable in the field predict the observed changes in modulation of the opioid receptors). The noted compounds were investigated in BRET functional assays for G protein activation as described previously (Kruegel et al, 2016).

It was previously shown that mitragynine (12) acts as a partial agonist at hMOR (Kruegel, et al. 2016), however after substitution with fluorine in the 11-position (compound 13) both the efficacy and potency increased substantially for the new analog (FIG. 1. E$_{max}$=49.05% and EC$_{50}$=81.55 nM [45.10, 147.50], Table 1). in contrast, the chloro derivative (14) showed decreased efficacy compared to the fluoro compound, and similar to that of the parent mitragynine. Continuing in the halogen series to the bromo derivative (15), this compound shows no/negligible agonist activity (acting as an antagonist). Thus, there is bidirectional effect in terms of efficacy modulation at hMOR, where hydrogen substitution at position 11 with fluorine increases efficacy and potency, while increasing the size of the halogen substituent results progressively in diminishing the efficacy, where the bromo-substituted compound is effectively an antagonist.

TABLE 1

|  | $E_{max}$ | $EC_{50}$ (nM) |
| --- | --- | --- |
| DAMGO | 100 | 0.93 [0.66, 1.33] |
| 12 | 26.5 | 158.8 [68.74, 366.90] |
| 13 | 49.0 | 81.55 [45.10, 147.50] |
| 14 | 33.4 | 326.80 [84.17, 1269.00] |
| 15 | <20 | Not determined |

$EC_{50}$ (nM) reported with 95% confidence limits

Figure 2:
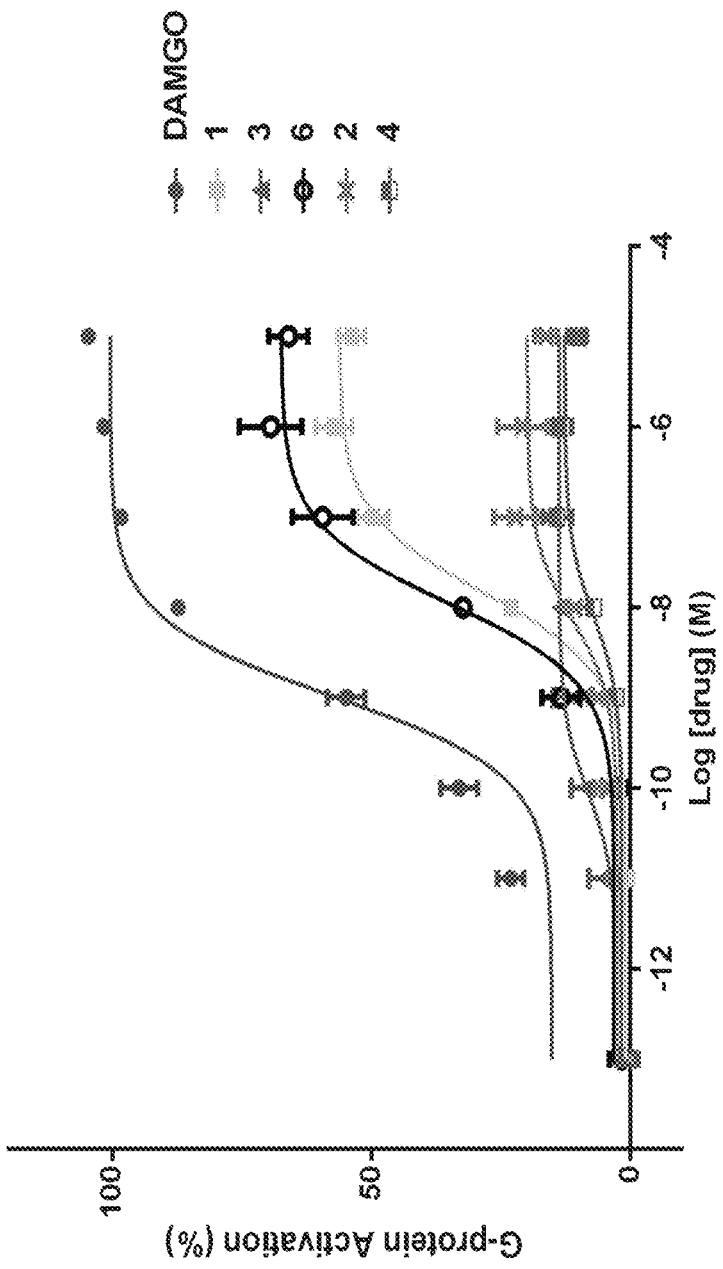
FIG. 2: Agonist activity of compounds 1, 2, 3, 4 and 6 at human MOR; positive control=DAMGO. Bars represent SEM.

We found that the mitragynine-ethylene glycol adduct (MG-EG) (1) acts as a partial agonist at hMOR (compared to the standard ligand DAMGO, FIG. 2). Interestingly, 11-hydroxy-MG-EG (compound 6) showed similar potency and efficacy to its parent, while the halogen substituted compounds, fluoro-(2), chloro-(3) and bromo-derivative (4), showed negligible agonist activity (Table 2). All three halogen substituents in this scaffold decreased efficacy, in contrast to a more complex trend in the parent mitragynine scaffold. Accordingly, these halogenated derivatives are useful as MOR antagonists.

TABLE 2

|  | $E_{max}$ | $EC_{50}$ (nM) |
| --- | --- | --- |
| DAMGO | 100 | 1.43 [1.14, 1.84] |
| 1 | 56.2 | 14.82 [10.62, 20.68] |
| 2 | <20 | — |
| 3 | <20 | — |
| 4 | <20 | — |
| 6 | 67.4 | 11.27 [6.85, 18.55] |

Figure 3:
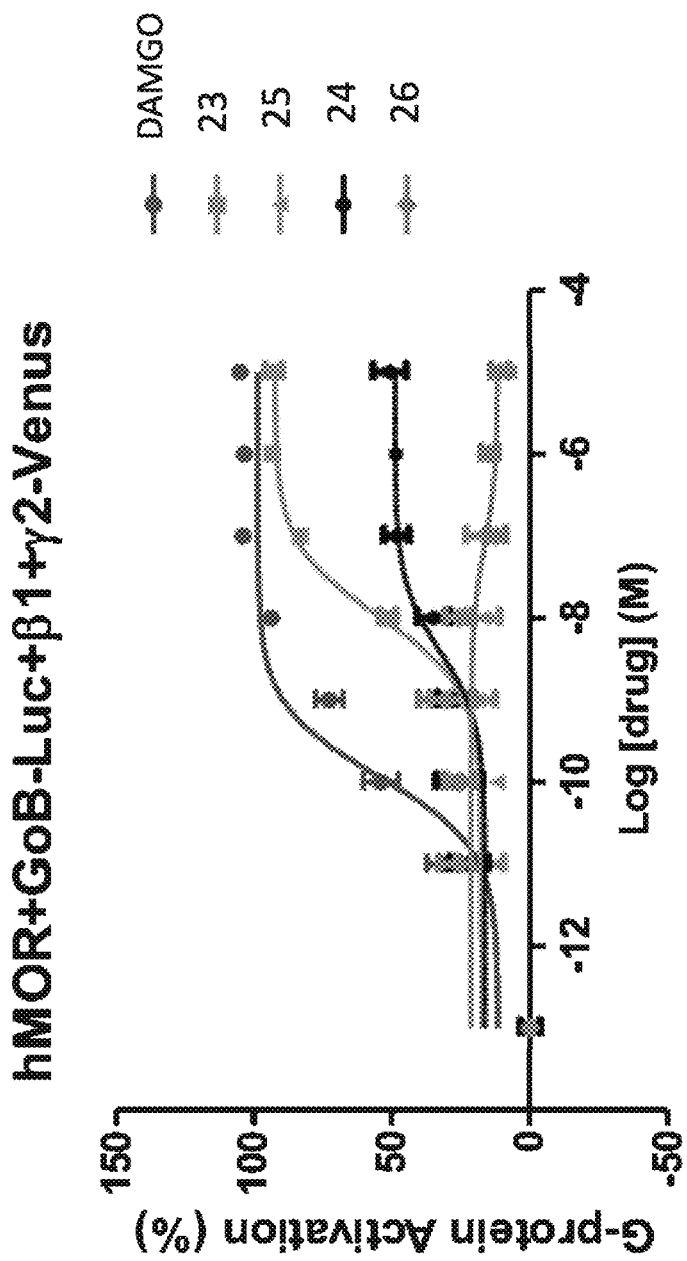
FIG. 3: Agonist activity of compounds 23, 24, 25 and 26 at human MOR; positive control=DAMGO. Bars represent SEM.

$EC_{50}$ (nM) reported with 95% confidence limits 7-hydroxymitragynine (23) is more potent at hMOR in comparison to the parent mitragynine (and comparable to MG-EG), and its efficacy can be dramatically reduced with C11 fluoro (24) substitution rendering a low efficacy agonist ($E_{mac}$=47%, Table 3; FIG. 3). For the corresponding chloro- (25) and bromo-(26) derivatives the agonist activity was abolished and the compounds transformed into antagonists, thus revealing efficacy modulation effects in the C11 halogen series of this scaffold (Table 3). This efficacy modulation is unexpected and unpredictable on the basis of current knowledge of the field, and provides a structural tool to fine-tune receptor signaling, and in turn, a handle for modulation and optimization of the preclinical and clinical effects of such compounds.

TABLE 3

|  | $E_{max}$ | $EC_{50}$ (nM) |
| --- | --- | --- |
| DAMGO | 100 | 0.12 [0.07, 0.19] |
| 23 | 88 | 10.7 [6.57, 17.6] |
| 24 | 47 | 3.98 [0.65, 24.2] |
| 25 | <20 | Not determined |
| 26 | <20 | Not determined |

$EC_{50}$ (nM) reported with 95% confidence limits

Example 3. Binding Data at Opioid Receptors

Radioligand binding studies were performed to assess the affinity of the 7-OH series of compounds at the opioid receptors.

Unexpectedly, the results showed that C11 halogen modulates affinity across all three opioid receptors, as the 11-fluoro compound 24 exhibited greater affinity compared to the parent 7-OH, while this gain in binding is progressively lost as the halogen becomes larger (compounds 25 and 26, Table 4.). The effect was most pronounced at KOR where the affinity of 24 was six times greater than that of the parent compound 23. The 11-fluoro compound 24 also had more that 2-fold greater affinity for DOR when compared to 7-OH, 23. At KOR and DOR, these compounds showed no agonist activity (not shown) and thus are expected to be antagonists at these receptors (the parent 7-OH compound is an antagonist at KOR/DOR) (Kruegel, A. C. et al. 2016).

TABLE 4

Binding data Ki (nM, mean +/- SE, n = 3) in CHO transfected with mouse opioid receptors.

| Compound number | Compound | MOR | KOR | DOR |
| --- | --- | --- | --- | --- |
| 23 | 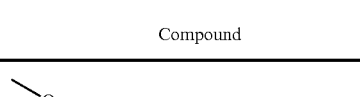 | 21.45 ± 0.81 | 119 ± 2.14 | 88.49 ± 9.86 |

TABLE 4-continued

Binding data Ki (nM, mean +/− SE, n = 3) in CHO transfected with mouse opioid receptors.

| Compound number | Compound | MOR | KOR | DOR |
|---|---|---|---|---|
| 24 | (structure with F) | 13.65 ± 1.01 | 20.96 ± 3.26 | 35.81 ± 2.01 |
| 25 | (structure with Cl) | 27.13 ± 1.12 | 30.621 ± 11.35 | 47.17 ± 2.36 |
| 26 | (structure with Br) | 32.37 ± 1.42 | 81.12 ± 7.11 | 57.74 ± 6.66 |

Figure 4:
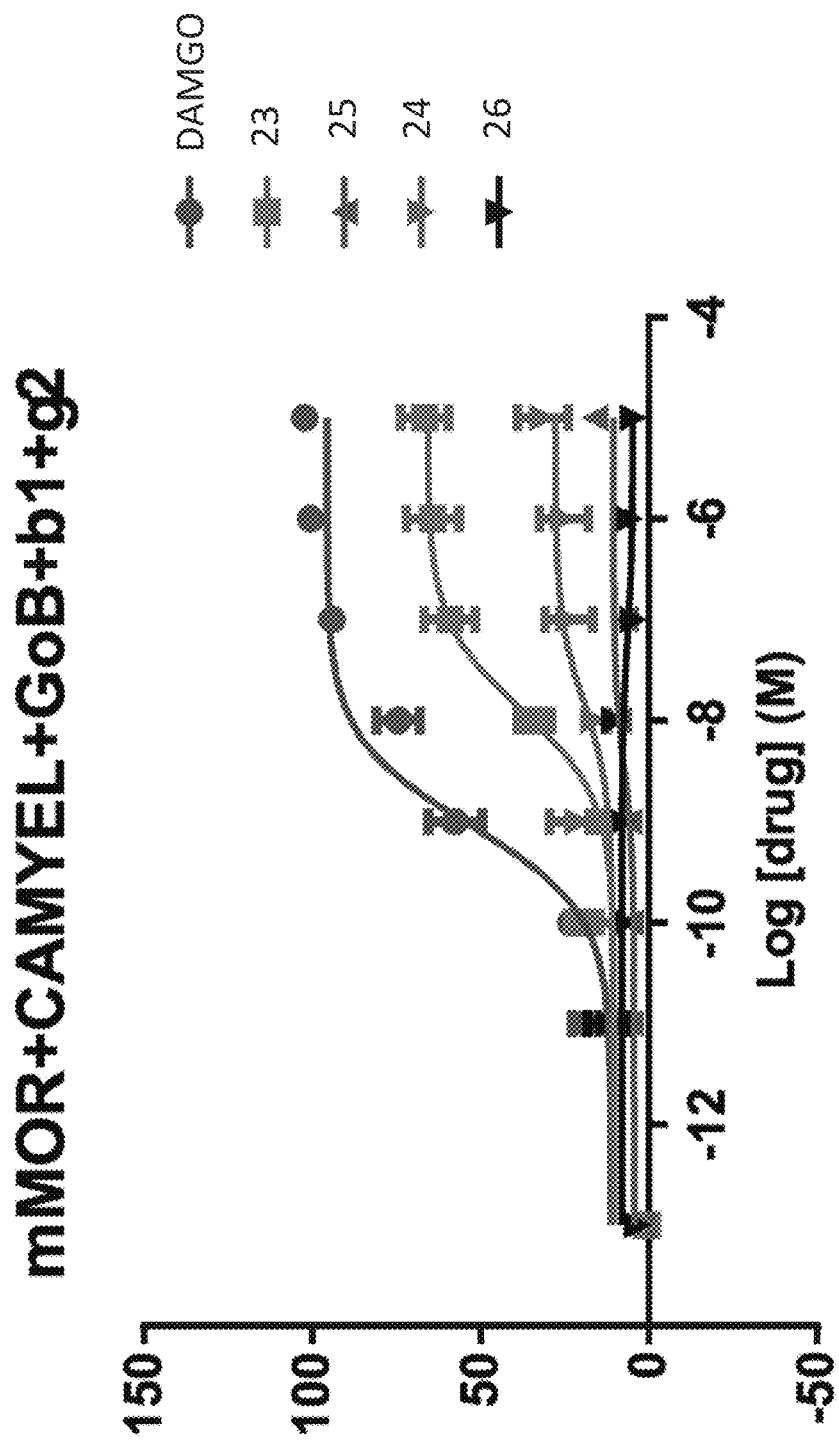
FIG. 4: Agonist activity of compounds 23, 24, 25, and 26 at mouse MOR; positive control=DAMGO. Bars represent SEM.

The results at mMOR demonstrate that the 11-fluoro compound 24 showed approximately 2-fold gain in affinity as referenced to the parent 7-OH, 23. As the new compound 24 exhibited a low agonist efficacy at hMOR (FIG. 3), we also examined the entire series at mMOR in a functional assay (FIG. 4); the cAMP sensor CAMYEL assay was used. The fluoro substituent strongly attenuated the maximal response efficacy compared to the parent compound, while the chloro and bromo derivatives, 25 and 26 respectively, were not agonists. Overall, the 7-OH series showed a similar trend at both mouse and human MOR receptors (FIG. 4, Table 5).

TABLE 5

|  | Emax | EC50 (nM) |
|---|---|---|
| DAMGO | 100 | 0.94 [0.59, 1.50] |
| 23 | 92.4 | 13.01 [5.50, 30.78] |
| 24 | 63.8 | 15.12 [0.62, 371.50] |
| 25 | <20 | Not determined |
| 26 | <20 | Not determined |

$EC_{50}$ (nM) reported with 95% confidence limits

Example 4. Administration of MOR Agonists

An amount of any one of the compounds of the present application is administered to a subject afflicted with a depressive disorder, an anxiety disorder, or a mood disorder. The amount of the compound is effective to treat the subject.

An amount of any one of the compounds of the present application is administered to a subject afflicted with pain. The amount of the compound is effective to treat the subject.

An amount of any one of the compounds of the present application is administered to a subject afflicted with borderline personality disorder. The amount of the compound is effective to treat the subject.

An amount of any one of the compounds of the present application is administered to a subject afflicted with opioid addiction or opioid withdrawal symptoms. The amount of the compound is effective to treat the subject.

Example 5. Combinations with NMDA Receptor Antagonists

Antagonists of the N-methyl-D-aspartate receptor (NMDAR) are known to potentiate the beneficial effects of opioid receptor agonists in the treatment of pain and to prevent the development of tolerance to those effects (Trujillo, K. A. et al. 1994; Mao, J. et al. 1996). NMDAR antagonists are also known to be effective in the treatment of depression (Murrough, J. W. et al. 2013). Therefore, pharmaceutical compositions of the compounds disclosed herein, combined with NMDAR antagonists, may be useful in the treatment of pain, anxiety disorders or mood disorders with increased efficacy and/or slower development of tolerance. Alternatively, the opioid modulator and NMDAR antagonist may be dosed separately, as a novel method for treating pain, anxiety disorders or mood disorders.

Non-Limiting Examples of NMDA Receptor Antagonists:
  Dextromorphinans—dextromethorphan, dextrorphan, dextrallorphan
  Adamantanes—memantine, amantadine, rimantadine, nitromemantine (YQW-36)
  Arylcyclohexylamines—ketamine (and its analogs, e.g. tiletamine), phencyclidine (and its analogs, e.g. tenocyclidine, eticyclidine, rolicyclidine), methoxetamine (and its analogs), gacyclidine (GK-11);
  Miscellaneous—neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A), AP-7

Example 6. Combinations with NMDA Receptor Partial Agonists

Weak partial agonists of NMDAR are also known (Moskal, J. R. et al. 2005), and may be expected to produce beneficial or synergistic effects similar to an antagonist when intrinsic glutamate signaling activity is high or overactivated. Therefore, pharmaceutical compositions of the novel compounds disclosed herein, combined with NMDAR partial agonists, may be useful in the treatment of pain, anxiety disorders or mood disorders with increased efficacy and/or slower development of tolerance. Alternatively, the opioid modulator and NMDAR partial agonist may be dosed separately, as a novel method for treating pain, anxiety disorders or mood disorders.

Non-Limiting Examples of NMDA Receptor Partial Agonists:
  NRX-1074, rapastinel (GLYX-13)

Example 7. Combinations with Neurokinin 1 Receptor Antagonists

Antagonists of the neurokinin 1 receptor (NK-1) are known to modulate the effects of opioid agonists, specifically in reward and self-administration protocols. More specifically, NK-1 antagonists attenuate opioid reward and self-administration in animal models (Robinson, J. E. et al. 2012). NK-1 antagonists are also known to be effective in the treatment of depression (Kramer, M. S. et al. 2004). Therefore, pharmaceutical compositions of the novel compounds disclosed herein, combined with NK-1 antagonists, may be useful in the treatment of pain, anxiety disorders or mood disorders with increased efficacy and/or less potential for abuse. Alternatively, the opioid modulator and NK-1 antagonist may be dosed separately, as a novel method for treating pain, anxiety disorders or mood disorders.

Non-Limiting Examples of Neurokinin 1 Receptor Antagonists:
  aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888, GR 82334

Example 8. Combinations with Neurokinin 2 Receptor Antagonists

Antagonists of the neurokinin 2 receptor (NK-2) are known to show antidepressant effects and to synergize with tricyclic antidepressants (Overstreet, D. H. et al. 2010). Therefore, pharmaceutical compositions of the novel compounds disclosed herein, combined with NK-2 antagonists, may be useful in the treatment of anxiety disorders or mood disorders with increased efficacy. Alternatively, the opioid modulator and NK-2 antagonist may be dosed separately, as a novel method for treating anxiety disorders or a mood disorders.

Non-Limiting Examples of Neurokinin 2 Receptor Antagonists:
  saredutant, ibodutant, nepadutant, GR-159897, MEN-10376

Example 9. Combinations with Neurokinin 3 Receptor Antagonists

Antagonists of the neurokinin 3 receptor (NK-3) are known to show antidepressant effects (Salome, et al. 2006). Further, the actions of NK-3 modulators show a dependency on the opioid receptor system (Panocka, I. et al. 2001). Therefore, pharmaceutical compositions of the novel compounds disclosed herein, combined with NK-3 antagonists, may be useful in the treatment of anxiety disorders or mood disorders with increased efficacy. Alternatively, the opioid modulator and NK-3 antagonist may be dosed separately, as a novel method for treating anxiety disorders or mood disorders.

Non-Limiting Examples of Neurokinin 3 Receptor Antagonists:
  osanetant, talnetant, SB-222200, SD-218795

Example 10. Combinations with DOR Agonists

DOR Agonists have also been shown to elicit antidepressant and anxiolytic effects (Saitoh, A. et al. 2004; Torregrossa, et al. 2005; Jutkiewicz, E. M. 2006) and are analgesic (Vanderah, T. W. 2010; Peppin, J. F. and Raffa, R. B. 2015). They have also been shown to reverse the respiratory depression induced by MOR agonists (Su, Y-F. et al. 1998). Therefore, pharmaceutical compositions of the novel compounds disclosed herein, combined with DOR agonists, may be useful in the treatment of pain, anxiety disorders, or mood disorders with increased efficacy or reduced side effects. Alternatively, the opioid modulator and DOR agonist may be dosed separately, as a novel method for treating pain, anxiety disorders or mood disorders.

Non-Limiting Examples of DOR Agonists:

tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863, 7-spiroindanyloxymorphone.

Example 11. Combinations with Naloxone

Naloxone is an MOR antagonist that is effective in blockading all behavioral effects induced by classical MOR agonists and is the standard treatment for opioid overdose. It is highly bioavailable by parenteral routes of administration but not by the oral route (Smith, K. et al. 2012). Accordingly, pharmaceutical compositions containing mixtures of an MOR agonist and naloxone remain effective agonists when given by the oral route but the naloxone component inhibits the effects of the MOR agonist component when the mixture is administered parenterally. Thus, addition of naloxone to pharmaceutical compositions containing MOR agonists is useful for preventing their misuse or abuse by parenteral routes of administration. Therefore, pharmaceutical compositions of the compounds of the present invention, combined with naloxone, may be useful in providing the therapeutic benefits of the compounds of the present invention while having diminished potential for abuse.

Example 12. Combinations With SSRI or SNRIs

Selective serotonin reuptake inhibitors (SSRIs) and serotonin-norepinephrine reuptake inhibitors (SNRIs) are the standard of care for a many depressive disorders and mood disorders (Thase, M. E. 2008; Vaswani, M. et al. 2003). They are also useful in the treatment of chronic pain (Marks, D. M. et al. 2009). Therefore, pharmaceutical compositions of the compounds of the present invention, combined with SSRIs or SNRIs, are useful in the treatment of depressive disorders, mood disorders, borderline personality disorder, or pain with increased efficacy compared to the compounds of the present invention alone. Alternatively, the opioid modulator and SSRI or SNRI may be dosed separately, as a novel method for treating the conditions described above. Further, the compound of the present invention may be used as an add-on therapy to enhance the efficacy of preexisting SSRI or SNRI therapy for the conditions described above.

Non-Limiting Examples of SSRIs:

citalopram, escitalopram, fluoxetine, fluvoxamine, paroxetine, sertraline, dapoxetine Non-Limiting Examples of SNRIs:

venlafaxine, desvenlafaxine

Example 13. Combinations with Methylnaltrexone

Constipation is a frequent, unpleasant side effect of MOR agonists resulting from inhibition of intestinal smooth muscle contractions via activation of MORs located in this tissue. Methylnaltrexone (Relistor) is a clinically approved quaternary ammonium salt of the opioid receptor antagonist naltrexone that does not cross the blood brain barrier. Accordingly, this compound is capable of inhibiting MORs in the gastrointestinal tract and preventing opioid-induced constipation while avoiding simultaneous inhibition of centrally mediated therapeutic effects. Therefore, pharmaceutical compositions of the compounds of the present invention, combined with methylnaltrexone, are useful in the treatment of depressive disorders, mood disorders, borderline personality disorder, pain, opioid addiction, or opioid withdrawal symptoms with reduced constipation compared to the compounds of the present invention alone. Alternatively, the opioid modulator and methylnaltrexone may be dosed separately, as a novel method for treating the conditions described above with less constipation.

Example 14. Examination of the R9 Substituent

The deletion of the C20-ethyl group (R9) in the mitragynine scaffold led to a 40-fold drop in hMOR activity (from $EC_{50}$~300 nM to 12,000 nM, BRET G protein activation assay) (Kruegel et al 2016). The important role of the ethyl group on ring D can be rationalized by the predicted lowest-energy binding pose, where the ethyl group binds to the same region as the N-methyl group of BU72 (a morphinan agonist compound used for co-crystallization with MOR) (Huang, W. et al. 2015). This is a deep receptor pocket (formed by $T326^{7.43}$, $W293^{6.48}$, $M151^{3.36}$) filled with hydrogen bonded water molecules that accommodates the N-alkyl substituents of morphinans, where increasing the size of this alkyl group has dramatic SAR consequences at MOR (Furst, Z. et al. 1995). In terms of the C20 ethyl group (R9) in mitragynine and related scaffolds, this presents unprecedented SAR opportunities for exploration in terms of modulating selectivity, potency, and efficacy; hence the analogs described in this application.

Examination of the Aromatic Ring.

Limited precedent provides a strong rationale for exploring the aromatic ring substitution. For example, in the C10 position (R5), a small series of compounds has been reported, showing that small substituents are tolerated, and interestingly C10 substituents such as fluorine recruit binding activity at DOR and KOR in addition to MOR (Matsumoto, K. 2014).

Herein, exploration of the other positions (e.g. R6 and R7) and their combinations, which have not been readily accessible via synthesis before (see the new synthetic approach developed here), are explored. Our results described here (FIG. 1-4, and Table 1-5) demonstrate that C11 substitution has unexpected effects on the efficacy of G protein signaling at MOR, which is important as detailed in the Discussion section.

Discussion

Agonists of the MOR may also be used as Maintenance (replacement) therapies in the treatment of opioid addiction. In this case, an opioid (e.g. buprenorphine or methadone) is provided to the patient chronically and under medical supervision to substitute for the use of illicit opioids (e.g. heroin), thus reducing cravings for, and abuse of, the illicit drug. Opioid maintenance therapy has a proven record of efficacy that appears superior to antagonist or behavioral interventions (Bart, G. et al. 2012). However, it is estimated that only <10% of patients with opioid use disorder receive medication-assisted treatment, and thus there is a growing and urgent need for implementation of this therapeutic approach. Consequently, there is a need for safer opioid compounds where the known side effects of typical MOR agonists (e.g. respiratory depression or addictive liability) are attenuated.

Antagonists and low efficacy partial agonists of the MOR are also useful as treatments for opioid overdose (Volkow, N. D. et al. 2017). Although the opioid antagonist naloxone is already used for this purpose, the recent increase in availability of highly potent opioids (e.g. fentanyl derivatives) on the illicit market has resulted in opioid overdoses from such compounds, which by virtue of the high potency (as well as rapid brain penetration) of the overdose-inducing agonist, are challenging to reverse with naloxone, except when very high doses are administered (Kuczynska, K. et al. 2018; Kim, H. K. et al. 2015; Wong, A. et al. 2015; Behar, E. et al. 2018). Lastly, naloxone has a short duration of action and is more rapidly eliminated from the circulation than many commonly abused opioid agonists. Thus, unless repeated doses of naloxone are given to a subject, that subject may relapse into an overdose state as naloxone is cleared from the body (Kim, H. K. et al. 2015; Armenian, P. et al. 2017). Given the forgoing shortcomings of naloxone, new antagonists or low efficacy partial agonists of the MOB with enhanced potency, brain bioavailability, or duration of action represent new more effective tools for managing opioid overdose.

The psychoactive plant *Mitragyna speciosa* has been used for centuries in Southeast Asia for treatment of pain, fatigue, opium dependence, and a number of other ailments. A number of alkaloids in this plant, including mitragynine and 7-hydroxymitragynine (7-OH), have been found to bind to opioid receptors and represent novel molecular scaffolds for the development of opioid receptor modulators. We have previously shown that mitragynine is a partial MOR agonist with a bias for G protein signaling (showing no β-arrestin-2 recruitment) in cell assays. Further, we have found that 7-OH is a more potent, partial G protein-biased MOR agonist that acts as a potent analgesic in mice (Kruegel, A. C. et al. 2016; Matsumoto, K. et al. 2004). Mitragynine and 7-OH, as indole alkaloids, show no structural resemblance to traditional morphine-type compounds and represent atypical opioid ligands with distinct physiological and signaling properties from clinically used opioid analgesics. In preclinical studies, for example, mitragynine exhibited antinociceptive effects in dogs comparable to those of codeine but with less respiratory depression (Mäcko, E. et al. 1972), and further mitragynine was not self-administered by rats and inhibited self-administration of morphine and heroin (Hemby, S. et al. 2018; Kai Yue et al 2018).

Described herein is the synthesis and biological activity of analogs of mitragynine, 7-hydroxymitragynine, mitragynine-ethylene glycol adduct (MG-EG), and mitragynine pseudoindoxyl, substituted at the C11 position (C11 analogs) which represent novel analogs of mitragynine and mitragynine-related scaffolds. Synthesis of these compounds was enabled by a new synthetic approach based on direct and selective C—H borylation of protected mitragynine, and subsequent transformation of the boronate ester to the desired substituent (e.g. —Cl, —Br, —OH, —CN, —CF$_3$, CH$_3$, etc.). This sequence allows for the synthesis of mitragynine derivatives that have not been readily accessible by previous synthetic approaches and thus have not been examined in terms of their biological activity. C11-substituted mitragynine-type alkaloids showed unexpected effects on opioid receptor pharmacology and thus represent new chemical modulators of opioid receptors. Modification of the borylation protocol also allows for efficient preparation of C12 analogs. Further, combining the "late stage functionalization" of mitragynine (and related compounds) with standard electrophilic substitution reactions provides access to the corresponding di-substituted analogs with 10,11-, 10,12-, and 11,12-substitution patterns.

These novel compounds act as modulators of one or more of the MOR, DOR, and/or KOR. Binding and functional assays of these compounds at the opioid receptors show that by selection of the appropriate substituent at the C11 and/or C12 positions, the potency, maximal efficacy ($E_{max}$), and subtype selectivity can be altered. For example, introduction of C11 halo substituents in the 7-hydroxymitragynine scaffold provides compounds 24-26, which at the MOR are either partial agonists with lower $E_{max}$ compared to the parent compound or antagonists. For partial agonists of MOR, reducing the $E_{max}$ is useful for maintaining therapeutic effects (e.g. analgesia or antidepressant activity or opioid withdrawal symptom management) while attenuating negative side effects (e.g. respiratory depression). Antagonists of MOR are useful in their own right for reversal of opioid-induced respiratory depression or as treatments for opioid-use and alcohol-use disorder (Klein, J. W. 2016; Soyka, M. and Mutschler, J. 2015). At the same Lime, both 7-hydroxymitragynine and compounds 24-26 act as antagonists of the KOR and DOR. Antagonists of KOR are useful as antidepressants (Carlezon, W. A. of al. 2016), while antagonism of DOR simultaneous with MOR activation has been shown to attenuate some of the side effects of the MOR agonist component (analgesia tolerance and physical dependence, Ananthan, S. et al. 2006; Mosberg, H. I. et al. 2014; Schiller, P. W. et al. 1999; Ananthan, S. 2012; Healy, J. R. et al. 2013; Schiller, P. W. et al. 1999), while retaining therapeutic properties (e.g. analgesia or antidepressant effects) (Subramanium, A. et al. 1998). Interestingly, compounds 24-26 show increased binding affinity for KOR and DOR compared to 7-hydroxymitragynine. Thus, these compounds exemplify the importance of C11 substitution as an important handle for tuning the potency, efficacy, and subtype selectivity of mitragynine-type compounds at opioid receptors, which are important parameters in the design of experimental therapeutics.

Mitragynine can be extracted directly from kratom leaf matter in multigram quantities. Hence there is a need for developing synthetic techniques to obtain mitragynine analogs through late-stage C—H functionalization of mitragynine rather than via laborious total (de novo) synthesis. The methods of this invention provide for rapid and selective functionalization of the aromatic ring of mitragynine at the C11 and C12 positions.

REFERENCES

Ananthan, S. et al. Synthesis, Opioid Receptor Binding, and Bioassay of Naltrindole Analogues Substituted in the Indolic Benzene Moiety. *Journal of Medicinal Chemistry* 1998, 41 (15), 2872-2881.

Ananthan, S. Opioid Ligands with Mixed μ/δ Opioid Receptor Interactions: An Emerging Approach to Novel Analgesics. *The AAPS Journal* 2006, 8 (1), E118-F125.

Ananthan, S. et al. 14-Alkoxy- and 14-Acyloxypyridomorphinans: μ Agonist/δ Antagonist Opioid Analgesics with Diminished Tolerance and Dependence Side Effects. *Journal of Medicinal Chemistry* 2012, 55 (19), 8350-8363.

Antropow, A. H. et al. Enantioselective Synthesis of (−)-Vallesine: Late-Stage C17-Oxidation via Complex Indole Boronation. *Organic Letters* 2018, 20 (12), 3647-3650.

Armenian, P. et al. Fentanyl, Fentanyl Analogs and Novel Synthetic Opioids: A Comprehensive Review. *Neuropharmacology* 2018, 134, 121-132.

Banerjee, U. et al. Synthesis, and Evaluation of Hybrid Vitamin D3 Side Chain Analogues as Hedgehog Pathway Inhibitors. *Bioorganic Medicinal Chemistry* 2015, 23 (3), 548-555.

Bart, G. Maintenance Medication for Opiate Addiction: The Foundation of Recovery. *Journal of Addictive Diseases* 2012, 31 (3), 207-225.

Behar, E.; Bagnulo, R.; Coffin, P. O. Acceptability and Feasibility of Naloxone Prescribing in Primary Care Settings: A Systematic Review. *Prev Med* 2018, 114, 79-87.

Berrocoso, F. et al. Opiates as Antidepressants. *Current Pharmaceutical Design* 2009, 15 (14), 1612-1622.

Besson, A. et al. Discovery of an Oncogenic Activity in P27Kip1 That Causes Stem Cell Expansion and a Multiple Tumor Phenotype. *Genes Dev.* 2007, 21 (14), 1731-1746.

Bevan, T. W. et al. A Colourful Azuiene-Based Protecting Group for Carboxylic Acids. *Tetrahedron* 2018, 74 (24), 2942-2955.

Bodkin, J. A. et al. Buprenorphine Treatment of Refractory Depression. *J Clin Psychopharmacol* 1995, 15 (1), 49-57.

Cai, Y. et al. Strictosidine Synthase Triggered Enantioselective Synthesis of N-Substituted (S)-3,14,18,19-Tetrahydroangustines as Novel Topoisomerase I Inhibitors. *ACS Chemical Biology* 2017, 12 (12), 3086-3092.

Carlezon, W. A.; Krystal, A. D. Kappa-Opioid Antagonists for Psychiatric Disorders: From Bench to Clinical Trials: 2015 ADAA Scientific Research Symposium: KORs in Psychiatric Illness. *Depression and Anxiety* 2016, 33 (10), 895-906.

Chavkin, C. The Therapeutic Potential of K-Opioids for Treatment of Pain and Addiction. *Neuropsychopharmacology* 2011, 36 (1), 369-370.

Choi, J.; Fu, G. C. Transition Metal-Catalyzed Alkyl-Alkyl Bond Formation: Another Dimension in Cross-Coupling Chemistry. *Science* 2017, 356 (6334), Clayton, C. C. et all. Mutation of Three Residues in the Third Intracellular Loop of the Dopamine $D_2$ Receptor Creates an Internalization-Defective Receptor. *Journal of Biological Chemistry* 2014, 289 (48), 33663-33675.

Compton, W. M.; Jones, C. M.; Baldwin, G. T. Relationship between Nonmedical Prescription-Opioid Use and Heroin Use. *New England Journal of Medicine* 2016, 374 (2), 154-163.

Corbett, A. D.; Henderson, G.; McKnight, A. T.; Paterson, S. J. 75 Years of Opioid Research: The Exciting but Vain Quest for the Holy Grail: Opioids and Opioid Peptides. *British Journal of Pharmacology* 2009, 147 (S1), S153-S162.

Furst Z, H. S., and Friedmann T. *Structure-activity relationship of synthetic and semisynthetic opioid agonists and antagonists,* 1995; Vol. 1. pp. 423-440.

Gassaway, M. M.; Rives, M.-L.; Kruegel, A. C.; Javitch, J. A.; Sames, D. The Atypical Antidepressant and Neurorestorative Agent Tianeptine Is a µ-Opioid Receptor Agonist. *Translational Psychiatry* 2014, 4 (7), e411-e411.

Gevorgyan, V.; Liu, J.-X.; Rubin, M.; Benson, S.; Yamamoto, Y. A Novel Reduction of Alcohols and Ethers with a HSiEt3catalytic B(C6F5)3 System. *Tetrahedron Letters* 1999, 40 (50), 8919-8922.

Healy, J. R. et al. Synthesis, Modeling, and Pharmacological Evaluation of UMB 425, a Mixed µ Agonist/δ Antagonist Opioid Analgesic with Reduced Tolerance Liabilities. *ACS Chemical Neuroscience* 2013, 4 (9), 1256-1266.

Hemby, S. R. et al. Liability and Therapeutic Potential of the *Mitragyna speciosa* (Kratom) Alkaloids Mitragynine and 7-Hydroxymitragynine: Kratom Abuse Liability. *Addiction Biology* 2018.

Hendrickson, W. A.; Ward, K. B. Atomic Models for the Polypeptide Backbones of Myohemerythrin and Hemerythrin. *Biochem. Biophys. Res. Commun.* 1975, 66 (4), 1349-1356.

Holton, R. A. et al. First Total Synthesis of Taxol. 2. Completion of the C and D Rings. *Journal of the American Chemical Society* 1994, 116 (4), 1599-1600.

Huang, W. et al. Structural insights into p-opioid receptor activation. *Nature* 2015, 524, 315-321.

Jutkiewicz, E. M. The Antidepressant -like Effects of Delta-Opioid Receptor Agonists. *Molecular Interventions* 2006, 6 (3), 162-169.

Kaburagi, Y.; Kishi, Y. Operationally Simple and Efficient Workup Procedure for TRAF-Mediated Desilylation: Application to Halichondrin Synthesis. *Organic Letters* 2007, 9 (4), 723-726.

Kerschgens, I. P. et al. Total Syntheses of Mitragynine, Paynantheine and Speciogynine via an Enantioselective Thiourea-Catalysed Pictet-Spengler Reaction. *Chemical Communications* 2012, 48 (100), 12243.

Kim, H. K.; Nelson, L. S. Reducing the Harm of Opioid Overdose with the Safe Use of Naloxone: A Pharmacologic Review. *Expert Opinion on Drug Safety* 2015, 14, 1137-1146.

Kirchhoff, J. H. et al. Boronic Acids: New Coupling Partners in Room-Temperature Suzuki Reactions of Alkyl Bromides. Crystallographic Characterization of an Oxidative-Addition Adduct Generated under Remarkably Mild Conditions. *Journal of the American Chemical Society* 2002, 124 (46), 13662-13663.

Klein, J. W. Pharmacotherapy for Substance Use Disorders. *Medical Clinics of North America* 2016, 100 (4), 891-910.

Kramer, M. S. et a). *Neuropsychopharmacology* 2004, 29, 385-392.

Kruegel, A. C. et al. Synthetic and Receptor Signaling Explorations of the Mitragyna Alkaloids: Mitragynine as an Atypical Molecular Framework for Opioid Receptor Modulators. *Journal of the American Chemical Society* 2016, 138 (21), 6754-6764.

Kuczynska, K.; Grzonkowski, P.; Kacprzak, L.; Zawilska, J. B. Abuse of Fentanyl: An Emerging Problem to Face. *Forensic Science International* 2018, 289, 207-214.

Leitch, J. A.; Bhonoah, Y.; Frost, C. G. Beyond C2 and C3: Transition-Metal-Catalyzed C—H Functionalization of Indole. *ACS Catalysis* 2017, 7 (9), 5618-5627.

Lowry, O. H.; Rosebrough, N. J.; Farr, A. L.; Randall, R. J. Protein Measurement with the Folin Phenol Reagent. *J. Biol. Chem.* 1951, 193 (1), 265-275.

Macko, E. et al. Some Observations on the Pharmacology of Mitragynine. *Arch Int Pharmacodyn Ther* 1972, 198 (1), 145-161.

Majumdar, S. et al. Truncated G Protein-Coupled Mu Opioid Receptor MOR-1 Splice Variants Are Targets for Highly Potent Opioid Analgesics Lacking Side Effects. *Proceedings of the National Academy of Sciences* 2011, 108 (49), 19778-19783.

Majumdar, S. et al. Generation of Novel Radiolabeled Opiates through Site-Selective Iodination. *Bioorganic & Medicinal Chemistry Letters* 2011, 21 (13), 4001-4004.

Marks, D. M. et al. Curr. Neuropharmacol. 2009, 7, 331-336.

Matsumoto, K. et al. O Antinociceptive effect of 7-hydroxymitragynine in mice: Discovery of an orally active opioid analgesic from the Thai medicinal herb Mitragyna speciosa. Life Sci. 2004, 74(17), 2143-55.

Matsumoto, K. et al. Orally active opioid mu/delta dual agonist MGM-16, a derivative of the indole alkaloid mitragynine, exhibits potent antiallodynic effect on neuropathic pain in mice. Journal of Pharmacology and Experimental Therapeutics 2014, 348, 383-392.

Matsuo, G. et al. Total Synthesis of Brevetoxin-B. *Journal of the American Chemical Society* 2004, 126 (44), 14374-14376.

Melief, E. J. et al. Duration of Action of a Broad Range of Selective-Opioid Receptor Antagonists Is Positively Correlated with c-Jun N-Terminal Kinase-1 Activation. *Molecular Pharmacology* 2011, 80 (5), 920-929.

Menzel, K.; Fu, G. C. Room-Temperature Stille Cross-Couplings of Alkenyltin Reagents and Functionalized Alkyl Bromides That Possess β Hydrogens. *Journal of the American Chemical Society* 2003, 125 (13), 3718-3719.

Mosberg, H. I. et al. Development of a Bioavailable μ Opioid Receptor (MOPr) Agonist, δ Opioid Receptor (DOPr) Antagonist Peptide That Evokes Antinociception without Development of Acute Tolerance. *Journal of Medicinal Chemistry* 2014, 57 (7), 3148-3153.

Moskal, J. R.; Kuo, A. G.; Weiss, C.; Wood, P. L.; Hanson, A. O.; Kelso, S.; Harris, R. B.; Disterhoft, J. F. *Neuropharmacology* 2005, 49, 1077-1087.

Murrough, J. W. et al. Am. J. Psychiatry 2013, 170, 1134-1142.

Negri, A. et al. Discovery of a Novel Selective Kappa-Opioid Receptor Agonist Using Crystal Structure-Based Virtual Screening. *Journal of Chemical Information and Modeling* 2013, 53 (3), 521-526.

Overstreet, D. H.; Naimoli, V. M.; Griebel, G. Pharmacol. Biochem. Behav. 2010, 96, 206-210.

Pan, Y.-X. et al. Identification and Characterization of Three New Alternatively Spliced μ-Opioid Receptor Isoforms. *Molecular Pharmacology* 1999, 56 (2), 396-403.

Panocka, I.; Massi, M.; Lapo, I.; Swiderski, T.; Kowalczyk M.; Sadowski, B. Peptides 2001, 22, 1037-1042.

Pasternak, C. W.; Pan, Y.-X. Mu Opioids and Their Receptors: Evolution of a Concept. *Pharmacological Reviews* 2013, 65 (4), 1257-1317.

Paul, I. A.; Skolnick, P. Glutamate and Depression. *Annals of the New York Academy of Sciences* 2003, 1003 (1), 250-272.

Paul, S. et al. Ir-Catalyzed Functionalization of 2-Substituted Indoles at the 7-Position: Nitrogen-Directed Aromatic Borylation. *Journal of the American Chemical Society* 2006, 128 (49), 15552-15553.

Peppin, J. F.; Raffa, R. B. J. Clin. Pharm. Ther. 2015, 40, 155-166.

Pickett, J. F. et al. Mild, Pd-Catalyzed Stannylation of Radioiodination Targets. *Bioorganic & Medicinal Chemistry Letters* 2015, 25 (8), 1761-1764.

Poole-Wilson, P. A.; Langer, G. A. Effect of PH on Ionic Exchange and Function in Rat and Rabbit Myocardium. Am. J. Physiol. 1975, 229 (3), 570-581.

Rives, M.-L.; Rossillo, M.; Liu-Chen, L.-Y.; Javitch, J. A. 6'-Guanidinonaltrindole (6'-GNTI) Is a G Protein-Biased K-Opioid Receptor Agonist That Inhibits Arrestin Recruitment. *Journal of Biological Chemistry* 2012, 287 (32), 27050-27054.

Robinson, J. E.; Fish, E. W.; Krouse, M. C.; Thorsell, A.; Heilig, M.; Malanga, C. J. Psychopharmacology 2012, 220, 215-224.

Rouguet, G.; Robert, F.; Méreau, R.; Castet, F.; Renaud, P.; Landais, Y. Silylboranes as New Sources of Silyl Radicals for Chain-Transfer Reactions. *Chemistry—A European Journal* 2012, 18 (3), 940-950.

Saitoh, A.; Kimura, Y.; Suzuki, T.; Kawai, K.; Nagase, H.; Kamei, J. J. Pharmacol. Sci. 2004, 95, 374-380.

Salomé, N.; Stemmelin, J.; Cohen, C.; Griebel, G. Pharmacol. Biochem. Behav. 2006, 83, 533-539.

Schiller, P. W. et al. The Opioid μ Agonist/δ Antagonist DIPP-NH$_2$ [ψ] Produces a Potent Analgesic Effect, No Physical Dependence, and Less Tolerance than Morphine in Rats. *Journal of Medicinal Chemistry* 1999, 42 (18), 3520-3526.

Schiller, P. W.; Weltrowska, G.; Berezowska, I.; Nguyen, T. M.-D.; Wilkes, B. C.; Lemieux, C.; Chung, N. N. The TIPP Opioid Peptide Family: Development of delta Antagonists, delta Agonists, and Mixed mu Agonist/delta Antagonists. *Biopolymers* 1999, 51 (6), 411-425.

Share, J. B. Review of Drug Treatment for Down's Syndrome Persons. Am J Ment Defic 1976, 80 (4), 388-393.

Smith, K.; Hopp, M.; Mundin, G.; Bond, S.; Bailey, P.; Woodward, J.; Bell, D. Int. J. Clin. Pharmacol. Ther. 2012, 50, 360-367.

Soyka, M.; Mutschler, J. Treatment-Refractory Substance Use Disorder: Focus on Alcohol, Opioids, and Cocaine. *Progress in Neuro-Psychopharmacology and Biological Psychiatry* 2016, 70, 148-161.

Soyka, M.; Mutschler, J. Treatment-Refractory Substance Use Disorder: Focus on Alcohol, Opioids, and Cocaine. *Progress in Neuro-Psychopharmacology and Biological Psychiatry* 2016, 70, 148-161.

Stein, J. M. The Effect of Adrenaline and of Alpha- and Beta-Adrenergic Blocking Agents on ATP Concentration and on Incorporation of 32Pi into ATP in Rat Fat Cells. *Biochem. Pharmacol.* 1975, 24 (18), 1659-1662.

Svoboda, K. R.; Adams, C. E.; Lupica, C. R. Opioid Receptor Subtype Expression Defines Morphologically Distinct Classes of Hippocampal Interneurons. *The Journal of Neuroscience* 1999, 19 (3), 85-95.

Takayama, H. et al. New Procedure to Mask the 2,3-π Bond of the Indole Nucleus and Its Application to the Preparation of Potent Opioid Receptor Agonists with a Corynanthe Skeleton. *Organic Letters* 2006, 8 (25), 5705-5708.

Torregrossa, M. M.; Folk, J. E.; Rice, K. C.; Watson, S. J.; Woods, J. H. Psychopharmacology (Berl). 2005, 183, 31-40.

Volkow, N. D.; Collins, F. S. The Role of Science in Addressing the Opioid Crisis. *New England Journal of Medicine* 2017, 377 (4), 391-394.

Trujillo, K. A.; Akil, H. Brain Res. 1994, 633, 178-188.

Thase, M. E. Psychopharmacol. Bull. 2008, 41, 58-85.

Vanderah, T. W. Clin. J. Pain. 2010, 26 Suppl, S10-15.

Wong, A.; Macleod, D.; Robinson, J.; Koutsogiannis; Z.; Graudins, A.; Greene, S. L. Oxycodone/Naloxone Preparation Can Cause Acute Withdrawal Symptoms When Misused Parenterally or Taken Orally. *Clinical Toxicology* 2015, 53 (8), 815-818.

Xiang, X.; Shen, Q.; Wang, J.; Zhu, Z.; Huang, W.; Zhou, X. Utility of Dysprosium Diiodide and Metallic Dysprosium as Reductants in Cyclopropanation Reactions of Alkenes with Dichloromethane. *Organometallics* 2008, 27 (8), 1959-1962.

Yu, T.-P.; Fein, J.; Phan, T.; Evans, C. J.; Xic, C.-W. Orphanin FQ Inhibits Synaptic Transmission and Long-Term Potentiation in Rat Hippocampus. *Hippocampus* 1997, 7 (1), 88-94.

Yue, K.; Kopajtic, T. A.; Katz, J. L. Abuse Liability of Mitragynine Assessed with a Self-Administration Procedure in Rats. *Psychopharmacology* 2018.

Zarate, C. A. et al. A Randomized Trial of an N-Methyl-D-Aspartate Antagonist in Treatment-Resistant Major Depression. *Archives of General Psychiatry* 2006, 63 (8), 856.

What is claimed is:

1. A compound having the structure:

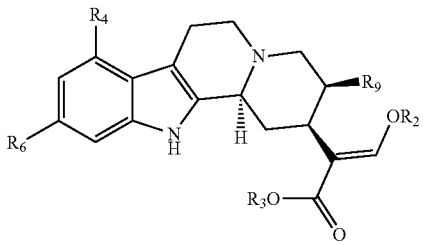

wherein
- $R_2$ and $R_3$ are each, independently, —H or —$CH_3$;
- $R_4$ is —$OCH_3$;
- $R_6$ is —F, —Cl, —Br, —I, —CN, —$CF_3$, —$NO_2$, —OH, —$CH_3$, —$OCH_3$, —C(O)$NH_2$ or phenyl; and
- $R_9$ is —$CH_3$, —$CH_2CH_3$, —$CH_2CH_2CH_3$, —CH=$CH_2$, —$CH_3$CH=$CH_2$, —$CH_2$OH, —$CH_2$— cyclopropyl, —$CH_2$-cyclobutyl or —$CH_2CH_2$-phenyl, or a pharmaceutically acceptable salt thereof; or

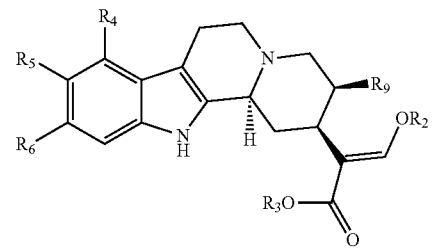

wherein
- $R_2$ and $R_3$ are each, independently, —H or —$CH_3$;
- $R_4$ is —$OCH_3$;
- $R_5$ and $R_6$ are each, independently, —F, —Cl, —Br, —I, —CN, —$CF_3$, —$NO_2$, —OH, —$CH_3$, —$OCH_3$, —C(O)$NH_2$ or phenyl; and
- $R_9$ is —$CH_3$, —$CH_2CH_3$, —$CH_2CH_2CH_3$, —CH=$CH_2$, —$CH_3$CH=$CH_2$, —$CH_2$OH, —$CH_2$— cyclopropyl, —$CH_2$-cyclobutyl or —$CH_2CH_2$-phenyl, or a pharmaceutically acceptable salt thereof; or

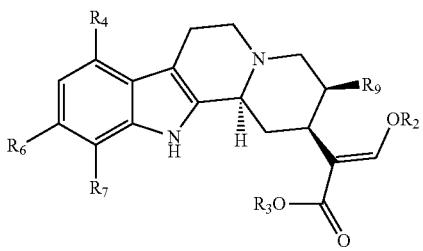

wherein
- $R_2$ and $R_3$ are each, independently, —H or —$CH_3$;
- $R_4$ is —$OCH_3$;
- $R_6$ and $R_7$ are each, independently, —F, —Cl, —Br, —I, —CN, —$CF_3$, —$NO_2$, —OH, —$CH_3$, —$OCH_3$, —C(O)$NH_2$ and

- $R_9$ is —$CH_3$, —$CH_2CH_3$, —$CH_2CH_2CH_3$, —CH=$CH_2$, —$CH_3$CH=$CH_2$, —$CH_2$OH, —$CH_2$— cyclopropyl, —$CH_2$-cyclobutyl or —$CH_2CH_2$-phenyl, or a pharmaceutically acceptable salt thereof; or

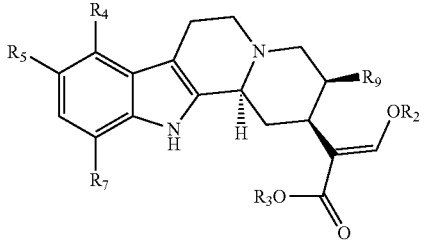

wherein
- $R_2$ and $R_3$ are each, independently, —H or —$CH_3$;
- $R_4$ is —$OCH_3$;
- $R_5$ and $R_7$ are each, independently, —F, —Cl, —Br, —I, —CN, —$CF_3$, —$NO_2$, —OH, —$CH_3$, —$OCH_3$, —C(O)$NH_2$ or phenyl; and
- $R_9$ is —$CH_3$, —$CH_2CH_3$, —$CH_2CH_2CH_3$, —CH=$CH_2$, —$CH_3$CH=$CH_2$, —$CH_2$OH, —$CH_2$— cyclopropyl, —$CH_2$-cyclobutyl or —$CH_2CH_2$-phenyl, or a pharmaceutically acceptable salt thereof.

2. The compound of claim 1 having the structure:

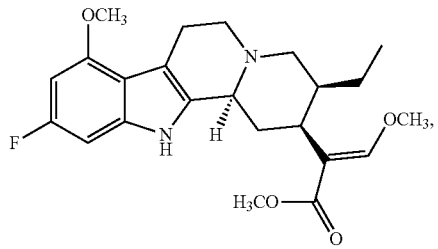

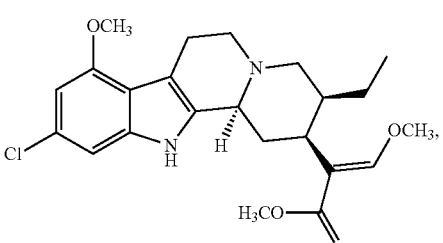

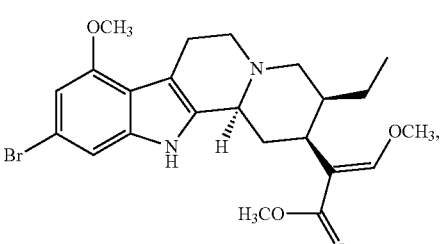

-continued

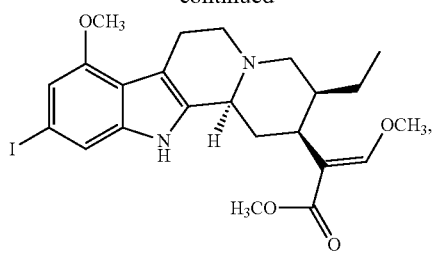

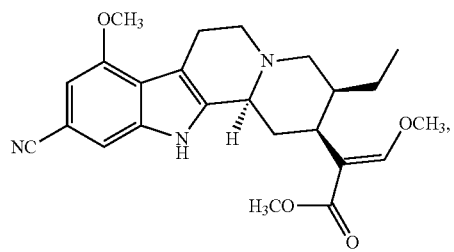

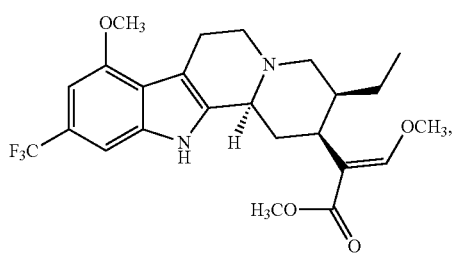

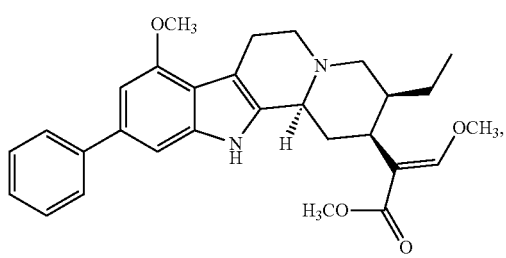

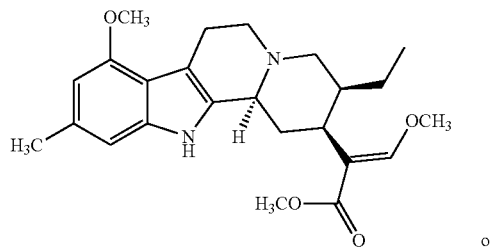

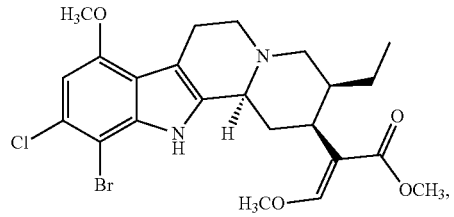

or a pharmaceutically acceptable salt thereof.

3. A compound having the structure:

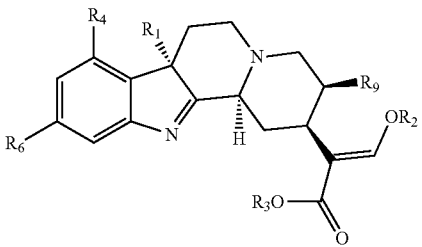

wherein
$R_1$ is —OH;
$R_2$ and $R_3$ are each, independently, —H or —CH$_3$;
$R_4$ is —OCH$_3$;
$R_6$ is —F, —Cl, —Br, —I, —CN, —CF$_3$, —NO$_2$, —OH, —CH$_3$, —OCH$_3$, —C(O)NH$_2$ or phenyl; and
$R_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl,
or a pharmaceutically acceptable salt thereof; or

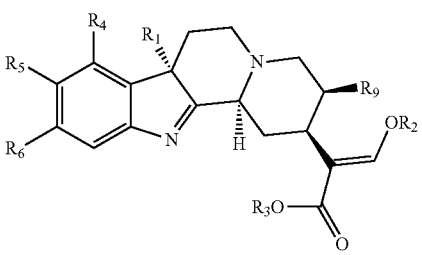

wherein
$R_2$ and $R_3$ are each, independently, —H or —CH$_3$;
$R_4$ is —OCH$_3$;
$R_5$ and $R_6$ are each, independently, —F, —Cl, —Br, —I, —CN, —CF$_3$, —NO$_2$, —OH, —CH$_3$, —OCH$_3$, —C(O)NH$_2$ or phenyl; and
$R_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl,
or a pharmaceutically acceptable salt thereof; or

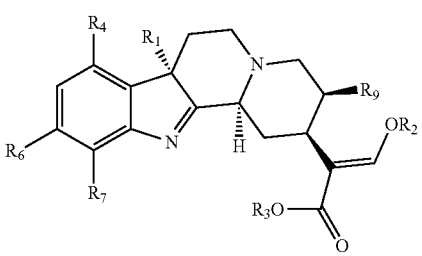

wherein
$R_1$ is —OH;
$R_2$ and $R_3$ are each, independently, —H or —CH$_3$;
$R_4$ is —OCH$_3$;
$R_6$ and $R_7$ are each, independently, —F, —Cl, —Br, —I, —CN, —CF$_3$, —NO$_2$, —OH, —CH$_3$, —OCH$_3$, —C(O)NH$_2$ or phenyl; and R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt thereof; or

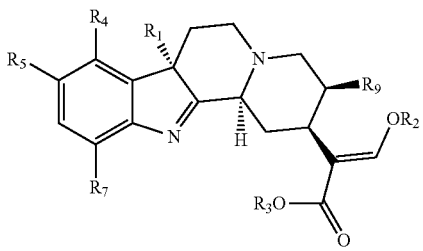

wherein
R$_1$ is —OH;
R$_2$ and R$_3$ are each, independently, —H or —CH$_3$;
R$_4$ is —OCH$_3$;
R$_5$ and R$_7$ are each, independently, —F, —Cl, —Br, —I, —CN, —CF$_3$, —NO$_2$, —OH, —CH$_3$, —OCH$_3$, —C(O)NH$_2$ or phenyl; and
R$_9$ is —CH$_3$, —CH$_2$CH$_3$, —CH$_2$CH$_2$CH$_3$, —CH=CH$_2$, —CH$_3$CH=CH$_2$, —CH$_2$OH, —CH$_2$-cyclopropyl, —CH$_2$-cyclobutyl or —CH$_2$CH$_2$-phenyl, or a pharmaceutically acceptable salt thereof.

4. The compound of claim 3 having the structure:

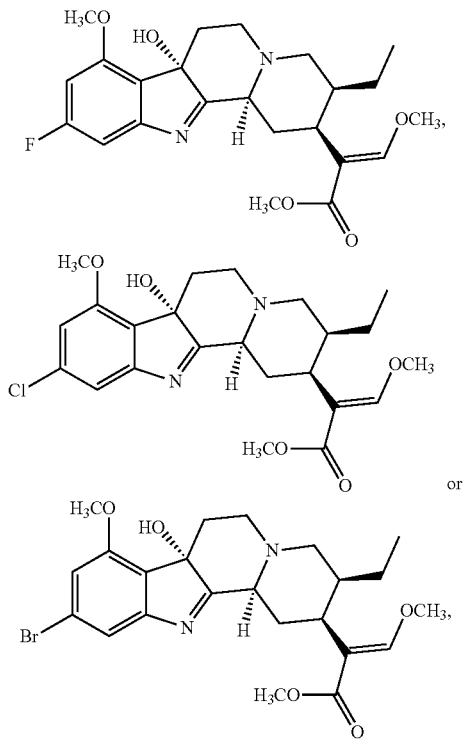

or a pharmaceutically acceptable salt thereof.

5. A pharmaceutical composition comprising the compound of claim 1 and a pharmaceutically acceptable carrier.

6. A method of activating a mu-opioid receptor comprising contacting the mu-opioid receptor with the composition of claim 5; or of antagonizing a mu-opioid receptor, a delta-opioid receptor and/or a kappa-opioid receptor comprising contacting the mu-opioid receptor, the delta-opioid receptor and/or the kappa-opioid receptor with the composition of claim 5.

7. A method of treating a subject afflicted with pain, opioid addiction or opioid withdrawal symptoms comprising administering an effective amount of the composition of claim 5 to the subject so as to thereby treat the subject afflicted with pain, opioid addiction or opioid withdrawal symptoms.

8. A method of treating a subject afflicted with pain comprising administering to the subject an effective amount of an NMDA receptor antagonist, an NMDA receptor partial agonist, a neurokinin 1 receptor antagonist, or a delta-opioid receptor agonist and an effective amount of the composition of claim 5 so as to thereby treat the subject afflicted with pain; or a method of treating a subject afflicted with opioid addiction or opioid withdrawal symptoms comprising administering to the subject an effective amount of an NMDA receptor antagonist, an NMDA receptor partial agonist or a neurokinin 1 receptor antagonist and an effective amount of the composition of claim 5 so as to thereby treat the subject afflicted with the opioid addiction or opioid withdrawal symptoms; or a method of treating a subject afflicted with opioid addiction or opioid withdrawal symptoms comprising administering to the subject an effective amount of naloxone or methylnaltrexone and an effective amount of the composition of claim 5 so as to thereby treat the subject afflicted with the opioid addiction or opioid withdrawal symptoms.

9. A pharmaceutical composition comprising the compound of claim 1, an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone, methylnaltrexone, a selective serotonin reuptake inhibitor or a serotonin-norepinephrine reuptake inhibitor, and a pharmaceutically acceptable carrier.

10. A pharmaceutical composition comprising the compound of claim 3 and a pharmaceutically acceptable carrier.

11. A method of activating a mu-opioid receptor comprising contacting the mu-opioid receptor with the composition of claim 10; or of antagonizing a mu-opioid receptor, a delta-opioid receptor and/or a kappa-opioid receptor comprising contacting the mu-opioid receptor, the delta-opioid receptor and/or the kappa-opioid receptor with the composition of claim 10.

12. A method of treating a subject afflicted with pain, opioid addiction or opioid withdrawal symptoms comprising administering an effective amount of the composition of claim 10 to the subject so as to thereby treat the subject afflicted with pain, opioid addiction or opioid withdrawal symptoms.

13. A method of treating a subject afflicted with pain comprising administering to the subject an effective amount of an NMDA receptor antagonist, an NMDA receptor partial agonist, a neurokinin 1 receptor antagonist, or a delta-opioid receptor agonist and an effective amount of the composition of claim 10 so as to thereby treat the subject afflicted with pain; or a method of treating a subject afflicted with opioid addiction or opioid withdrawal symptoms comprising administering to the subject an effective amount of an NMDA receptor antagonist, an NMDA receptor partial agonist or a neurokinin 1 receptor antagonist and an effective amount of the composition of claim 10 so as to thereby treat the subject afflicted with the opioid addiction or opioid withdrawal symptoms; or a method of treating a subject afflicted with opioid addiction or opioid withdrawal symptoms comprising administering to the subject an effective amount of naloxone or methylnaltrexone and an effective amount of the composition of claim 10 so as to thereby treat the subject afflicted with the opioid addiction or opioid withdrawal symptoms.

14. A pharmaceutical composition comprising the compound of claim 3, an NMDA receptor antagonist, an NMDA receptor partial agonist, a neurokinin 1 receptor antagonist, a neurokinin 2 receptor antagonist, a neurokinin 3 receptor antagonist, a DOR agonist, naloxone, methylnaltrexone, a selective serotonin reuptake inhibitor or a serotonin-norepinephrine reuptake inhibitor, and a pharmaceutically acceptable carrier.

* * * * *